US010800817B2

(12) United States Patent
Bond et al.

(10) Patent No.: US 10,800,817 B2
(45) Date of Patent: Oct. 13, 2020

(54) COMPOSITIONS AND METHODS FOR TREATING DISEASES BY INHIBITING EXOSOME RELEASE

(71) Applicant: MOREHOUSE SCHOOL OF MEDICINE, Atlanta, GA (US)

(72) Inventors: Vincent C. Bond, Stone Mountain, GA (US); James W. Lillard, Jr., Smyrna, GA (US); Ming Bo Huang, Atlanta, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

(21) Appl. No.: 16/226,283

(22) Filed: Dec. 19, 2018

(65) Prior Publication Data
US 2019/0135873 A1 May 9, 2019

Related U.S. Application Data

(63) Continuation-in-part of application No. 16/030,430, filed on Jul. 9, 2018, now Pat. No. 10,544,193, which is a continuation of application No. 15/383,454, filed on Dec. 19, 2016, now Pat. No. 10,040,831.

(51) Int. Cl.

| | |
|---|---|
| *A61K 38/08* | (2019.01) |
| *A61K 35/10* | (2015.01) |
| *A61K 47/64* | (2017.01) |
| *C07K 14/005* | (2006.01) |
| *A61K 47/60* | (2017.01) |
| *C12N 7/00* | (2006.01) |
| *A61K 38/16* | (2006.01) |
| *A61K 45/06* | (2006.01) |
| *A61K 38/10* | (2006.01) |

(52) U.S. Cl.
CPC ............ *C07K 14/005* (2013.01); *A61K 38/08* (2013.01); *A61K 38/10* (2013.01); *A61K 38/162* (2013.01); *A61K 45/06* (2013.01); *A61K 47/60* (2017.08); *A61K 47/64* (2017.08); *A61K 47/641* (2017.08); *A61K 47/645* (2017.08); *C12N 7/00* (2013.01); *C07K 2319/035* (2013.01); *C07K 2319/70* (2013.01); *C12N 2740/16022* (2013.01); *C12N 2740/16322* (2013.01)

(58) Field of Classification Search
CPC ........ A61K 38/03; A61K 38/08; A61K 38/10; A61K 38/16; A61K 38/162; A61K 47/64; A61K 47/645; C07K 4/00; C07K 4/02; C07K 7/06; C07K 7/08; C07K 14/00; C07K 14/63; C07K 2319/01; C07K 2319/035; C07K 2319/70; C07K 2319/74
See application file for complete search history.

(56) References Cited

U.S. PATENT DOCUMENTS

| | | | | |
|---|---|---|---|---|
| 4,569,789 | A | 2/1986 | Blattler et al. | |
| 4,631,190 | A | 12/1986 | Shen et al. | |
| 5,252,714 | A | 10/1993 | Harris et al. | |
| 5,306,809 | A | 4/1994 | Boon et al. | |
| 5,560,234 | A | 10/1996 | Ross et al. | |
| 5,569,754 | A | 10/1996 | Williams et al. | |
| 5,665,358 | A | 9/1997 | Barton et al. | |
| 5,672,662 | A | 9/1997 | Harris et al. | |
| 5,985,263 | A | 11/1999 | Lee et al. | |
| 5,990,237 | A | 11/1999 | Bentley et al. | |
| 8,476,237 | B2 | 7/2013 | Bond et al. | |
| 9,095,618 | B2 * | 8/2015 | Satchi-Fainaro | C07F 9/3873 |
| 10,040,831 | B2 | 8/2018 | Bond et al. | |
| 10,544,193 | B2 * | 1/2020 | Bond | A61K 38/162 |
| 2004/0192627 | A1 | 9/2004 | Weissig et al. | |
| 2008/0160106 | A1 * | 7/2008 | Fais | A61K 31/4439 424/687 |
| 2009/0060846 | A1 * | 3/2009 | Zhang | A61K 49/1845 424/9.32 |
| 2009/0099066 | A1 * | 4/2009 | Moulton | C12N 15/87 514/1.1 |
| 2010/0136129 | A1 * | 6/2010 | Agueros Bazo | A61K 9/0065 424/499 |
| 2010/0247657 | A1 * | 9/2010 | Santos | C12N 9/1241 424/489 |
| 2011/0129549 | A1 * | 6/2011 | Liu | C07D 401/14 424/649 |
| 2012/0121507 | A1 | 5/2012 | Filfil et al. | |
| 2012/0171115 | A1 | 7/2012 | Hudson et al. | |
| 2013/0089525 | A1 | 4/2013 | Bond et al. | |

(Continued)

FOREIGN PATENT DOCUMENTS

| | | |
|---|---|---|
| WO | 99/03499 | 1/1999 |
| WO | 2011/157715 | 12/2011 |
| WO | 2018/118015 | 6/2018 |

OTHER PUBLICATIONS

International Search Report and Written Opinion of International Application No. PCT/US18/66567 dated May 30, 2019.

Lee, M. C.S. et al., “Bi-directional protein transport between the ER and Golgi”, Annu. Rev. Cell Dev. Biol., 2004, vol. 20, pp. 87-123.

Lippincott-Schwartz, J. et al., “Rapid redistribution of Golgi proteins into the ER in cells treated with brefeldin A: evidence for membrane cycling from Golgi to ER”, Cell, 1989 , vol. 56(5), pp. 801-813.

(Continued)

*Primary Examiner* — Jeffrey E. Russel
(74) *Attorney, Agent, or Firm* — Ping Wang; Morris, Manning & Martin LLP

(57) ABSTRACT

A method for treating a cancer comprises administering to a subject in need of such treatment an effective amount of a pharmaceutical composition comprising an anti-cancer agent having at least one secretion modifying region (SMR) peptide from HIV-1 Nef fused to at least one cell-penetrating peptide (CPP) or at least one Clusterin (Clu)-binding peptide (Clu-BP).

20 Claims, 16 Drawing Sheets

Specification includes a Sequence Listing.

(56) References Cited

U.S. PATENT DOCUMENTS

| | | | |
|---|---|---|---|
| 2013/0236396 A1* | 9/2013 | Pease, III | A61K 49/0002 424/9.1 |
| 2014/0121170 A2 | 5/2014 | Bond et al. | |
| 2014/0142121 A1 | 5/2014 | Altieri et al. | |
| 2014/0196172 A1 | 7/2014 | Eudes et al. | |
| 2016/0046936 A1* | 2/2016 | Li | A61K 38/38 424/491 |
| 2016/0237129 A1 | 8/2016 | Keefe et al. | |
| 2017/0365533 A1 | 12/2017 | Bond et al. | |
| 2018/0170969 A1 | 6/2018 | Bond et al. | |

OTHER PUBLICATIONS

Misumi, Y. et al., "Novel blockade by brefeldin A of intracellular transport of secretory proteins in cultured rat hepatocytes", The Journal of Biological Chemistry, 1986, vol. 261(24), pp. 11398-11403.

Muesch, A. et al., "A Novel Pathway for Secretory Proteins?", Trends Biochem. Sci., 1990, vol. 15 (3), pp. 86-88.

Johnstone, R. M. et al., "Vesicle formation during reticulocyte maturation. Association of plasma membrane activities with released vesicles (exosomes)", The Journal of Biological Chemistry, 1987, vol. 262(19), pp. 9412-9420.

Nickel, W., "Unconventional secretory routes: direct protein export across the plasma membrane of mammalian cells", Traffic, 2005, vol. 6(8), pp. 607-614.

Guy, B. et al., "Mutational analysis of the HIV nef Protein", Virology, 1990, vol. 176, pp. 413-425.

Campbell, T. D. et al., "HIV-1 Nef protein is secreted into vesicles that can fuse with target cells and virions", Ethnicity & Disease, 2008, vol. 18(2), pp. S2-14-S2-19.

Sanfridson, A. et al., "Nef proteins encoded by human and simian immunodeficiency viruses induce the accumulation of endosomes and lysosomes in human T cells", Proc. Natl. Acad. Sci., 1997, vol. 94(3), pp. 873-838.

Esser, M. T. et al., "Differential Incorporation of CD45, CD80 (B7-1), CD86 (B7-2), and Major Histocompatibility Complex Class I and II Molecules into Human Immunodeficiency Virus Type 1 Virions and Microvesicles: Implications for Viral Pathogenesis and Immune Regulation", Journal of Virology, 2001, vol. 75(13), pp. 6173-6182.

Lindner, K. et al., "Circulating microRNAs: emerging biomarkers for diagnosis and prognosis in patients with gastrointestinal cancers", Clinical Science (Lond), 2015, vol. 128(1), pp. 1-15.

Salido-Guadarram, I. et al., "MicroRNAs transported by exosomes in body fluids as mediators of intercellular communication in cancer", OncoTargets and Therapy, 2014, vol. 7, pp. 1327-1338.

Morris, M. C. et al., "A peptide carrier for the delivery of biologically active proteins into mammalian cells: Application to the Delivery of antibodies and therapeutic Proteins", Cell Biology, 2006, pp. 13-18.

Joliot, A. et al., "Transduction peptides: from technology to physiology", Nature Cell Biology, 2004, vol. 6(3), pp. 189-196.

Heitz, F. et al., "Twenty years of cell-penetrating peptides: from molecular mechanisms to therapeutics", British Journal of Pharmacology, 2009, vol. 157(2), pp. 195-206.

Gaertner, H. F. et al., "Site-specific attachment of functionalized poly(ethylene glycol) to the amino terminus of proteins", Bioconjugate Chem., 1996, vol. 7(1), pp. 38-44.

Stockert, J. C. et al., "MTT assay for cell viability: Intracellular localization of the formazan product is in lipid droplets", Acta Histochemica, 2012, vol. 114(8), pp. 785-796.

Riss, T. L. et al., "Cell Viability Assays", Assay Guidance Manual, 2013, pp. 1-31.

Ali, S. A. et al., "Genetic Characterization of HIV Type 1 Nef-Induced Vesicle Secretion", AIDS Research and Human Retroviruses, 2010, vol. 26(2), pp. 173-192.

Ellman, G. L. et al., "A new and rapid colorimetric determination of acetylcholinesterase activity", Biochemical Pharmacology, 1961, vol. 7, pp. 88-95.

Shelton, M. N. et al., "Secretion Modification Region-Derived Peptide Disrupts HIV-1 Nef's Interaction with Mortalin and Blocks Virus and Nef Exosome Release", Journal of Virology, 2012, vol. 86(1), pp. 406-419.

File history of U.S. Appl. No. 16/030,430, filed Jul. 9, 2018.
File history of U.S. Appl. No. 15/383,454, filed Dec. 19, 2016.

* cited by examiner

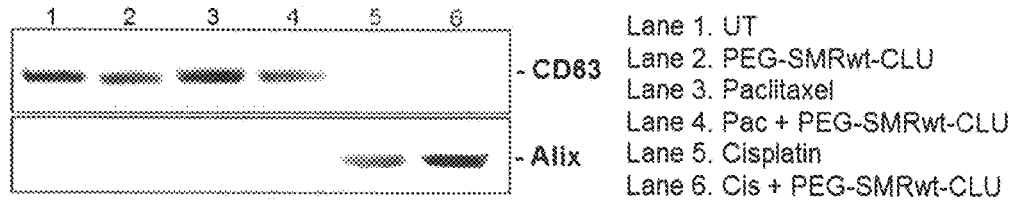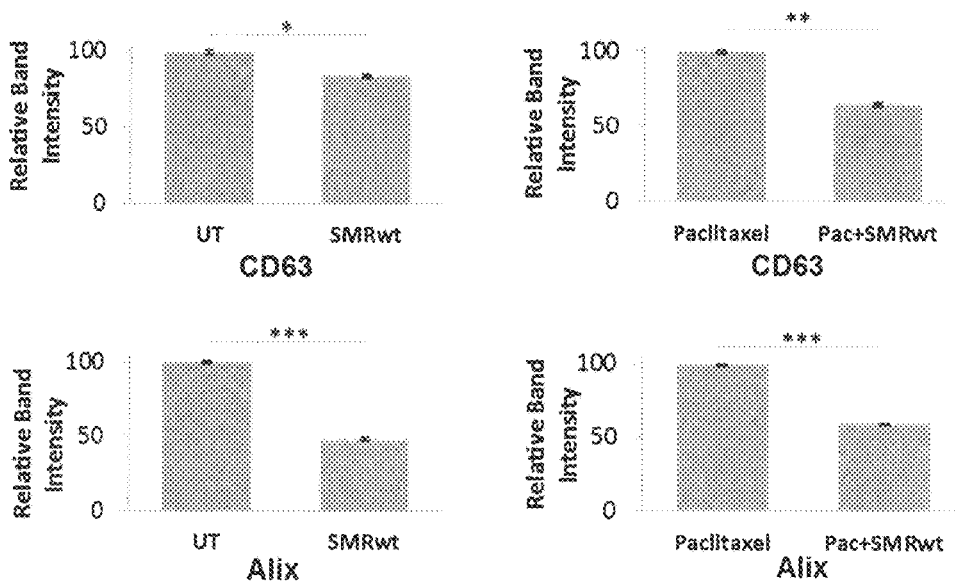
FIG. 5

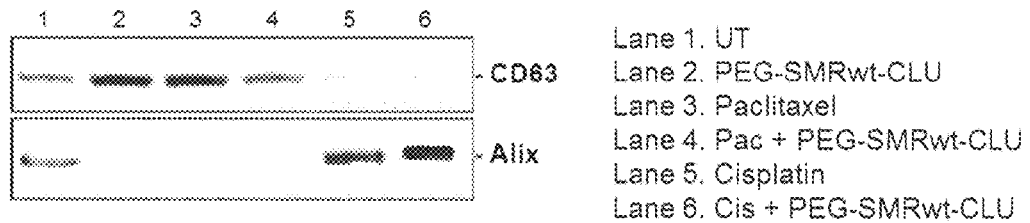
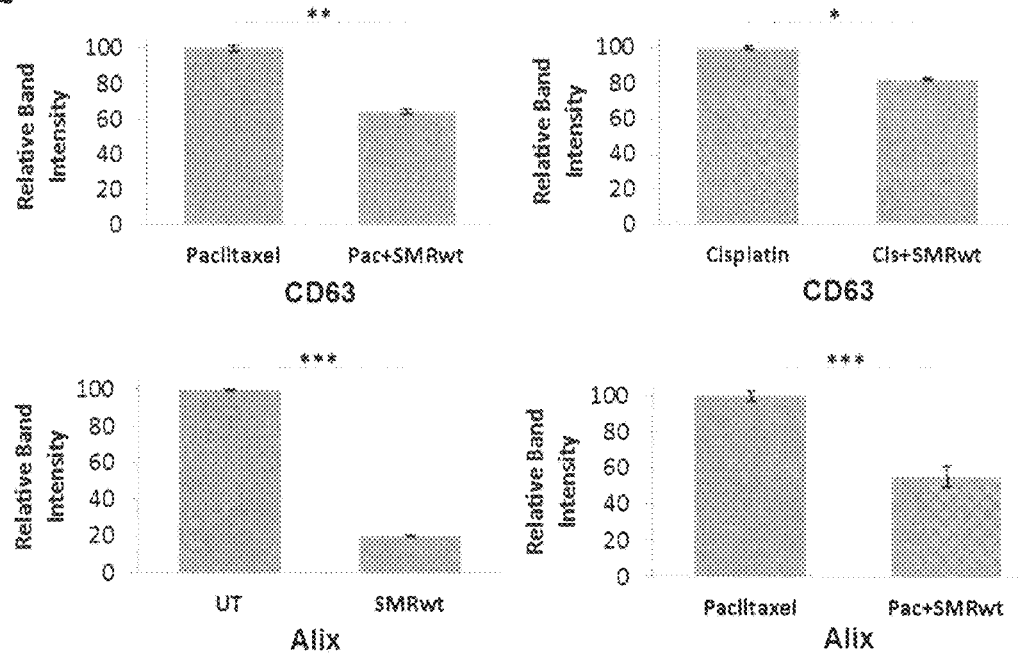
FIG. 6

A

SMRwt-CPPtat Peptide: H2N-SMRwt-CPPtat-OH

H2N-VGFPVAAVGFPV-GRKKRRQRRRPPQ-OH [SEQ ID NO: 39]

H2N - [SEQ ID NO: 2] – [SEQ ID NO: 38] - OH

SMRmut-CPPtat Peptide: H2N-SMRmut-CPPtat-OH

H2N-AGFPVAAAGFPV-GRKKRRQRRRPPQ-OH [SEQ ID NO: 41]

H2N - [SEQ ID NO: 10] – [SEQ ID NO: 38] – OH

B

PEG-SMRwt-CLU Peptide: PEG-SMRwt-CLU-NH2

PEG (10Kd)-NXNVGFPVAAVGFPV-HPLSKHPYWSQP-OH [SEQ ID NO: 37]

PEG (10Kd) – [SEQ ID NO: 36] – [SEQ ID NO: 3]

PEG-SMRmut-CLU Peptide: PEG-SMRmut-CLU-NH2

PEG (10Kd)-NXNAGFPVAAAGFPV-HPLSKHPYWSQP-OH [SEQ ID NO: 43]

PEG (10Kd) – [SEQ ID NO: 42] – [SEQ ID NO: 3]

FIG. 9

A
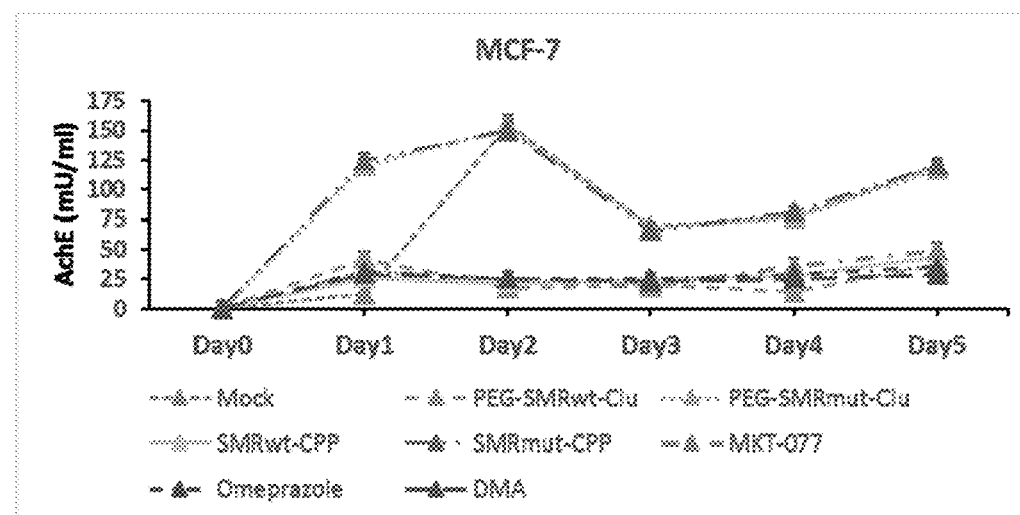
B
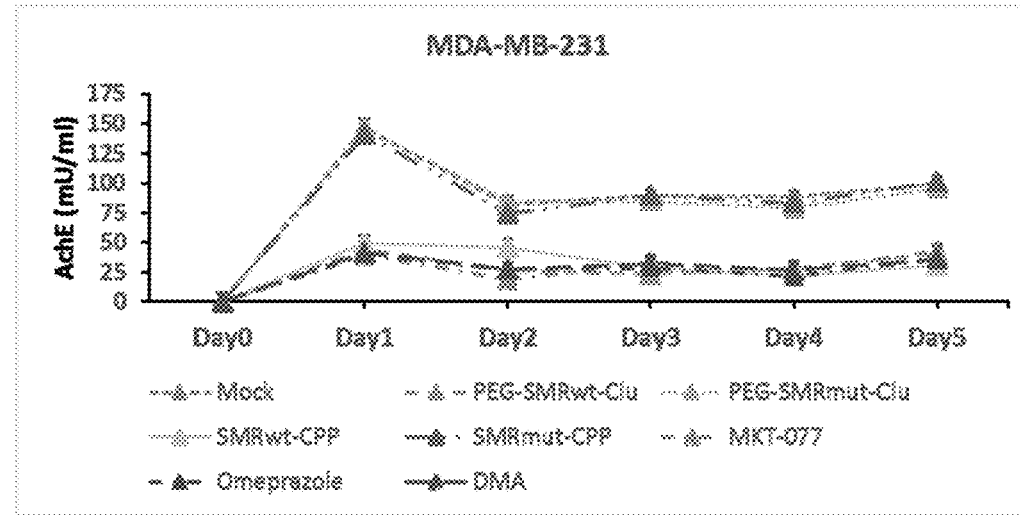
C
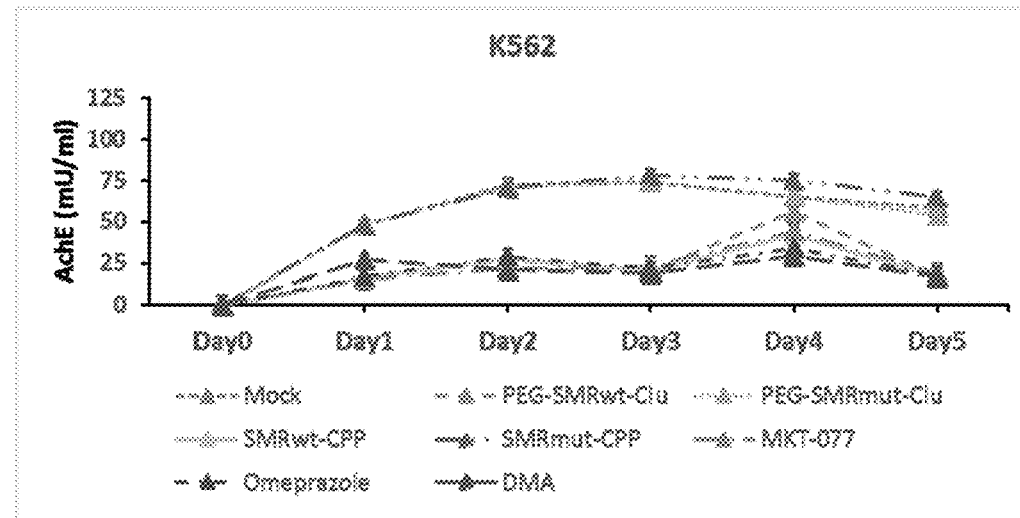
FIG. 11

COMPOSITIONS AND METHODS FOR TREATING DISEASES BY INHIBITING EXOSOME RELEASE

This application is a Continuation-in-Part of U.S. application Ser. No. 16/030,430, filed on Jul. 9, 2018, which is a continuation of U.S. application Ser. No. 15/383,454, filed Dec. 19, 2016, now U.S. Pat. No. 10,040,831. The entirety of the aforementioned applications is incorporated herein by reference.

This application was made with government support under certain grants awarded by NIH. The government has certain rights in the application.

FIELD

The present disclosure generally relates to compositions and methods for medical treatment, and in particular, to methods for treating cancers and infectious diseases by inhibiting exosome release.

BACKGROUND

Membrane exosomes are spherical membrane microvesicles, generally less than 200 nm in diameter. The exosomes are composed of a lipid bilayer containing a cytosolic fraction. Particular membrane vesicles are more specifically produced by cells, from intracellular compartments through fusion with the cytoplasmic membrane of a cell, resulting in their release into the extracellular biological fluids of an organism or into cell culture media. These exosomes may be released in a number of ways. The classical secretory pathway processes mainly traditional membrane signals bearing receptors through the endoplasmic Reticulum (ER) membrane (Lee et al., (2004) Annu. Rev. Cell Dev. Biol. 20, 87-123).

Secretory proteins are packaged into transport vesicles, delivered to the Golgi apparatus, and eventually released of into the extracellular space. Alternatively, nonclassical secretory pathways mediate translocation of cytosolic, non-signal bearing molecules into the extracellular space (Lippincott-Schwartz et al., (1989) Cell 56, 801-813; and Misumi et al., (1986) J. Biol. Chem. 261, 11398-11403). Two of these involve intracellular vesicles of the endocytic membrane system, such as secretory lysosomes (Muesch et al., (1990) Trends Biochem. Sci. 15, 86-88) and exosomes (Johnstone et al., (1987) J. Biol. Chem. 262, 9412-9420), the latter ones being internal vesicles of late endosomes or multivesicular bodies (MVB). Lysosomal contents gain access to the exterior of cells when specialized endocytic structures such as secretory lysosomes of cytotoxic T lymphocytes, fuse with the plasma membrane. Lumenal contents of late endocytic structures are released into the extracellular space when MVBs fuse with the plasma membrane resulting in release of the internal multivesicular endosomes into the extracellular space (called exosomes) along with their cargo molecules. Other nonclassical pathways involve direct translocation of cytosolic factors across the plasma membrane using protein conducting channels or a process called membrane blebbing (Nickel, W. (2005) Traffic. 6, 607-614). Membrane blebbing is characterized by shedding of plasma membrane-derived microvesicles into the extracellular space.

Exosome release has been demonstrated from different cell types in varied physiological contexts. It has been demonstrated that tumor cells secrete exosomes, such as exosomes in a regulated manner, which can carry tumor antigens that can be presented to antigen presenting cells (Patent Application No. WO99/03499). In addition, FasL or TNF containing exosomes are known to cause a state of immune privilege/immune suppression which can promote tumor growth. Similarly, virus-infected cells, including those infected by HIV are known to release Nef-containing exosomes (Guy et al., (1990) Virology 176, 413-425; and Campbell et al., (2008) Ethn. Dis. 18, S2-S9), which serve to suppress the immune system allowing HIV to survive. Exosome secretion has been shown to utilize the same endosomal trafficking pathway involved in virion release from infected cells (Sanfridson et al., (1997) Proc. Natl. Acad. Sci. U.S.A 94, 873-878; and Esser et al., (2001) J Virol. 75, 6173-6182). Tumors are known to release large numbers of exosomes, which can cause immune suppression through immune cell killing or dysregulation, thereby promoting a state of immunosuppression that allows for rapid tumor growth (Lindner K. et al., 2015, Salido-Guadarrama I. et al., 2014). Similarly, HIV infections result in high numbers of exosomes, which appears to contribute to a state of immune privilege/suppression which ultimately could lead to Acquired Immune Deficiency Syndrome (AIDS). The exosome secretion pathway is involved in the regulation of cancer homeostasis, the immune system and virion release of infected cells. In view of the foregoing, there is a need in the art for compositions and effective methods of treatment for inhibiting exosome release.

SUMMARY

One aspect of the present disclosure relates to a multipartite peptide that inhibits the release of exosomes from cells. The peptide contains at least one secretion modifying region (SMR) peptide from HIV-1 Nef and at least one Clusterin (Clu)-binding peptide (Clu-BP) and/or cell penetrating peptide (CPP).

In one embodiment, a method for treating a cancer, comprises administering to a subject in need of such treatment an effective amount of a pharmaceutical composition comprising a multipartite peptide comprising at least one secretion modifying region (SMR) peptide from HIV-1 Nef fused to at least one cell-penetrating peptide (CPP) or at least one Clusterin (Clu)-binding peptide (Clu-BP).

In one embodiment, the SMR peptide is fused to at least one CPP. In another embodiment, and SMR peptide is fused to 2, 3, 4 or 5 CPP sequences. In a particular embodiment, the peptide has an SMR peptide motif at its N-terminal end and a CPP peptide motif at its C-terminal end. In another embodiment, the peptide has a CPP peptide at its N-terminal end and an SMR peptide at its C-terminal end.

In another embodiment, the SMR peptide is fused to at least one Clu-BP. In another embodiment, the SMR peptide comprises 2, 3, 4 or 5 Clu-BP sequences. In a particular embodiment, the peptide has an SMR peptide motif at its N-terminal end and a Clu-BP peptide motif at its C-terminal end. In another embodiment, the peptide has a Clu-BP peptide at its N-terminal end and an SMR peptide at its C-terminal end.

In another embodiment, the SMR peptide comprises at least one CPP and at least one Clu-BP.

In one embodiment, the SMR peptide comprises an amino acid sequence selected from the group consisting of VGFPV (SEQ ID NO: 1), VGFPVAAVGFPV (SEQ ID NO: 2), and NXNVGFPVAAVGFPV (SEQ ID NO: 36).

In another embodiment, the at least one CPP comprises the amino acid sequence GRKKRRQRRRPPQ (SEQ ID NO: 38).

In some embodiments, the at least one Clu-BP comprises an amino acid sequence selected from the group consisting of HPLSKHPYWSQP (SEQ ID NO: 3), NTYWSQLLH-FQT (SEQ ID NO: 4) and SHALPLTWSTAA (SEQ ID NO: 5).

In one embodiment, the subject has breast cancer.

In another embodiment, the subject has leukemia.

In another embodiment, the method further comprises the step of administering to the subject a second anti-cancer agent.

In a particular embodiment, the second anti-cancer agent is paclitaxel or cisplatin.

In another embodiment, the second anti-cancer agent is a mortalin inhibitor.

In a particular embodiment, the mortalin inhibitor is MKT-077, Omeprazole or 5-(N,N-dimethyl)amiloride (DMA).

In another aspect, a polynucleotide encodes the multipartite peptide described herein.

In one embodiment, the polynucleotide is an expression vector operably linked to a regulatory sequence.

In another embodiment, a cell comprises the expression vector.

In another aspect, a pharmaceutical composition comprises an anti-cancer agent comprising at least one secretion modifying region (SMR) peptide from HIV-1 Nef fused to at least one cell-penetrating peptide (CPP) or at least one Clusterin (Clu)-binding peptide (Clu-BP).

In one embodiment, the pharmaceutical composition further comprises a second anti-cancer agent.

In a more particular embodiment, the second anti-cancer agent is selected from the group consisting of mortalin (Hsp70) inhibitors, alkylating agents, anthracycline antibiotics, anti-metabolites, detoxifying agents, interferons, polyclonal or monoclonal antibodies, EGFR inhibitors, HER2 inhibitors, histone deacetylase inhibitors, hormones or anti-hormonal agents, mitotic inhibitors, phosphatidylinositol-3-kinase (PI3K) inhibitors, Akt inhibitors, mammalian target of rapamycin (mTOR) inhibitors, proteasomal inhibitors, poly(ADP-ribose) polymerase (PARP) inhibitors, Ras/MAPK pathway inhibitors, centrosome declustering agents, multi-kinase inhibitors, serine/threonine kinase inhibitors, tyrosine kinase inhibitors, VEGF/VEGFR inhibitors, taxanes or taxane derivatives, aromatase inhibitors, anthracyclines, microtubule targeting drugs, topoisomerase poison drugs, and combinations thereof.

In another embodiment, the multipartite peptide is pegylated. In another embodiment, the multipartite peptide is incorporated into, onto, or otherwise associated with a nanoparticle. In certain particular embodiments, the nanoparticle is linked to a CPP peptide.

BRIEF DESCRIPTION OF THE DRAWINGS

The above and other objects and advantages of the application will be apparent upon consideration of the following detailed description, taken in conjunction with the accompanying figures and paragraphs. The following are brief descriptions of the drawings herein, which illustrate certain aspects and embodiments of the present application, but are not considered limiting in any way.

FIG. 5 shows that exosome-specific proteins can be detected on exosomes from MCF-7 breast cancer cells. Cells were treated for 48 hr with SMRwt peptide alone or combined with paclitaxel or cisplatin. Panel A: Expression of exosome proteins by Western blot analysis. Panel B: Exosome numbers were measured by NanoSight. Panel C: Densitometry analysis showing relative intensity of bands. Data represent the mean±SD of three independent experiments. Significant differences relative to treatment with peptide are indicated as follows: * $p<0.01$,  $p<0.001$, * $p<0.0001$.

FIG. 6 shows that exosome-specific proteins can be detected on exosomes from MDA-MB-231 breast cancer cells. Cells were treated for 48 hr with SMRwt peptide alone or combined with paclitaxel or cisplatin. Panel A shows Expression of exosome proteins by Western blot analysis. Exosome numbers were measured by NanoSight (Panel B) and densitometry analysis shows relative intensity of bands (Panel C). Data represent the mean±SD of three independent experiments. Significant differences relative to treatment with peptide are indicated as follows: * $p<0.01$,  $p<0.001$, ** $p<0.0001$.

FIG. 9, panel A shows synthetic SMRwt-CPPtat (SEQ ID NO: 39) and SMRmut-CPPtat (SEQ ID NO: 41) peptides used for the experiments depicted in FIGS. 8-14. Panel B shows synthetic SMRwt-Clu BP (SEQ ID NO: 37) and SMRmut-Clu BP (SEQ ID NO: 43) peptides used for the experiments depicted in FIGS. 8-14. The SMRwt peptide is highly conserved across all HIV-1 clades, HIV-2, and SIV. In Panel B, the peptides further include a polyethylene glycol moiety at the N-terminus, upstream of an asparagine endopeptidase cleavage site.

FIG. 11 shows that treatment of MCF-7 breast cancer cells, MDA-MB-231 breast cancer cells and K562 leukemia cells with PEG-SMRwt-Clu peptide, SMRwt-CPP peptide, or the mortalin inhibitors, MKT-077, Omeprazole or 5-(N, N-dimethyl)amiloride (DMA) antagonist blocked exosome release. Each of these three cell types were treated with PEG-SMRwt-Clu peptide, PEG-SMRmut-Clu peptide, SMRwt-CPP peptide, SMRmut-CPP peptide, MKT-077, Omeprazole or DMA for five days at 37° C. Panels A, B and C show levels of exosome release from MCF-7 cells, MDA-MB-231 cells, and K562 cells, respectively, as determined by an acetylcholinesterase (AchE) assay.

DETAILED DESCRIPTION

Figure 1:
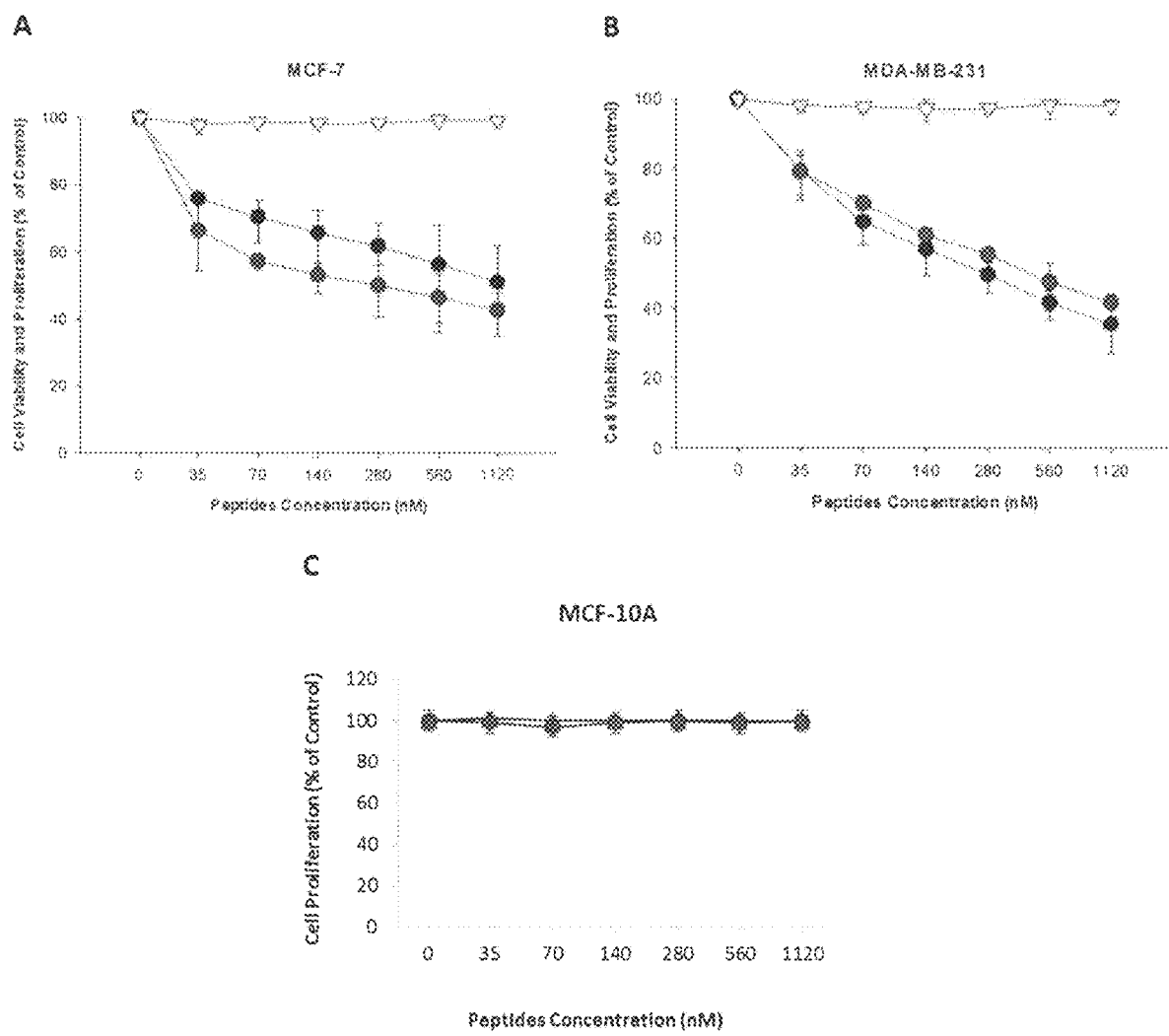
FIG. 1 shows that SMRwt peptide antagonists inhibit proliferation of MCF-7 and MDA-MB-231 breast cancer cells but not non-tumorigenic cells. Cells were incubated with peptides at varying dosage (0-1120 nM) for 24 hr, after which proliferation was measured by MTT assay. Results of three independent experiments are shown. Panel A: Proliferation of MCF-7 breast cancer cells. Panel B: Proliferation of MDA-MB-231 breast cancer cells. Panel C: Proliferation of non-tumorigenic MCF-10A cells. Lighter dots indicate PEG-SMRwt peptide, darker dots indicate PEG-SMRwt-CLU peptide, and green triangles indicate PEG-SMRmut peptide.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent or patent application publication described in this application is expressly incorporated by reference herein. Further, where the phrases "in some embodiments . . ." or "in certain embodiments . . ." are used, the present disclosure should be construed as embracing combinations of any of the features defining the different embodiments described herein, unless the features are not combinable with one another, are mutually exclusive, or are expressly disclaimed herein.

Definitions

As used herein, the terms "SMR peptide" and "SMRwt peptide" refer to a peptide less than 100 amino acids in length comprising one or more copies of the amino acid sequence, VGFPV (SEQ ID NO: 1). The term "SMRmut peptide" refer to a peptide less than 100 amino acids in length comprising one or more copies of a mutated VGFPV (SEQ ID NO: 1) peptide sequence that abolishes the functional ability of an SMRwt peptide.

As used herein, the phrase "anti-cancer agent" refers to a "small molecule drug", protein or antibody that can reduce the rate of cancer cell growth or induce or mediate the death (e.g., necrosis or apoptosis) of cancer cells in a subject (e.g., a human). The phrase "small molecule drug" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecules drugs can be derived synthetically, semi-synthetically (i.e., from naturally occurring precursors), or biologically.

As used herein, the term "nanoparticle" refers to any particle having an average diameter of less than 500 nanometers (nm). In some embodiments, nanoparticles have an average diameter of less than 300 nm, less than 100 nm, less than 50 nm, less than 25 nm, less than 10 nm or less than 5 nm. In some embodiments, each nanoparticle has a diameter of less than 300 nm, less than 100 nm, less than 50 nm, less than 25 nm, less than 10 nm or less than 5 nm.

As used herein, the terms "treat" and "treatment" refer to the amelioration of one or more symptoms associated with a disease, such as cancer or an infectious disease; prevention or delay of the onset of one or more symptoms of the disease; and/or lessening of the severity or frequency of one or more symptoms of the disease.

The term "cancer" refers to any one of a variety of malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Exemplary cancers for treatment with the methods of the instant disclosure include cancers of the brain, bladder, breast, cervix, colon, head and neck, kidney, lung, non-small cell lung, mesothelioma, ovary, prostate, stomach and uterus, leukemia, and medulloblastoma.

The term "infectious diseases" includes those pathologic conditions that arise from viruses, bacteria, fungi and/or parasites that invade and disrupt the normal function of the mammalian body. Pages 3-147 of the Merck Manual 13th Edition describe some of these conditions and they are incorporated herein by reference.

The phrases "to a patient in need thereof", "to a patient in need of treatment" or "a subject in need of treatment" includes subjects, such as mammalian subjects, that would benefit from administration of the multipartite peptide of the present disclosure for treatment of a cell proliferative disorder.

The terms "therapeutically effective amount", "pharmacologically effective amount", and "physiologically effective amount" are used interchangeably to mean the amount of a multipartite peptide that is needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein or otherwise available in the relevant literature.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

A "control individual" is an individual afflicted with the same disease as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human with a cell proliferative disorder.

A "small molecule" refers to an organic or inorganic molecule that is not a polymer, that has medicinal activity, and that has a molecular weight less than 1 kDa. The term encompasses most medicinal compounds termed "drugs" other than protein or nucleic acids, although a small molecule peptide or nucleic acid analog can be considered a "small molecule". Small molecules drugs can be derived synthetically, semi-synthetically (i.e., from naturally occurring precursors), or biologically. As used herein, the phrase "large molecule" refers to a polymeric protein- or nucleic acid-based product having a molecular weight greater than 1 kDa.

Peptides

One aspect of the present disclosure relates to a multipartite anti-cancer peptide that inhibits the release of exosomes from cells. In one embodiment, the peptide comprises at least one secretion modifying region (SMR) peptide from HIV-1 Nef and at least one Clusterin (Clu)-binding peptide (Clu-BP) or at least one cell penetrating peptide (CPP).

In some embodiments, the multipartite anti-cancer peptide has 1, 2, 3, 4 or 5 SMR peptide sequences. In particular embodiments, the SMR peptide comprises an amino acid sequence selected from the group consisting of VGFPV (SEQ ID NO: 1), VGFPVAAVGFPV (SEQ ID NO: 2), and NXNVGFPVAAVGFPV (SEQ ID NO: 36).

In one embodiment, the SMR peptide is fused to at least one Clu-BP. In another embodiment, the SMR peptide comprises 2, 3, 4 or 5 Clu-BP sequences. In a particular embodiment, the peptide has an SMR peptide motif at its N-terminal end and a Clu-BP peptide motif at its C-terminal end. In another embodiment, the peptide has a Clu-BP peptide at its N-terminal end and an SMR peptide at its C-terminal end.

In some embodiments, the at least one Clu-BP comprises an amino acid sequence selected from the group consisting of HPLSKHPYWSQP (SEQ ID NO: 3), NTYWSQLLH-FQT (SEQ ID NO: 4) and SHALPLTWSTAA (SEQ ID NO: 5) as described in U.S. Patent Publication No. 2012/0121507.

In another embodiment, the SMR peptide is fused to at least one CPP. A CPP domain enhances the uptake of the multipartite peptide into eukaryotic cells. Exemplary CPP domains for use in the present application include, but are not limited to, HIV $TAT_{49-57}$ peptide, HIV $TAT_{48-60}$ peptide (SEQ ID NO: 38), low molecular weight protamine (LMWP) peptide; Chariot®, also known as Pep-1 (Morris et al., *Nat. Biotechnol.*, 19:1173-1176, 2001); $Antp_{43-58}$ peptide, MPG (HIV Gp41-SV40 NLS), SAP, MPG R9, MAP, K-FGF, Penetratin, Buforin II, Transportan, Ku70, Prion, pVEC, Pep-1-K, Pep-7, HN-1, TP10, and CP26 (See e.g., Joliot et al., *Nature Cell Biol.*, 6(3):189-196, 2004 and Heitz et al., *Br. J. Pharmacol.*, 157:195-206, 2009).

In one embodiment, an SMR peptide is fused to 2, 3, 4 or 5 CPP sequences. In a particular embodiment, the peptide has an SMR peptide motif at its N-terminal end and a CPP peptide motif at its C-terminal end. In another embodiment, the peptide has a CPP peptide at its N-terminal end and an SMR peptide at its C-terminal end.

In a particular embodiment, the at least one CPP comprises the amino acid sequence GRKKRRQRRRPPQ (SEQ ID NO: 38).

In certain embodiments, the peptide comprises at least two SMR peptides, at least two Clu-BP peptides, and/or at least two CPP peptides. In addition, any of the peptides within an SMR peptide (e.g., SMR peptides, Clu-BP peptides, CPP peptides) may be separated by a spacer peptide.

In certain particular embodiments, the multipartite peptide comprises an amino acid sequence selected from the group consisting of VGFPVAAVGFPVHPLSKHPYWSQP (SEQ ID NO: 6), VGFPVAAVGFPVAAHPLSKHPYWSQP (SEQ ID NO: 7), VGFPVAAVGFPVAAHPLSKHYWSQ-PAAHPLSKHPYWSQP (SEQ ID NO: 8), NXNVGF-PVAAVGFPVHPLSKHPYWSQP (SEQ ID NO: 37), and VGFPVAAVGFPVGRKKRRQRRRPPQ (SEQ ID NO: 39).

In certain embodiments, the multipartite peptide of the present invention further comprises one or more spacers between one or more functional domains within the multipartite peptide. The spacer is designed to facilitate the independent folding of each domain relative to one another, ensure that the individual domains in the peptide do not interfere with one another or with the SMR peptide and/or increase the flexibility of the protein and facilitate adoption of an extended conformation. In some embodiments, the spacer comprises 1 to 50 amino acids, preferably 2 to 10 amino acids.

In some embodiments, the spacer includes one or more a glycine and/or serine residues to force the spacer to adopt a loop conformation, because the absence of a β-carbon permits the polypeptide backbone to access dihedral angles that are energetically forbidden for other amino acids. In addition, spacers comprising glycine and/or serine have a high freedom degree for linking of two peptides, i.e., they enable the fused proteins to fold and produce functional proteins. Other residues that can enhance stability and folding include the amino acids alanine, proline, lysine, and combinations thereof. In one embodiment, the spacer is an Ala-Ala dipeptide linker. In another embodiment, the spacer has the formula $[(Gly)_n\text{-Ser/Ala}]_m$ (SEQ ID NO: 35 where n is from 1 to 4, inclusive, and m is from 1 to 4, inclusive.

In some embodiments, the multipartite peptide includes a mitochondrial penetrating sequence or a mitochondrial targeting signal sequence to facilitate uptake of the multipartite peptides into the mitochondria where mortalin is localized. Exemplary mitochondrial targeting sequences include the presequence peptide described in U.S. Patent Publication 2004/0192627, including the nuclear-encoded human cytochroine c oxidase (COX) subunit VIII (MSVLTPLLL-RGLTGSARRLPVPRAKIHSL (SEQ ID NO: 9); the amino-terminal leader peptide of the rat ornithine transcarbamylase (OTC) (MLSNLRILLNKAALRKAHTSMVRNFRYGK-PVQC (SEQ ID NO: 10)), the presequence of cytochrome oxidase subunit IV (MLSLRQSIRFFKPATRTL (SEQ ID NO: 11)), and an Antennapedia α-helical domain, such as RQIKIWFQNRRMKWKK (SEQ ID NO: 12); various mitochondrial targeting peptides described in U.S. Patent Publication No. 2014/0196172, including N-terminal mitochondrial targeting peptides, MFSYLPRYPLRAASARALVRATRPSYRSALLRYQ (SEQ ID NO: 13); MAAWMRSLFSPLKKLWIRMH (SEQ ID NO: 14), MKLLWRLILSRKW (SEQ ID NO: 15), MWWRRSRTNSLRYT (SEQ ID NO: 16), and MLFRL-RRSVRLRGLLA (SEQ ID NO: 17); and the N-terminal mitochondrial targeting peptide MWTLGRRAVAGL-LASPSPAQ (SEQ ID NO: 18) as described in U.S. Patent Publication No. 2016/0237129. Exemplary mitochondrial targeting signal peptide sequences directing proteins or peptides to the mitochondria include RRIVVLHGY-GAVKEVLLNHK (SEQ ID NO: 19), amino acids 74-95 of Rat Cytochrome P450 2E (CYP2E1), the cleavable prepiece from the yeast cytochrome c oxidase IV precursor (MLSL-RQDIRFFKPATRTLCSSR (SEQ ID NO: 20)), the mitochondrial-targeting signal from the PB2 protein of influenza viruses, the import signal contained within heme lyases, and the leader peptide of the mitochondrial matrix enzyme ornithine transcarbamylase (OTC) as described in U.S. Patent Publication No. 2014/0142121.

In some embodiments, the multipartite peptide includes a cell targeting domain for targeting the peptide to specific types of cells, including tumor cells, virally-infected cells and the like. The targeting domain may comprise a peptide fused to the multipartite peptide or it may be non-peptide-based domain chemically conjugated to or covalently attached thereto. Exemplary targeting domains include a peptides, small molecules, ligands, antibody fragments, and aptamers. In addition, a targeting domain may be a small molecule (e.g., folate, adenosine, purine) or a large molecule (e.g., peptide or antibody) that specifically binds to a desired target cell of interest. In some embodiments, the targeting domain is present at the C-terminal end of the multipartite peptide. In other embodiments, the targeting domain is present at the N-terminal end of the multipartite peptide.

In some embodiments, the multipartitite peptide comprises a blood-brain barrier (BBB) entry peptide. Inclusion of a BBB entry peptide facilitates delivery of the SMR peptide into the brain for treatment of brain cancers, such as glioblastoma. Exemplary BBB entry peptides include GGGGHLNILSTLWKYRC (SEQ ID NO: 45; U.S. Patent Publ. No. 2018/0073021), TFFYGGSRGKRNNFKTEEYC (SEQ ID NO: 46; Wang et al., Scient. Rep. (2018) 8:12827), RRRRRRRR (SEQ ID NO: 47; Kamei et al., Biol. Pharm. Bull. (2018) 41:546-554), LRKLRKRLLR (SEQ ID NO: 48; McCully et al., Curr. Pharm. Design (2018) 24(13): 1366-1376), CGHKAKGPRKGKRK (SEQ ID NO: 49; McCully et al. (2018)), FKESWREARGTRIERG (SEQ ID NO: 50; McCully et al, (2018)), KSVRTWNEIIPSKGCLR (SEQ ID: 51; McCully et al, (2018)), HAIYPRH (SEQ ID NO: 52; McCully et al, (2018)), TGNYKALH-IPHNG (SEQ ID NO: 53; McCully et al, (2018)), THRPPM-WSPVWP (SEQ ID NO: 54; McCully et al, (2018)), and YTIWMPENPRPGTPCDIFTNSRGKRASNG (SEQ ID NO: 55; U.S. Patent Publ. No. 2018/0028677). Additional BBB entry peptides are described in U.S. Pat. Appl. Nos. 2011/0230416, 2012/0141416, and 2013/0108548.

In some embodiments, the multipartite peptide may be linked to an immunoglobulin Fc region. The Fc region can enhance stability and in vivo half-life and can facilitate recruitment of Fc receptor-bearing natural killer cells, macrophages, neutrophils, and mast cells, which can stimulate phagocytic or cytotoxic cells to destroy microbes or infected cells by antibody-mediated phagocytosis or antibody-dependent cell-mediated cytotoxicity. When using antibody-derived targeting agents or Fc regions, these domains are preferably "humanized" using methodologies well known to those of skill in the art.

The multipartite peptide encoded in the expression vector may further include a cleavage recognition sequence for proteolytic or an endopeptidase cleavage sequence. Incorporation of an endopeptidase cleavage recognition sequences can facilitate site specific cleavage by a suitable endopeptidase present in a eukaryotic or mammalian cell, such as asparagine endopeptidase, Factor Xa, furin, thrombin, cathepsin B, plasmin, and various matrix metalloproteinases (MMPs), such as MMP2, MMP7, MMP9, or MMP14.

In certain embodiments, placement of a suitable endopeptidase cleavage recognition sequence can serve to liberate an attached PEG moiety and/or liposomal moiety linked to the peptide, or liberate one or more peptide domains from one another so that one or more these peptide domains can function independently of one another in e.g., their targeted site.

Asparagine endopeptidase, also known as legumain, is a lysosomal cysteine protease that cleaves protein substrates on the C-terminal side of asparagine, such as Asn-Asp or Asn-Xaa-Asn. In certain embodiments, the multipartite anti-cancer peptide comprises a PEG moiety (e.g., 10 Kd) chemically conjugated to a SMR peptide via the asparagine endopeptidase cleavage sequence, NXN (PEG-NAN-SMR-CLU). Exemplary peptides conjugated to PEG via an NXN sequence include NXNVGFPVAAVGFPV (SEQ ID NO: 36) and NXNVGFPVAAVGFPVHPLSKHPYWSQP (SEQ ID NO: 37).

Sequences cleavable by MN P2, MMP7, MMP9, or MMP14 include PLGLAG (SEQ ID NO: 56), PLG-C(me)-AG (SEQ ID NO: 57), RPLALWRS (SEQ ID NO: 21), ESPAYYTA (SEQ ID NO: 22), DPRSFL (SEQ ID NO: 23), PPRSFL (SEQ ID NO: 24), RLQLKL (SEQ ID NO: 25), and RLQLK(Ac) (SEQ ID NO: 26). Cathepsin B is a tumor associated protease that can act upon the dipeptide sequences valine-citrulline and Phe-Lys. Furin cleaves the recognition sequence Arg-X-X-Arg (SEQ ID NO: 27), more preferably Arg-X-(Lys/Arg)-Arg (SEQ ID NO: 28). Factor Xa cleaves after the arginine residue in its preferred cleavage site Ile-(Glu or Asp)-Gly-Arg (SEQ ID NO: 29) and will sometimes cleave at other basic residues, depending on the conformation of the protein substrate. The most common secondary site, among those that have been sequenced, is Gly-Arg. Thrombin preferentially cleaves between Arg and Gly residues in e.g., the sequence LVPRGS (SEQ ID NO: 30).

The multipartite peptide of the present disclosure may be chemically modified using one or more methods including, but not limited to, amidation, acetylation (including N-terminal acetylation), carboxylation, glycosylation, methylation (e.g., substitution of α-hydrogens with methyl groups), carbonylation, phosphorylation, PEGylation, dimerization, addition of interchain and/or intrachain disulfide bonds, addition of trans olefin, derivatization by known protecting/blocking groups, circularization, substitution with D amino acids, linkage to an antibody molecules or other cellular ligands, etc.

The multipartite peptides of the present disclosure can be modified to contain additional nonproteinaceous moieties that are known in the art and are readily available, Preferably, the moieties suitable for derivatization of the protein are water soluble polymers. Non-limiting examples of water soluble polymers include, but are not limited to, polyethylene glycol (PEG), polyvinyl alcohol (PVA), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol (PPG) homopolymers, propylene oxide/ethylene oxide co-polymers, polyoxyethylated polyols (e.g., glycerol; POG), polyvinyl alcohol; and mixtures thereof. Polyethylene glycol propionaldehyde may have advantages in manufacturing due to its stability in water.

Additional modifications include, for example, point mutations, insertions, deletion, truncation, and backbone substitutions, such as NH to $NCH_3$, In addition, the peptide may be modified by the insertion of one or more D amino acids. Further, proline analogs in which the ring size of the proline residue is changed from 5 members to 4, 6, or 7 members can be employed. Cyclic groups can be saturated or unsaturated, and if unsaturated, can be aromatic or non-aromatic.

The multipartite peptides may include modifications to, including incorporation of any of the functional domains described herein at the N-terminal end of the peptide, the C-terminal end of the peptide, or both. Alternatively, or in addition, modifications at the N-terminal end may include an acetylated (Ac) residue and/or an amidated ($NH_2$) residue at the C-terminal end. Where the C-terminus is amidated, the carboxylic acid of the amino acid is converted to an amide, i.e., $NH_2$—$CH_2$—$C(O)$—$NH_2$.

The multipartite peptide may further contain one or more covalently attached functional groups, preferably attached to either or both of the N and C termini of the polypeptide. These covalently attached groups can include stabilizers, couplers, ligands, enzymatic substrates and/or combinations thereof. Preferred groups include acyl groups on the N terminus and cysteamine (cya) coupling groups on the C terminal end. To the latter may be conveniently attached other chemical moieties, e.g., dyes, ligands, small molecule drugs, proteins, enzymes, enzymatic substrates, etc. Alternatives to cya are also known to those of skill in the art. For stabilizing and/or blocking, e.g., cya may be replaced with an alky group such as methyl or ethyl, which are known to be conveniently positioned onto a —COOH group.

N-terminal modifications additionally may include, but are not limited to, methylation (i.e., —$NHCH_3$ or —$NH(CH_3)^2$), adding a 1-amino-cyclohexane-carboxylic acid moiety (Chex); and adding a carbobenzoyl group, or blocking the amino terminus with any blocking group containing a carboxylate functionality defined by RCOO—, where R is selected from the group consisting of naphthyl, acridinyl, steroidyl, and similar groups.

A derivitizing group, including, but not limited to, a sulfhydryl-containing group or moiety may be positioned at the C-terminus of the multipartite peptide, even when it is not coupled to another chemical moiety. In one embodiment, the C-terminal end may be modified with a cysteamide group (—NH—$CH_2$—$CH_2$—SH), which can allow further coupling to drugs. A cysteamide group is compatible with the peptide synthesis using the Fmoc strategy and leads to a C-terminal protected peptide. Alternatively, the peptide can include a C-terminal cysteine residue containing a sulfhydryl (—SH) group that can be optionally utilized for conjugation to other moieties. In another embodiment, the C-terminal end includes a 2,4-diamino-butyric acid (DAB) moiety. C-terminal modifications may further include replacing the free acid with a carboxamide group or forming a cyclic lactam at the carboxy terminus to introduce structural constraints.

Naturally occurring side chains of the 20 genetically encoded amino acids (or D amino acids) may be replaced with other side chains with similar properties, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

Such substitutions can include but are not necessarily limited to: (1) non-standard positively charged amino acids, like: ornithine; N-(4-aminobutyl)-glycine having a lysine side chain attached to the "N-terminus" and aminopropyl or aminoethyl groups attached to the amino group of glycine; (2) Non-naturally occurring amino acids with no net charge and sidechains similar to arginine, such as citrulline, with or without methylene groups; (3) non-standard non-naturally occurring amino acids with OH (e.g., serine), such as, homoserine, hydroxyproline, hydroxyvaline, and penicillamin; (4) proline derivatives, such as, D-Pro, including 3,4-dehydroproline, pyroglutamine, proline with fluorine substitutions on the ring, 1,3-thiazolidine-4-carboxylic acid; (5) Histidine derivative, such as beta-(2-thienyl)-alanine; or (6) alkyl derivatives, such as 2-aminobutyric acid, norvaline, norleucine, homoleucine, and alpha-aminoisobutyric acid.

In other embodiments, the C-terminal carboxyl group or a C-terminal ester may be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

In other embodiments, the multipartite peptide of the present disclosure is cyclized or includes a desamino or descarboxy residue at the peptide termini so that there are no terminal amino or carboxyl groups. This can decrease susceptibility to proteases and/or to restrict the conformation of the peptide. C-terminal functional groups of the compounds of the present disclosure include amide, amide lower alkyl, amide di(lower alkyl), lower alkoxy, hydroxy, and carboxy, and the lower ester derivatives thereof, and the pharmaceutically acceptable salts thereof. The multipartite peptide may be cyclized by adding an N and/or C terminal cysteine and cyclizing the peptide through disulfide linkages or other side chain interactions.

In one preferred embodiment, the multipartite peptide (or pharmaceutical composition thereof) has the structure A-B-C-D/E, where A is a PEG, such as a 10 kD PEG; B is a peptide cleavage linker sequence for an endopeptidase, such as asparagine endopeptidase; C is an SMR-containing peptide sequence, such as VGFPVAAVGFPV (SEQ ID NO: 2); D is a Clu-BP peptide sequence, such as HPLSKHPYWSQP (SEQ ID NO: 3); and E is a cell penetrating peptide (CPP) sequence, such as GRKKRRQRRRPPQ (SEQ ID NO: 38).

The multipartite peptides of the present disclosure may be administered as naked peptides with or without PEG moieties, or they may be incorporated into, onto, or otherwise associated with a suitable carrier, such as a liposome, nanoparticle, hydrogel, polymeric micelle, microcapsule, virus, bacteriophage, or virus-like particle (VLP).

Exemplary nanoparticles include paramagnetic nanoparticles, superparamagnetic nanoparticles, metal nanoparticles, polymeric nanoparticles, nanoworms, nanoemulsions, nanogels, fullerene-like materials, inorganic nanotubes, dendrimers (such as with covalently attached metal chelates), nanocapsules, nanospheres, nanofibers, nanohoms, nanoonions, nanorods, nanoropes and quantum dots. A nanoparticle can produce a detectable signal, for example, through absorption and/or emission of photons (including radio frequency and visible photons) and plasmon resonance. Nanoparticles can be biodegradable or non-biodegradable.

In certain embodiments, the nanoparticle is a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199.

In other embodiments, a polymeric nanoparticle is made from a synthetic biodegradable polymer, a natural biodegradable polymer or a combination thereof. Synthetic biodegradable polymers can include, polyesters, such as poly (lactic-co-glycolic acid)(PLGA) and polycaprolactone; polyorthoesters, polyanhydrides, polydioxanones, poly-alkyl-cyano-acrylates (PAC), polyoxalates, polyiminocarbonates, polyurethanes, polyphosphazenes, or a combination thereof. Natural biodegradable polymers can include starch, hyaluronic acid, heparin, gelatin, albumin, chitosan, dextran, or a combination thereof.

In certain particular embodiments, the above-described carriers, including nanoparticles, may be linked to the CPP peptides, targeting peptides, mitochondrial targeting peptides, and/or BBB entry peptides described herein to facilitate carrier-mediated delivery of the active agents described herein.

Peptide-Encoding Polynucleotides

Another aspect of the present disclosure relates to a polynucleotide encoding any of the multipartite peptides described herein. In one embodiment, the polynucleotide is an expression vector. As used herein, the term "expression vector" refers to a non-viral or a viral vector that comprises a polynucleotide encoding the multipartite peptide of the present disclosure in which the peptide coding sequences are operably linked to regulatory sequences sufficient for expressing the peptide in a cell. One type of non-viral vector is a "plasmid", which includes a circular double-stranded DNA loop into which additional DNA segments can be ligated. In the present specification, "plasmid" and "vector" can be used interchangeably as the plasmid is the most commonly used form of vector.

The regulatory sequences may be selected on the basis of the host cells to be used for expression, such that the design of the expression vector and inclusion of regulatory sequences depends on such factors as the choice of the host cell to be transformed, the level of expression of protein desired, whether the peptide is to be secreted into the extracellular milieu and the like. The expression vectors of the invention can be introduced into host cells to direct the expression of the multipartite peptide of the present disclosure in vitro for production purposes or in vivo for therapeutic purposes.

As used herein, the terms "control sequences" or "regulatory sequences" refer to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences).

A nucleic acid sequence is "operably linked" to another nucleic acid sequence when the former is placed into a functional relationship with the latter. For example, in certain embodiments, the expression vector encodes a pre-sequence or signal peptide that is operably linked to the peptide coding sequences for expression as a preprotein that participates in the secretion of the polypeptide. In addition, a promoter or enhancer is said to be operably linked to a coding sequence if it affects the transcription of the sequence and a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking these sequences may be accomplished by ligation at convenient restriction sites or by the use of synthetic oligonucleotide adaptors, primers, and/or linkers are used in accordance with conventional practices in the art.

In certain cases, these vectors may be engineered to target certain diseases or cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In certain embodiments, the expression vector is engineered to direct expression of the peptide ubiquitously or preferentially in a particular cell type (e.g., tissue-specific regulatory elements are used to express the polynucleotide). Thus, in certain embodiments, expression of the peptide is under the control of a tissue specific or ubiquitous promoter, such as the CMV promoter or a CMV-chicken beta-actin hybrid (CAG) promoter. In other embodiments, a tissue specific or tumor-specific promoter may be used. Exemplary tissue-specific regulatory elements are known in the art and may include liver-specific promoter (e.g., albumin promoter), lymphoid-specific promoters, epithelial cell-specific promoters, promoters of T cell receptors and immunoglobulins, neuron-specific promoters (e.g., the neurofilament promoter), pancreas-specific promoters (e.g., insulin promoter), and mammary gland-specific promoters (e.g., milk whey promoter). Developmentally-regulated promoters (e.g., the α-fetoprotein promoter) are also encompassed.

In certain embodiments, the multipartite expression construct may be linked to a mitochondrial targeting peptide or leader sequence to facilitate uptake of the expression construct into mitochondrial cells as described in U.S. Patent Publication No. 20040192627. Conventional protocols may be used to conjugate the expression construct with the mitochondrial targeting peptide, e.g., pGeneGrip™ technology (Genlantis/Gene Therapy Systems. Inc., San Diego, Calif.). Alternatively, the multipartite peptide coding sequence may be fused to a mitochondrial targeting sequence to direct translocation of the expressed peptide into mitochondria as described above.

In other embodiments, the multipartite peptide coding sequence may be fused to a mitochondrial penetrating moiety or mitochondrial targeting signal sequence as described above. Exemplary nucleic acids that act as mitochondrial penetrating moieties (such as those described in U.S. Pat. No. 5,569,754) include e.g., CCGCAAGAAGCG (SEQ ID NO: 31), GCGTGCACACGCGCGTAGACTTCCCCCGCAAGTCACTCGTTAGCCCGCCAAGAAGC GACCCCTCCGGGGCGAGCTGAGCGGCGTG-GCGCGGGGGCGTCAT (SEQ ID NO: 32), ACGTGCATACGCACGTAGACATCCCCGCTITCCCACTCCAAAGTCCGCCAAGAAGCG TATCCCGCTGAGCGGCGTGGCGCGGGGCGT-CATCCGTCAGCTC (SEQ ID NO: 33) or ACTICCCCCG-CAAGTCACTCGTTAGCCCGCCAAGAAGCGAC-CCCTCCGGGGCGAGCTG (SEQ ID NO: 34).

In some embodiments, the multipartite peptide coding sequence may be fused to a signal peptide domain for secretion of the peptide from cells expressing the peptide. The signal peptide sequence is removed from the mature peptide as the mature peptide is secreted from the cell. Since a given signal peptide sequence can affect the level of peptide expression, a peptide-encoded polynucleotide may include any one of a variety of different N-terminal signal peptide sequences known in the art.

In some embodiments, the expression vector is a viral vector. A viral vectors may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a "naked" expression vector that is not packaged with virally derived components (e.g., capsids and/or envelopes).

Non-viral expression vectors can be utilized for non-viral gene transfer, either by direct injection of naked DNA or by encapsulating the multipartite peptide-encoding polynucleotides in liposomes, nanoparticles, hydrogels, microcapsules, or virus-like particles. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

Pharmaceutical Compositions

In some embodiments, a pharmaceutical composition comprises a multipartite peptide comprising at least one SMR peptide from HIV-1 Nef, at least one Clusterin (Clu)-binding peptide (Clu-BP) and a pharmaceutically acceptable carrier. In addition, the multipartite peptide may include any of the above described modification.

In another embodiment, a pharmaceutical composition comprises an expression vector encoding a multipartite peptide comprising at least one SMR peptide from HIV-1 Nef, at least one Clusterin (Clu)-binding peptide (Clu-BP) and a pharmaceutically acceptable carrier, whereby the encoded peptide is designed to include any of the above described modifications.

As used herein, the term "pharmaceutically acceptable" refers to a molecular entity or composition that does not produce an adverse, allergic or other untoward reaction when administered to an animal or a human, as appropriate. The term "pharmaceutically acceptable carrier", as used herein, includes any and all solvents, solubilizers, fillers, stabilizers, surfactants, binders, absorbents, bases, buffering agents, excipients, lubricants, controlled release vehicles, diluents, emulsifying agents, humectants, lubricants, gels, dispersion media, coatings, antibacterial or antifungal agents, isotonic and absorption delaying agents, and the like, compatible with pharmaceutical administration. The use of such carriers and agents for pharmaceutically active substances is well-known in the art. See e.g., A. H. Kibbe Handbook of Pharmaceutical Excipients, 3rd ed. Pharmaceutical Press, London, UK (2000).

Exemplary carriers or excipients include but are not limited to, calcium carbonate, calcium phosphate, various sugars, starches, cellulose derivatives, gelatin, polymers such as polyethylene glycols, water, saline, isotonic aqueous solutions, phosphate buffered saline, dextrose, 0.3% aqueous glycine, glycerol, ethanol and the like, as well as combinations thereof. In many cases, it will be preferable to include isotonic agents, for example, sugars, polyalcohols such as mannitol, sorbitol, or sodium chloride in the composition, or glycoproteins for enhanced stability, such as albumin, lipoprotein and globulin. Pharmaceutically acceptable carriers may further comprise minor amounts of auxiliary substances such as wetting or emulsifying agents, preservatives or buffers, which enhance the shelf life or effectiveness of the therapeutic agents. In certain embodiments, the pharmaceutically acceptable carrier comprises serum albumin.

Formulation characteristics that can be modified include, for example, pH and osmolality. For example, it may be desired to achieve a formulation that has a pH and osmolality similar to that of human blood or tissues to facilitate the formulation's effectiveness when administered parenterally.

Buffers are useful in the present invention for, among other purposes, manipulation of the total pH of the pharmaceutical formulation (especially desired for parenteral administration). A variety of buffers known in the art can be used in the present formulations, such as various salts of organic or inorganic acids, bases, or amino acids, and including various forms of citrate, phosphate, tartrate, succinate, adipate, maleate, lactate, acetate, bicarbonate, or carbonate ions. Particularly advantageous buffers for use in parenterally administered forms of the presently disclosed compositions in the present invention include sodium or potassium buffers, including sodium phosphate, potassium phosphate, sodium succinate and sodium citrate.

Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%).

In one embodiment, sodium phosphate is employed in a concentration approximating 20 mM to achieve a pH of approximately 7.0. A particularly effective sodium phosphate buffering system comprises sodium phosphate monobasic monohydrate and sodium phosphate dibasic heptahydrate. When this combination of monobasic and dibasic sodium phosphate is used, advantageous concentrations of each are about 0.5 to about 1.5 mg/ml monobasic and about 2.0 to about 4.0 mg/ml dibasic, with preferred concentrations of about 0.9 mg/ml monobasic and about 3.4 mg/ml dibasic phosphate. The pH of the formulation changes according to the amount of buffer used.

Depending upon the dosage form and intended route of administration it may alternatively be advantageous to use buffers in different concentrations or to use other additives to adjust the pH of the composition to encompass other ranges. Useful pH ranges for compositions of the present invention include a pH of about 2.0 to a pH of about 12.0.

In some embodiments, it will also be advantageous to employ surfactants in the presently disclosed formulations, where those surfactants will not be disruptive of the drug-delivery system used. Surfactants or anti-adsorbants that prove useful include polyoxyethylenesorbitans, polyoxyethylenesorbitan monolaurate, polysorbate-20, such as Tween-20™, polysorbate-80, polysorbate-20, hydroxycellulose, genapol and BRIJ surfactants. By way of example, when any surfactant is employed in the present invention to produce a parenterally administrable composition, it is advantageous to use it in a concentration of about 0.01 to about 0.5 mg/ml.

Additional useful additives are readily determined by those of skill in the art, according to particular needs or intended uses of the compositions and formulator. One such particularly useful additional substance is sodium chloride, which is useful for adjusting the osmolality of the formulations to achieve the desired resulting osmolality. Particularly preferred osmolalities for parenteral administration of the disclosed compositions are in the range of about 270 to about 330 mOsm/kg. The optimal osmolality for parenterally administered compositions, particularly injectables, is approximately 300 mOsm/kg and achievable by the use of sodium chloride in concentrations of about 6.5 to about 7.5 mg/ml with a sodium chloride concentration of about 7.0 mg/ml being particularly effective.

Multipartite peptides can be stored as a lyophilized powder under aseptic conditions and combined with a sterile aqueous solution prior to administration. The aqueous solution used to resuspend the peptides can contain pharmaceutically acceptable auxiliary substances as required to approximate physical conditions, such as pH adjusting and buffering agents, tonicity adjusting agents and the like, as discussed above. Alternatively, the multipartite peptides can be stored as a suspension, preferable an aqueous suspension, prior to administration.

In certain preferred embodiments, the multipartite peptide in the pharmaceutical composition is pegylated. PEGylation is a process for covalently attaching polyethylene glycol polymer chains to another molecule, normally a drug or therapeutic peptide/protein. PEGylation can be achieved by incubation of a reactive derivative of PEG with the multipartite peptide. The covalent attachment of PEG to a multipartite peptide can "mask" the multipartite peptide from the host's immune system (reduced immunogenicity and antigenicity), increase the hydrodynamic size (size in solution) of the multipartite peptide which prolongs its circulatory time by reducing renal clearance. PEGylation can also provide water solubility to hydrophobic proteins.

The PEG molecules are typically characterized as having for example from about 2 to about 1000, or from about 2 to about 300 repeating units. For example water-soluble polymers, including but not limited to PEG, poly(ethylene oxide) (PEO), polyoxyethylene (POE), polyvinyl alcohols, hydroxyethyl celluloses, or dextrans, are commonly conjugated to proteins to increase stability or size, etc., of the protein as described in U.S. Patent Publication No. 2012/0171115.

PEG, PEO and POE are oligomers or polymers of ethylene oxide. In the case of PEG, these oligomers or polymers are produced by, e.g., anionic ring opening polymerization of ethylene oxide initiated by nucleophilic attack of a hydroxide ion on the epoxide ring. One of the more useful forms of PEG for protein modification is monomethoxy PEG (mPEG).

Preferred PEGs are monodisperse or polydisperse, preferably monodisperse. The skilled artisan will be aware that PEG can be polydisperse or monodisperse. Polydisperse PEG comprises a mixture of PEGs having different molecular weights. In the case of polydisperse PEGs, reference to a specific molecular weight will be understood to refer to the number average molecular weight of PEGs in the mixture. The size distribution is characterized statistically by its weight average molecular weight (MW) and its number average molecular weight (Mn), the ratio of which is called the polydispersity index (Mw/Mn). MW and Mn are measured, in certain aspects, by mass spectroscopy. Most of the PEG-protein conjugates, particularly those conjugated to PEG larger than 1 KD, exhibit a range of molecular weights due to a 30 polydisperse nature of the parent PEG molecule. For example, in case of mPEG2K (Sunbright ME-020HS, NOF), actual molecular masses are distributed over a range of 1.5-3.0 KD with a polydispersity index of 1.036. Based on the foregoing, the skilled artisan will be aware that monodisperse PEG comprises a mixture of PEGs comprising substantially the same molecular weight. Monodisperse PEGs are commercially available, e.g., from Polypure AS, Norway.

The average or preferred molecular weight of the PEG may range from 500 Da to 200 kDa, from 1 to 100 kDa, from 2 to 50 kDa, from 5 to 25 kDa, or from 5 kDa to 10 kDa, including any integers encompassed within these ranges.

The choice of the suitable functional group for the PEG derivative is based on the type of available reactive group on the molecule that will be coupled to the PEG. For peptides or proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers.

In certain embodiments, the PEG derivatives are produced by reacting the PEG polymer with a group that is reactive with hydroxyl groups, typically anhydrides, acid chlorides, chloroformates and carbonates. In other embodiments, more efficient functional groups such as aldehyde, esters, amides, etc. are made available for protein conjugation.

In certain embodiments, heterobifunctional PEGs are used for conjugation. These heterobifunctional PEGs are useful for linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters. In other embodiments, the pegylation agents contain branched, Y shaped or comb shaped polymers that show reduced viscosity and lack of organ accumulation.

Various methods are known in the art for conjugating PEGs to peptides or proteins, as describe in U.S. Patent Publication No. 2012/0171115. Conjugation of PEGs may include the use of spacer moieties that are cleavable or non-cleavable. In some embodiments, the cleavable spacer moiety is a redox-cleavable spacer moiety, such that the spacer moiety is cleavable in environments with a lower redox potential, such the cytoplasm and other regions with higher concentrations of molecules with free sulfhydryl groups. Examples of spacer moieties that may be cleaved due to a change in redox potential include those containing disulfides. The cleaving stimulus can be provided upon intracellular uptake of the conjugated protein where the lower redox potential of the cytoplasm facilitates cleavage of the spacer moiety. In the case of PEG, the molecule can be activated to facilitate its binding to amines or imidazoles, a carboxylic group, a hydroxyl group or a sulfhydryl group.

In another example, a decrease in pH causes cleavage of the spacer to thereby release of the compound into a target cell. A decrease in pH is implicated in many physiological and pathological processes, such as endosome trafficking, tumour growth, inflammation, and myocardial ischemia. The pH drops from a physiological 7.4 to 5-6 in endosomes or 4-5 in lysosomes. Examples of acid sensitive spacer moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, U.S. Pat. Nos. 4,569,789, 4,631,190, 5,306,809, and 5,665,358). Other exemplary acid-sensitive spacer moieties comprise dipeptide sequences Phe-Lys and Val-Lys.

Cleavable spacer moieties may be sensitive to biologically supplied cleaving agents that are associated with a particular target cell, for example, lysosomal or tumor-associated enzymes. Examples of linking moieties that can be cleaved enzymatically include, but are not limited to, esters and endopeptidase cleavage recognition sites.

An activated PEG may be used with cyanuric chloride to produce a PEG dichlorotriazine derivative. This derivative can react with multiple functional nucleophilic functional groups, such as lysine, serine, tyrosine, cysteine and histidine. Two widely used forms of PEG used to conjugate to proteins are succinimidyl carbonate PEG and benzotriazole carbonate PEG (BTC-PEG; U.S. Pat. No. 5,560,234). Both of these compounds react preferentially with lysine residues to form carbamate linkages, however are also known to react with hystidine and tyrosine. SC-PEG is slightly more resistant to hydrolysis than BTC-PEG.

Another PEG useful for conjugating to proteins is PEG-propionaldehyde (U.S. Pat. No. 5,252,714). An advantage of this chemistry is that under acidic conditions (about pH5) it is largely selective for N-terminal $\alpha$-amine thus avoiding potential problems with non-specific conjugation. An acetal derivative of PEG-propionaldehyde, i.e., PEG-acetaldehyde provides an additional benefit in so far as it provides for longer storage than PEG-propionaldehyde (U.S. Pat. No. 5,990,237).

Active esters of PEG carboxylic acids are probably one of the most used acylating agents for protein conjugation. Active esters react with primary amines near physiological conditions to form stable amides. Activation of PEG-carboxylic acids to succinimidyl active esters is accomplished by reacting the PEG-carboxylic acid with N-hydroxysuccinimide (NHS or HOSu) and a carbodiimide. Exemplary carboxylic acid derivatives of PEG include carboxymethylated PEG (CM-PEG), butanoic acid derivatives and propionic acid derivatives (U.S. Pat. No. 5,672,662). Changing the distance between the active ester and the PEG backbone by the addition of methylene units can dramatically influence reactivity towards water and amines (e.g., by reducing hydrolysis). Alternatively or in addition, hydrolysis can be reduced by introducing an .alpha.-branching moiety to the carboxylic acid.

PEGylation of free cysteine residues in a protein is useful for site-specific conjugation (e.g., using a protein modified to include cysteine residues as described herein). Exemplary PEG derivatives for cysteine conjugation include PEG-maleimide, PEG-vinylsulfone, PEG-iodoacetamide and PEG-orthopyridyl disulfide. Exemplary methods for conjugating PEG to cysteine residues and for conjugation using PEG-vinylsulfone are well known in the art.

U.S. Pat. No. 5,985,263 describes methods for conjugating PEG to the secondary amine group of histidine, which has a lower pKa than the primary amine. An advantage of this approach is that the acyl-histidine bond is not stable meaning that the peptide or protein is slowly released (i.e., the conjugate behaves as a slow release formulation or a pro-drug).

Another approach for PEGylation is to take advantage of a N-terminal serine or threonine, which can be converted to periodate as discussed above. Using this approach, PEG has been conjugated to bioactive proteins (e.g., Gaertner and Offord, 1996). PEG can also be conjugated to carbohydrate groups.

The pharmaceutical composition of the present disclosure is formulated to be compatible with its intended route of administration. Examples of routes of administration include parenteral, e.g., intrathecal, intra-arterial, intravenous, intradermal, subcutaneous, oral, transdermal (topical) and transmucosal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the multipartite peptide in the required amount in an appropriate solvent with one or a combination of ingredients enumerated above, as required, followed by filtered sterilization. Generally, dispersions are prepared by incorporating the multipartite peptide into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active peptide plus any additional desired ingredient from a previously sterile-filtered solution thereof.

Oral compositions generally include an inert diluent or an edible carrier. They can be enclosed in gelatin capsules or compressed into tablets. The tablets, pills, capsules, troches and the like can contain any of the following ingredients, or compounds of a similar nature, including a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the peptides are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for controlled or delayed release of the active ingredient. For example, in certain embodiments, the peptides may be delivered from with an enteric coating applied as a barrier to an oral formulation so as to prevent release of the peptides before they reach the small intestine. As used herein, the term "enteric coating" is a coating comprising of one or more polymers having a pH dependent or pH-independent release profile. An enteric coated pill will not dissolve in the acidic juices of the stomach (pH~3), but they will in the alkaline (pH 7-9) environment present in the small intestine or colon. An enteric polymer coating typically resists releases of the active agents until sometime after a gastric emptying lag period of about 3-4 hours after administration.

Such enteric coatings or barrier coatings are also used to protect acid-unstable peptides from the stomach's acidic exposure, delivering them instead to a basic pH environment (intestine's pH 5.5 and above) where they do not degrade and can mediate their desired action. An oral formulation may comprise a plurality of barrier coatings comprising a variety of different materials to facilitate release in a temporal manner. The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone) or a coating based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, the formulation may additionally include a time delay material such as glyceryl monostearate or glyceryl distearate.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to tumor antigens or viral antigens) can also be used as pharmaceutically acceptable carriers.

It is especially advantageous to formulate the peptide compositions in dosage unit form for ease of administration and uniformity of dosage. Suitable unit dosage forms include, but are not limited to powders, tablets, pills, capsules, lozenges, suppositories, patches, nasal sprays, injectibles, implantable sustained-release formulations, lipid complexes, etc.

Methods of Treatment

In another aspect, the present disclosure provides methods for treating cancers and infectious diseases. In some embodiments, the present application relates to a method for treating cancer. The method comprises the step of administering to a subject in need thereof an effective amount of a pharmaceutical composition comprising a multipartite peptide containing at least one secretion modifying region (SMR) peptide from HIV-1 Nef and at least one Clusterin (Clu)-binding peptide (Clu-BP). The subject may have a cancer selected from the group consisting of leukemia, lymphoma, carcinoma, melanoma, sarcoma, germ cell tumor and blastoma.

As used herein, the term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "lymphoma" refers to a group of blood cell tumors that develop from lymphocytes. Exemplary lymphomas include, for example, Hodgkin's lymphomas (HL) and the non-Hodgkin lymphomas.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, pre-malignant skin lesions, testicular cancer, thyroid cancer, neuroblastoma, esophageal cancer, genitourinary tract cancer, malignant hypercalcemia, cervical cancer, endometrial cancer, and adrenal cortical cancer. In one embodiment, the subject has breast cancer.

In other embodiments, the present application relates to a method for treating an infectious disease. The method comprises the step of administering to a subject in need thereof an effective amount of a pharmaceutical composition comprising a multipartite peptide containing at least one secretion modifying region (SMR) peptide from HIV-1 Nef and at least one Clusterin (Clu)-binding peptide (Clu-BP).

In some embodiments, the infectious disease is caused by a bacterium. In some embodiments, the infectious disease is caused by a fungus, In some embodiments, the infectious disease is caused by a parasite.

In some embodiments, the infectious disease is caused by a virus selected from the group consisting of human immunodeficiency virus type 1 and type 2 (HIV-1 and HIV-2), human T-cell lymphotropic virus type I and type II (HTLV-I and HTLV-II), hepatitis A virus, hepatitis B virus (HBV), hepatitis C virus (HCV), hepatitis delta virus (HDV), hepatitis E virus (HEV), hepatitis G virus (HGV), parvovirus B19 virus, hepatitis A virus, hepatitis G virus, hepatitis E virus, transfusion transmitted virus (TTV), Epstein-Barr virus, human cytomegalovirus type 1 (HCMV-1), human herpesvirus type 6 (HHV-6), human herpesvirus type 7 (HHV-7), human herpesvirus type 8 (HHV-8), influenza type A viruses, including subtypes H1N1 and H5N1, human metapneumovirus, severe acute respiratory syndrome (SARS) coronavirus, hantavirus, and RNA viruses from Arenaviridae (e.g., Lassa fever virus (LFV)), Pneumoviridae (e.g., human metapneumovirus), Filoviridae (e.g., Ebola virus (EBOV), Marburg virus (MBGV) and Zika virus); Bunyaviridae (e.g., Rift Valley fever virus (RVFV), Crimean-Congo hemorrhagic fever virus (CCHFV), and hantavirus); Flaviviridae (West Nile virus (WNV), Dengue fever virus (DENV), yellow fever virus (YFV), GB virus C (GBV-C; formerly known as hepatitis G virus (HGV)); Rotaviridae (e.g., rotavirus), and combinations thereof. In one embodiment, the subject is infected with HIV-1 or HIV-2.

Combination Therapies

In certain embodiments, the SMR peptides of the present application are combined with one or more additional anti-cancer agents. The anti-cancer agent may be a mortalin (Hsp70) inhibitor; an alkylating agent; an anthracycline antibiotic; an anti-metabolite; a detoxifying agent; an interferon; a polyclonal or monoclonal antibody; an EGFR inhibitor; a HER2 inhibitor; a histone deacetylase inhibitor; a hormone or anti-hormonal agent; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue or combination thereof.

Exemplary mortalin (Hsp70) inhibitors include, but are not limited to, MKT-077 (1-Ethyl-2-[[3-ethyl-5-(3-methyl-2(3H)-benzothiazolylidene)-4-oxo-2-thiazolidinylidene]methyl]-pyridinium chloride), Omeprazole (5-Methoxy-2-[[(4-methoxy-3,5-dimethyl-2-pyridinyl)methyl]sulfinyl]-1H-benzimidazole), 5-(N,N-Dimethyl)amiloride (DMA), 2-phenylethynesulfonamide (PES), JG-98 (Li et al., ACS Med. Chem. Lett., (2013)4:1042-1047). Additional mortalin inhibitors are described in U.S. Pat. No. 9,642,843 and U.S. Patent Publication Nos. 2012/0252818, 2017/0014434, and 2018/0002325.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary anthracycline antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) and ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone deacetylase inhibitors include, but are not limited to, vorinostat (Zolinza), valproic acid, romidepsin, entinostat abexinostat, givinostat, and mocetinostat.

Exemplary hormonal or anti-hormonal agents include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); abiraterone acetate (Zytiga); leuprorelin (Lupron); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary phosphatidyl-inositol-3 kinase (PI3K) inhibitors include wortmannin an irreversible inhibitor of PI3K, demethoxyviridin a derivative of wortmannin, LY294002, a reversible inhibitor of PI3K; BKM120 (Buparlisib); Idelalisib (a PI3K Delta inhibitor); duvelisib (IPI-145, an inhibitor of PI3K delta and gamma); alpelisib (BYL719), an alpha-specific PI3K inhibitor; TGR 1202 (previously known as RP5264), an oral PI3K delta inhibitor; and copanlisib (BAY 80-6946), an inhibitor PI3Kα,δ isoforms predominantly.

Exemplary Akt inhibitors include, but are not limited to miltefosine, AZD5363, GDC-0068, MK2206, Perifosine, RX-0201, PBI-05204, GSK2141795, and SR13668.

Exemplary MTOR inhibitors include, but are not limited to, everolimus (Afinitor) or temsirolimus (Torisel); rapamune, ridaforolimus; deforolimus (AP23573), AZD8055

(AstraZeneca), OSI-027 (OSI), INK-128, BEZ235, PI-103, Torin1, PP242, PP30, Ku-0063794, WAY-600, WYE-687, WYE-354, and CC-223.

Exemplary proteasomal inhibitors include, but are not limited to, bortezomib (PS-341), ixazomib (MLN 2238), MLN 9708, delanzomib (CEP-18770), carfilzoinib (PR-171), YUIO1, oprozomib (ONX-0912), marizomib (NPI-0052), and disufiram.

Exemplary PARP inhibitors include, but are not limited to, olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof.

Exemplary Ras/MAPK pathway inhibitors include, but are not limited to, trametinib, selumetinib, cobimetinib, CI-1040, PD0325901, AS703026, RO4987655, RO5068760, AZD6244, GSKI 120212, TAK-733, U0126, MEK162, and GDC-0973.

Exemplary centrosome declustering agents include, but are not limited to, griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof; CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, and N2-benzyl-5-nitro-2-furamide.

Exemplary multi-kinase inhibitors include, but are not limited to, regorafenib; sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent) trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxel.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); and mimosine (Leucenol).

These additional chemotherapeutic agents may be loaded into liposomes with the SMR peptides of the present application, in separate liposomal formulations co-administered with the SMR peptides, or by other modes of administration as otherwise employed (e.g., oral administration, i.v. injection etc.).

In certain particular embodiments, the SMR peptides of the present application are combined with one or more mortalin inhibitors.

Dosages and Routes of Administration

Depending on the nature of the disease target, the multipartite peptides of the present disclosure may be administered by any route, including but not limited to any of the various parenteral, gastrointestinal, inhalation, and topical (epicutaneous) routes of administration. Parenteral administration generally involves injections or infusions and includes, for example, intravenous, intraarterial, intratumoral, intracardiac, intramuscular, intravesicular (e.g., to the bladder), intracerebral, intracerebroventricular, intraosseous infusion, intravitreal, intaarticular, intrathecal, epidural, intradermal, subcutaneous, transdermal, and intraperitoneal administration. Gastrointestinal administration includes oral, buccal, sublingual and rectal administration. The route of administration may involve local or systemic delivery of the multipartite peptides.

As a general proposition, the therapeutically effective amount of the multipartite peptide administered will be in the range of about 1 ng/kg body weight/day to about 100 mg/kg body weight/day whether by one or more administrations. In a particular embodiment, the range of multipartite peptide administered is from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 µg/kg body weight/day, 1 µg/kg body weight/day to about 10 µg/kg body weight/day, 1 µg/kg body weight/day to about 100 µg/kg body weight/day, 10 µg/kg body weight/day to about 100 µg/kg body weight/day, 10 µg/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day.

In other embodiments, the multipartite peptide is administered at a dosage range of 1 ng-10 ng per injection, 10 ng-100 ng per injection, 100 ng-1 µg per injection, 1 µg-10 µg per injection, 10 µg-100 µg per injection, 100 µg-1 mg per injection, 1 mg-10 mg per injection, 10 mg-100 mg per injection, and 100 mg-1000 mg per injection. The multipartite peptide may be injected daily, or every 2, 3, 4, 5, 6 and 7 days.

In other embodiments, the dose range of the multipartite peptide administered is from about 1 ng/kg to about 100 mg/kg. In still another particular embodiment, the range of antibody administered is from about 1 ng/kg to about 10 ng/kg, about 10 ng/kg to about 100 ng/kg, about 100 ng/kg to about 1 µg/kg, about 1 µg/kg to about 10 µg/kg, about 10 µg/kg to about 100 µg/kg, about 100 µg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of multipartite peptide administered is, or is about, 0.0006, 0.001, 0.003, 0.006, 0.01, 0.03, 0.06, 0.1, 0.3, 0.6, 1, 3, 6, 10, 30, 60, 100, 300, 600 and 1000 mg/day.

The specific dose of multipartite peptide is determined by the particular circumstances of the individual patient including the size, weight, age and sex of the patient, the nature and stage of the disease, the aggressiveness of the disease, and the route of administration of the pharmaceutical composition.

In certain embodiments, the multipartite peptide may be administered at least once per day, typically once, twice, three times or four times per day with the doses given at equal intervals throughout the day and night in order to maintain a constant presence of the drug in order to provide sufficient efficacy. However, a skilled artisan will appreciate that a treatment schedule can be optimized for any given patient, and that administration of compound may occur less frequently than once per day.

Dosage unit form as used herein includes physically discrete units suited as unitary dosages for the subject to be treated; each unit containing a predetermined quantity of the multipartite peptide calculated to produce the desired therapeutic effect in association with the required pharmaceutical carrier. The specification for the dosage unit forms of the invention are dictated by and directly dependent on the unique characteristics of the multipartite peptide and the particular therapeutic effect to be achieved.

Toxicity and therapeutic efficacy of the multipartite peptide of the present disclosure can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Peptides exhibiting large therapeutic indices are preferred. While peptides that exhibit toxic side effects may be used, care should be taken to design a delivery system that targets such peptides to the site of affected tissue in order to minimize potential damage to non-diseased cells and, thereby, reduce side effects.

Data obtained from the cell culture assays and animal studies can be used in formulating a range of dosage for use in humans. The dosage of such peptides lies preferably within a range of circulating concentrations that include the ED50 with little or no toxicity. The dosage may vary within this range depending upon the dosage form employed and the route of administration utilized. For any peptide used in the methods of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

When treating a cancer, any of the multipartite peptides of the present disclosure may be prescribed to be taken in combination with one or more other anti-cancer agents. When used in such combination therapies, the multipartite peptides of the present disclosure and other pharmaceutical agents may be administered simultaneously, by the same or different routes, or at different times during treatment. In particular, the multipartite peptides may be combined with a mortalin siRNA, an anti-cancer agent, such an alkylating agent; an anthracycline antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue, and combination thereof.

In some embodiments, the multipartite peptides of the present disclosure is administered in combination or concurrently with a chemotherapeutic agent, such as paclitaxel or cisplatin.

Likewise, when treating an infectious disease, the multipartite peptides of the present disclosure may be prescribed to be taken in combination with one or more antiviral drugs. In certain embodiments, the antiviral drug is a antiretroviral drug selected from the group consisting of: protease inhibitors, nucleoside reverse transcriptase inhibitors, nucleotide reverse transcriptase inhibitors, non-nucleoside reverse transcriptase inhibitors, integrase inhibitors, entry inhibitors, and maturation inhibitors. Exemplary antiviral drugs include, but are not limited to, abacavir, acyclovir, adefovir, amantadine, amdoxovir, amprenavir, antiprotease, apricitabine, arbidol, artemisinin, atazanafir, atripla, azidothymidine (AZT), bevirimat, boceprevir, butylated hydroxytoluene (BHT), cidofovir, combivir, darunavir, delavirdine, didanosine, dipivoxil, docosanol, edoxudine, efavirenz, elvitegravir, elvucitabine, emtricitabine, enfuviritide, entecavir, etravirine, farnciclovir, foscarnet, fosamprenavir, gancyclovir, globoidnan A, GSK-572, HIV fusion inhibitors, hypericin, ibalizumab, idoxuridine, immunovir, indinavir, interferons (Types I, II and III), lamivudine, lersivirine, lopinivir, loviride, maraviroc, maribavir, MK-2048, molixan (NOV-205), moroxydine, nelfinavir, nevirapine, nexavir, non-nucleotide HIV RT inhibitors, oseltamivir, pegylated interferons (e.g., peginterferon alfa-2a), penciclovir, pencyclovir, peramivir, pleconaryl, podophyllotoxin, racivir, raltegravir, resquimod, ribavirin, rifampin, rilpivirine, rimantidine, ritonavir, saquinivir, stampidine, stavudine, taribavirin, tenofovir, tipranavir, trifluridine, trizivir, tromantidine, truvada, valaciclovir (Valtrex), valacyclovir, valganciclovir, vicriviroc, vidarabine, vivecon, zalcitabine, zanarnivir (Relenza), zidovudine, and combinations thereof.

The treatment may be carried out for a period sufficient to achieve a therapeutic effect. Typically it is contemplated that treatment would be continued indefinitely while the disease state persists, although discontinuation might be indicated if the pharmaceutical compositions no longer produce a beneficial effect. The treating physician will know how to increase, decrease, or interrupt treatment based on patient response.

Production of the Multipartite Peptide

The multipartite peptides of the present disclosure can be chemically synthesized or produced from cells transformed with polynucleotide expression vectors encoding the multipartite peptide. Multipartite peptides of the present disclosure may be synthesized using traditional liquid- or solid-phase synthesis. Fmoc and t-Boc solid phase peptide synthesis (SPPS) can be employed to grow the peptides from a carboxy to amino-terminus.

In other embodiments the multipartite peptides are synthesized using recombinant DNA technologies well known to those skilled in the art. Polynucleotide expression vectors can be designed to facilitate preparative expression levels in many different cell hosts, including bacteria, yeast, insect cells, and mammalian cells.

In one aspect, the present disclosure provides a host cell transformed with a polynucleotide or expression vector encoding the multipartite peptide. The host cells can be any bacterial or eukaryotic cell capable of expressing the multipartite peptide-encoding nucleic acids or expression vectors described herein.

In another aspect, a method of producing a multipartite peptide according to the present disclosure comprises culturing a host cell transformed with a multipartite peptide-encoding polynucleotide or expression vector under conditions that allows production of the multipartite peptide, and purifying the multipartite peptide from the cell. The peptides may be produced by culturing a cell transiently or stably expressing a multipartite peptide; and purifying the peptide from the cultured cells. Any cell capable of producing a functional peptide may be used. The peptide-expressing cell may be of prokaryotic or bacterial origin, such as *E. coli* or it may be of eukaryotic or mammalian origin, such as a human cell. In other embodiments, the cell is a yeast cell or an insect cell. Where the cell is of eukaryotic origin, the peptide-producing cell is preferably stably transformed with a polynucleotide so as to express the peptide.

The present disclosure is further illustrated by the following examples which should not be construed as limiting. The contents of all references, patents and published patent applications cited throughout this application, as well as the Figures and Tables are incorporated herein by reference.

Example 1: Materials and Methods for Examples 2-8

1-1. Cell Lines, Reagents and Antibodies.

The MCF-7 cell line, a noninvasive estrogen receptor positive (ER+) and MDA-MB-231 cell line (ER negative) were purchased from the American Type Culture Collection (ATCC, Manassas, Va.). MCF-10A cell line, a non-tumorigenic epithelial cell line was also purchased from ATCC. 3-(4,5-dimethylthiazol-2-yl)-2,5-diphenyltetrazolium (MTT), Dulbecco's Modified Eagle's Medium (DMEM) with high glucose and FLUOROBRITE™ phenol red-free DMEM, (MCF-7) were purchased from Thermo Fisher Scientific (Rockford, Ill.) The RPM 1640 medium (MDA-MB-231 cells) was obtained from Life Technologies Company (Carlsbad, Calif.). The basal medium MEBM and the additive MEGM (MCF-10A cells) were obtained from Lonzal/Clonetics Corporation (Lonza, Walkersville, Md.). Paclitaxel was purchased from Selick-Chemon, (Houston, Tex.). Cisplatin was purchased from EMD/Millipore (Billerica, Mass.). Annexin V-FITC/PI Apopto and PI Cell Cycle Kits were purchased from Nexcelom Bioscience (Lawrence, Mass.). The CD63 Rabbit polyclonal and Alix goat polyclonal antibodies were purchased from Santa Cruz Biotechnology Inc. (Santa Cruz, Calif.). The PEG-SMRwt-Clu PEG-SMRwt and PEG-SMRmut HIV-1 Nef peptides were purchased from InnoPep Company (San Diego, Calif.).

1-2. Cell Culture.

Cells were cultured in the media described above with addition of exosome-free fetal bovine serum (System Biosciences Inc., Mountain View, Calif.), 100 units/mL penicillin, and 100 mg/mL streptomycin and maintained in a humidified atmosphere at 37° C. and 5% $CO_2$.

1-3. Viability and Proliferation.

Human breast cancer cell lines were seeded into 96-well plates (5000 cells/well) and treated for 24 hours with various concentrations of SMR peptides including PEG-SMRwt-Clu, PEG-SMRwt and PEG-SMRmut to determine IC50 (inhibition concentration). Cell proliferation was determined using the MTT assay (Molecular Devices, Sunnyvale, Calif.). Control experiments were performed with MTT treated cells alone and untreated cells, and on this basis, the incubation times of 24 hr and 48 hr were used for an MTT assay of peptide-treated cells (Stockerta J C. et al., 2012 and Riss T L. et al., 2015).

1-4. Cell Cycle Analysis.

MCF-7 and MDA-MB-231 breast cancer cells were cultured into 6-well plates at $4 \times 10^5$ cells per well and treated with either paclitaxel and cisplatin or combined with PEG-SMRwt-CLU peptide for 24 and 48 hours. Cell cycle analysis was performed using a propidium iodide cell cycle assay and measured using a Cellometer (Nexcelom, MA). Further experiments were performed with SMR at IC50 concentration; the results showed 1.12 µM of PEG-SMRwt-Clu, 0.28 µM of PEG-SMRwt on MCF-7 cells for 24 hours and 0.28 µM of PEG-SMRwt-Clu, 0.42 µM of PEG-SMRwt on MDA-MB-231 cells for 24 hours for each cell time two stage. Breast cancer cells were seeded into 96-well plates at $5 \times 10^3$ cells/ml, and treated with either 1.6 µM/mL of paclitaxel, or 3 mg/mL cisplatin, 1.12 µM/mL PEG-SMRwt-CLU peptide, SMR peptide combined with paclitaxel or with cisplatin (MCF-7 cells). Alternatively 1.6 µM/mL paclitaxel or 2 mg/mL cisplatin or 0.28 µM/mL of PEG-SMR-CLU peptide, or the peptide combined with each of these drugs was used for MDA-MB-231 cells. The concentrations for cisplatin and paclitaxel were experimentally determined IC50 dosages for the different cell types (data not shown). At the end of the 24 hr or 48 hr incubations, the cells were assessed by the Cellometry imaging cytometry assay.

All above steps were done on MCF-7 and MDA-MB-231 cells separately. In order to further understand whether this peptide functions synergistically with chemotherapeutic drugs, 6 groups of cancer cells were treated as follows: 1) untreated, 2) PEG-SMRwt-CLU, 3) paclitaxel, 4) paclitaxel in combination with PEG-SMRwt-CLU, 5) cisplatin, 6) cisplatin in combination with PEG-SMRwt-CLU.

1-5. Assessment of Apoptosis.

Breast cancer cells were seeded into 6-well plates at $4 \times 10^5$ cells per well and treated with either paclitaxel or cisplatin or various concentrations of SMR peptides for 24 hours or different time point. SMR as described above. Apoptosis was determined the using AnnexinV-FITC detection kit (Nexcelom, MA) and visualized by Cellometer imaging cytometry.

1-6. Exosome Isolation and Purification.

Exosomes were isolated from breast cancer cells by differential centrifugation as previously described (Ali S A. et al., 2010). Untreated tumor cells were used as a control. Briefly, the above treated and untreated cell culture supernatants were centrifuged at 400×g for 10 minutes. The supernatants were transferred to a clear tube and centrifuged at 10,000×g for 30 minutes. The supernatants from the second spin were ultracentrifuged at 200,000×g for 2 hours to pellet exosomes. Finally, the exosome pellets were resuspended with PBS and stored at 4° C. until used for analysis.

1-7. Exosome Characterization by Acetylcholinesterase (AchE) Assay.

Purified exosomes were quantitated by measurement of AchE as described (Ellman et al., 1961). Briefly, a 100 mM dithibionitrobenzoic (DTNB) solution was prepared for use as a stock color indicator, and a 28.9 mg/mL acetylthiocholine iodide in PBS solution was prepared as a stock substrate. The stock substrate stock can be stored at −20° C. up to one month, while the color indicator can be stored at 4° C. for two weeks. A working solution was prepared by mixing 10 mL of PBS with 200 μL of Substrate and 500 μl of DTNB. 50 μl, of each exosome sample was transferred to 96 well microtitre plates, and a standard curve was prepared using AchE from 0.98 mU/mL to 2000 mU/mL. After 50 μL of standards were added into separate wells, 200 μL of the working solution was added to all wells. After 20 min incubation, AchE activity was measured at 450 nm using a SpectroMax M5 fluorimeter.

1-8. Exosome Nanoparticle Tracking Analysis NTA).

Analysis of absolute size distribution of exosomes was performed using NanoSight LM10 with NTA2.3 (NanoSight Ltd., Minton Park, UK). Particles were automatically tracked and sized based on Brownian motion and the diffusion coefficient. After isolation, the untreated and treated breast cancer exosomes were re-suspended in 0.5 mL of PBS. Control medium and filtered PBS were used as controls in this technique. The NTA measurement conditions were: temperature=21.0+/−0.5° C.; viscosity=0.99+/−0.01 cP; frames per second=25; measurement time=30 s. The detection threshold was similar in all samples. Two recordings were performed for each sample.

1-9. Western Blot Analysis.

Exosomes were isolated from culture supernatants as described above. Protein concentration was determined by measuring absorbance at 280 nm (Nanodrop 2000). Protein samples were denatured in SDS-PAGE sample buffer by heating at 95° C. for 15 min. Criterion TGX Precast Gels (4-20% Bio-Rad, Richmond, Calif.) were used to separate the proteins and blotted as previously described (Huang M B. et al 2004). Blots were incubated with the primary antibodies, anti-CD63 and anti-Alix, followed by goat or rabbit anti-Ig secondary antibodies. Specific bands were detected using ECL chemiluminescent substrate (Santa Cruz Biotechnology, Santa Cruz, Calif.) and visualized on the ImageQuant LAS 4000 imaging system (GE Healthcare, Piscataway, N.J. 08854).

1-10. Fluorescent N-Rh-PE Measurement.

The fluorescent phospholipid analog N—Rh-PE [N-(lissamine rhodamine B sulfonyl) phosphatidyl ethanolamine] is a lipid marker of exosomes and intraluminal vesicles of multivesicular bodies as previously described (Willem J et al., 1990). Briefly, 10 mM of the N—Rh-PE was stored in chloroform/methanol (2:1). A 5 μM N—Rh-PE solution in a pre-cooled reaction medium was then added to the treated with MCF-7 breast cancer cells transfected with siRNA-Negative or siRNA-HSPA9, and then were incubated at 4° C. for 1 h. After this incubation period, the medium was removed and the cells were extensively washed with cold medium to remove excess unbound lipids. Labeled cells were cultured in complete RPMI-1640 with 10% exosome-depleted FBS medium heat inactivated at 37° C. overnight. Measurement of N—Rh-PE in the collected supernatants/exosomes was carried out using a spectrometer at 550 nm and 590 nm excitation and emission wavelengths, respectively.

1-11. Transfection with Mortalin Antibody.

MCF-7 breast cancer cells were transfected with mortalin antibody using a Chariot kit (Active Motif, Carlsbad, Calif.) in accordance with the manufacturer's protocol. Following a 48 hour incubation of these cells, the exosomes were isolated and measured via AchE assay and NanoSight analysis.

1-12. Transient transfection with small interfering RNA (siRNA).

MCF-7 breast cancer cells were transfected with double-stranded siRNAs using Amaxa's Nucleofector kit (Lonza Walkersville Inc., Walkersville, Md.) in accordance with the manufacturer's protocol. Transfection of plasmids was carried out using Amaxa Biosystems Nucleofector II as recommended by the supplier. Mortalin siRNAs were prepared as previously described (Shelton et al., *J Virol* (2012) 86(1): p. 406-19). Following transfection, the cells were incubated at 37° C. for 24, 48, 72 and 96 hours, and exosomes were isolated and measured by AchE assay and Western blotting.

1-13. Statistical Analysis.

Data was expressed as the mean±standard deviation (S.D.). A two-sample t-Test assuming equal variances was used to compare the differences between controls and treated samples in each group. A value of p≤0.05 was considered to be statistically significant.

Example 2: SMR Peptides Inhibit Cell Growth of Breast Cancer Cells

Breast cancer cells were treated for 24 hours with increasing concentrations (35 nM/mL, 70 nM/mL, 140 nM/mL, 280 nM/mL, 560 nM/mL and 1120 nM/mL) of PEG-SMRwt-Clu peptide in combination with either PEG-SMRwt or PEG-SMRmut peptides as controls. Both peptides containing the SMRwt sequence inhibited breast cancer cell growth in a dose-dependent manner (FIG. 1). For MCF-7 cells, 50% inhibition was seen with 1.12 μM/mL of PEG-SMRwt-Clu and 0.28 μM/mL of PEG-SMRwt. For MDA-MB-231 cells 50% inhibition was achieved with 0.28 μM/mL of PEG-SMRwt-Clu and 0.42 μM/mL of PEG-SMRwt. The PEG-SMRmut peptide did not inhibit proliferation.

Example 3: SMRwt Peptides Induce Cell Cycle Arrest in Breast Cancer Cells

Figure 2:
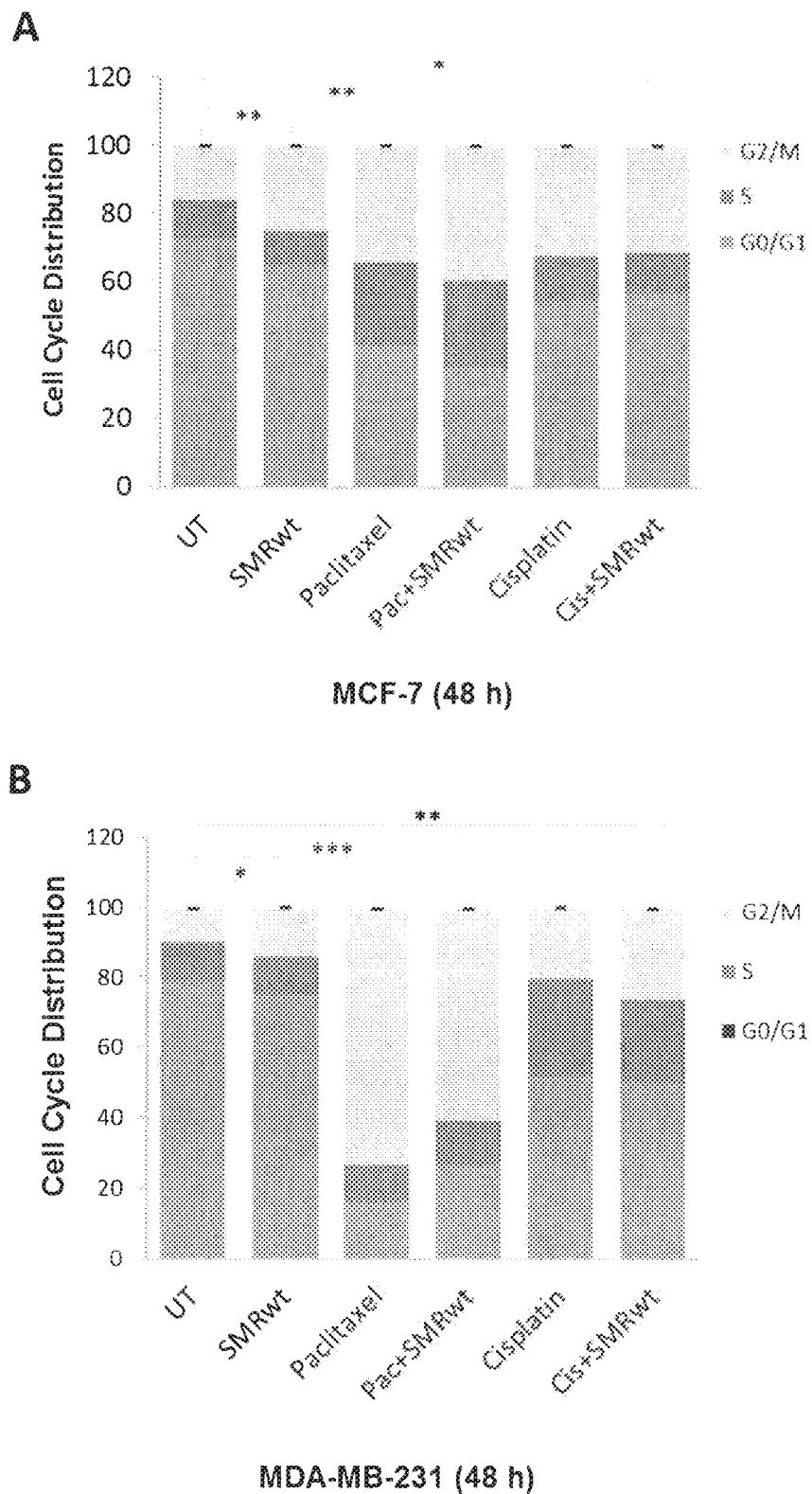
FIG. 2 shows that PEG-SMRwt-CLU peptide antagonist and chemotherapeutics induced cell cycle arrest in MCF-7 and MDA-MB-231 breast cancer cells. Cells were treated 48 hr with SMR peptides, alone or in combination with paclitaxel or cisplatin, and were assayed by Cellometer imaging cytometry, indicating percentage of MCF-7 (Panel A) and MDA-MB-231 (Panel B) in various cell cycle phases. Results of two independent experiments are shown. Significant differences relative to untreated control are indicated as follows: * $p<0.01$, ** $p<0.001$ for MCF-7 cells, and * $p<0.02$,  $p<0.01$, * $p<0.0001$ for MDA-MB-231 cells.

The data indicated that PEG-SMRwt-CLU peptides induced cell cycle arrest in MCF-7 cells and MDA-MB-231 cells assayed at 48 hours (FIG. 2). When cells were treated with the PEG-SMRwt-CLU peptide, or the peptide combined with paclitaxel or cisplatin, they were blocked in G2/M phase, indicating that PEG-SMRwt-Clu peptides contribute to induction of G2/M arrest in breast cancer cells.

Figure 3:
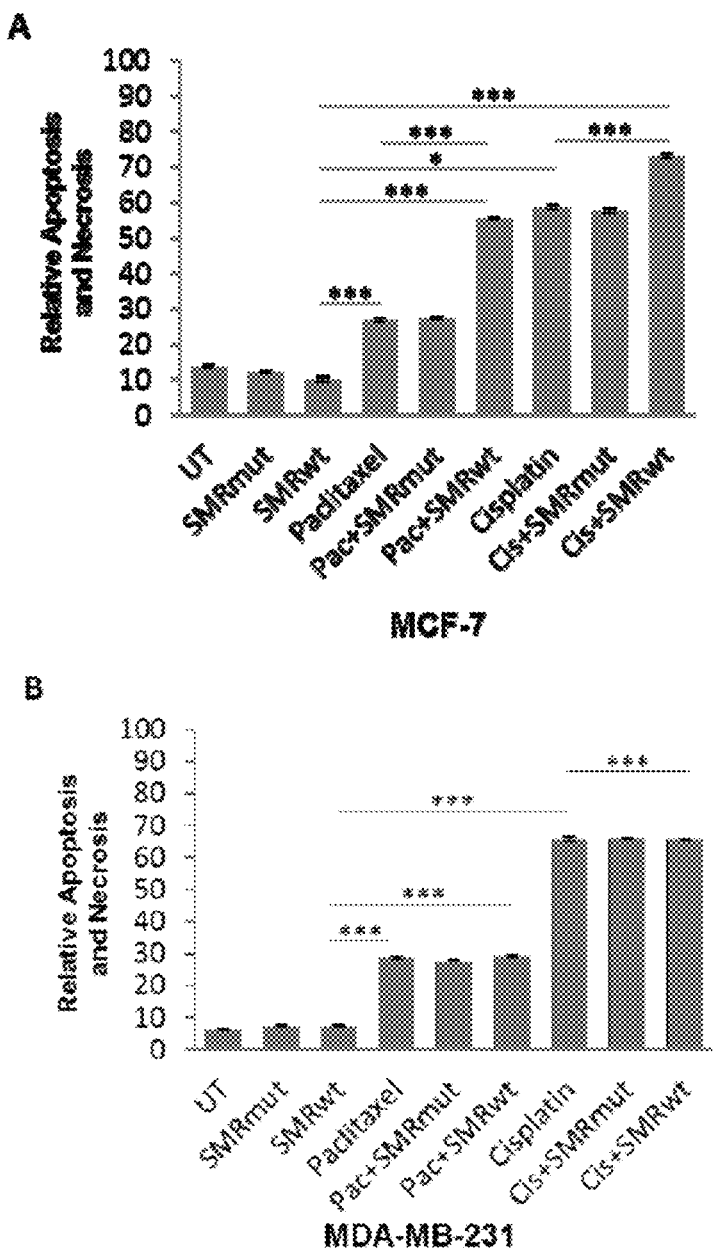
FIG. 3 shows that PEG-SMRwt-CLU peptide antagonist increased cytotoxicity in MCF-7 but not in MDA-MB-231 breast cancer cells. Percentage of apoptotic cells (Panel A) MCF-7 and (Panel B) MDA-MB-231, as determined by Annexin V-FITC assay of cells treated for 48 hr with peptide alone or combined with paclitaxel or cisplatin. Error bars represent mean±SD of four independent experiments. Significant differences relative to SMRwt peptide are indicated as follows: * $p<0.01$, *** $p<0.0001$.

Example 4: SMRwt Peptides Increased the Sensitivity of Breast Cancer Cells to Cisplatin and Paclitaxel in MCF-7 Breast Cancer Cells In a separate experiment, MCF-7 and MDA-MB-231 cells were treated with either PEG-SMRwt-CLU or PEG-SMRmut-CLU alone, or in further combination with paclitaxel or cisplatin and then assayed for apoptosis by Annexin V-FITC/PI assay. Both of these cell lines showed increased apoptosis relative to the unmodified control peptides after the incubation with paclitaxel and cisplatin for 48 hours (FIG. 3).

Interestingly, the PEG-SMRwt-Clu peptide increased the level of drug-induced apoptosis in MCF-7 cells, but not in MDA-MB-231 cells.

Example 5: SMR Peptides Block Exosome Release in Breast Cancer Cells

Acetylcholinesterase (AchE) assays, NanoSight analysis and Western blot analysis were performed to characterize exosomes released from MCF-7 and MDA-MB-231 human breast cancer cells treated for 48 hr with the various peptides. The results indicated that exosome release was inhibited by the SMRwt peptides.

AchE activity in exosomes was assayed and the results of this analysis are shown in FIGS. 4A and 4B. In MCF-7 cells, the control exosomes were found to contain 113.49 mU/mL of AchE activity. In contrast, 41.95 mU/mL of activity was found in cells treated with PEG-SMRwt-CLU peptide; 51.87 mU/mL activity was found in cells treated with PEG-SMRwt-CLU in combination with paclitaxel; and 16.95 mU/mL activity was found in cells treated with PEG-SMRwt-CLU in combination with (FIG. 4A). In MDA-MB-231 cells, the control exosomes contained 118.48 mU/mL of AchE activity, whereas 66.77 mU/mL activity was found in cells treated with PEG-SMRwt-CLU peptide; 64.15 mU/mL activity was found in cells treated with PEG-SMRwt-CLU peptide in combination with paclitaxel; and 27.0 mU/mL activity was found in cells treated with PEG-SMRwt-CLU in combination with cisplatin (FIG. 4B).

Figure 4:
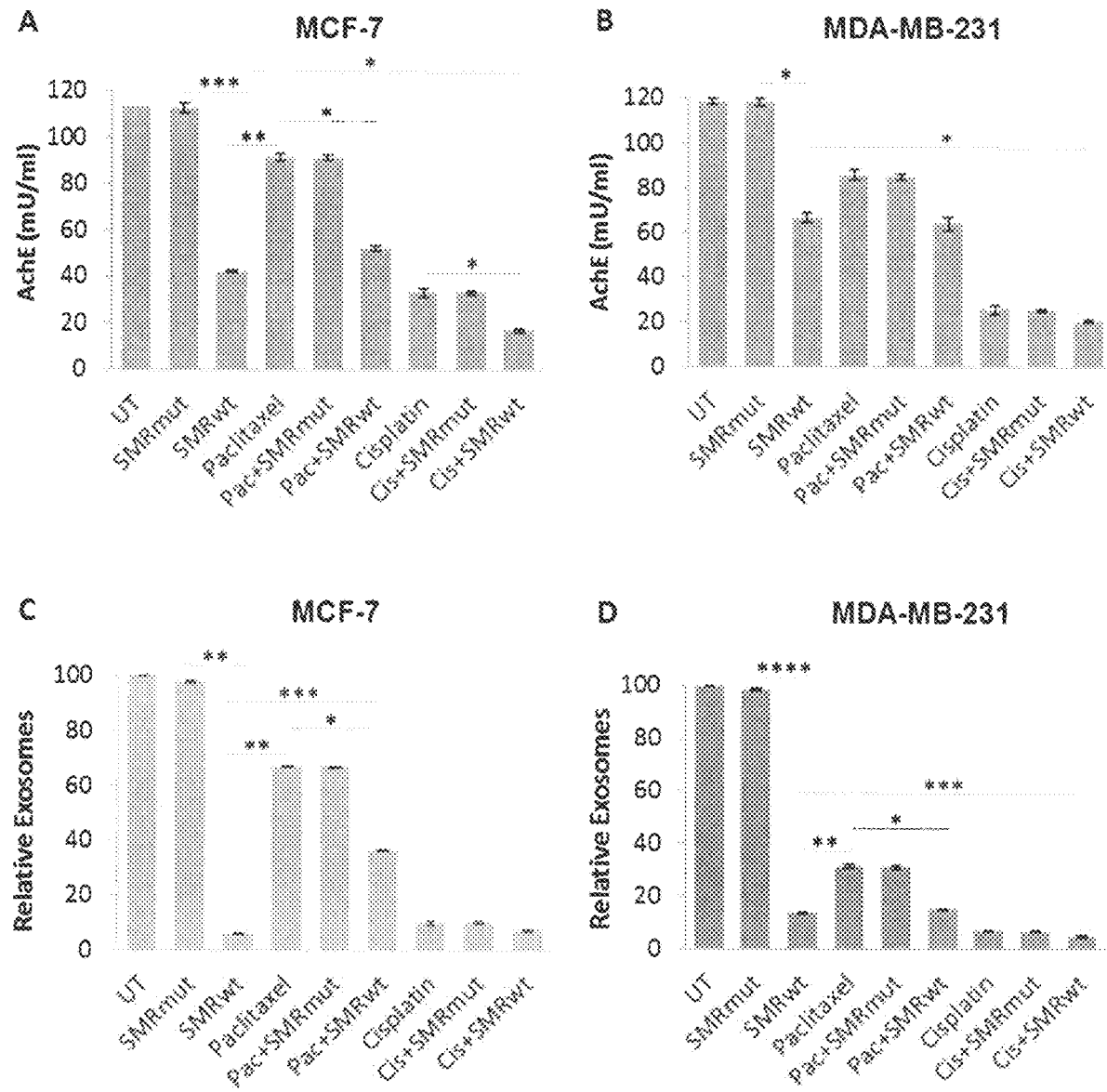
FIG. 4 shows that PEG-SMRwt-CLU peptide antagonist blocks exosome release from MCF-7 and MDA-MB-23 cells. Cells were treated for 48 hr with peptide alone or combined with paclitaxel or cisplatin. Panels A and B show relative level of exosomes released from MCF-7 and MDA-MB-231 cells respectively, determined by AchE assay. Error bars represent mean±SD of four independent experiments. Significant differences relative to SMRwt peptide: * $p<0.01$,  $p<0.001$, * $p<0.0001$ for MCF-7 cells; and * $p<0.01$ for MDA-MB-231 cells. Panels C and D show relative numbers of exosomes released by MCF-7 and MDA-MB-231 cells respectively, as determined by Nanosight measurement. Error bars represent mean±SD of two independent experiments. Significant differences relative to SMRwt peptide: * $p<0.01$,  $p<0.001$, * $p<0.0001$ for MCF-7 cells and * $p<0.03$,  $p<0.02$,  $p<0.01$ and **** $p<0.001$ on MDA-MB-231 cells.

Analysis of exosomes concentration and size distribution was assayed by NanoSight LM10 Nanoparticle Tracking Analysis (NTA). With NTA, particles are automatically tracked and sized based on Brownian motion and the associated diffusion coefficient. Before analysis of the samples by NTA, it was determined that salt aggregates from the PBS did not contribute to background and the equipment was free of contaminant particles. The untreated MCF-7 cell control medium showed a considerable number of particles ($5.16 \times 10^9$ particles/ml) (FIG. 4, Panel C). However, a reduced number of particles was found in MCF-7 cells treated with PEG-SMRwt-CLU ($3.28 \times 10^8$ particles/ml, p<2.40E-06), PEG-SMRwt-CLU in combination with paclitaxel ($5.7 \times 10^8$ particles/mL, p<0.0008) and PEG-SMRwt-CLU in combination with cisplatin ($3.77 \times 10^8$ particles/mL, p<0.0001) (FIG. 4, Panel C).

Similarly, whereas control media from MDA-MB-231 cultures also showed a considerable number of particles ($4.7 \times 10^9$ particles/ml), a reduced number of particles was found in MDA-MB-231 cells treated with PEG-SMRwt-CLU peptide ($6.8 \times 10^8$ particles/ml, p<3.96E-05), PEG-SMRwt-CLU peptide in combination with paclitaxel ($7.5 \times 10^8$ particles/mL, p<0.001) and PEG-SMRwt-CLU peptide in combination with cisplatin ($3.06 \times 10^8$ particles/mL, p<5.37E-05) (FIG. 4, Panel D). By NTA analysis, the size of the exosomes was estimated to range between 30 to 47 nm in both breast cancer cell lines.

Finally, Western blot analysis was used to detect exosome proteins in control- and peptide-treated cultures. The results of this analysis revealed the presence of human CD63 and Alix markers in the all exosomes isolated from MCF-7 cells (FIG. 5) and MDA-MB-231 cells (FIG. 6). Control exosomes showed higher expression of human CD63 from MCF-7 cells and higher expression of Alix from MDA-MB-231 cells.

Figure 7:
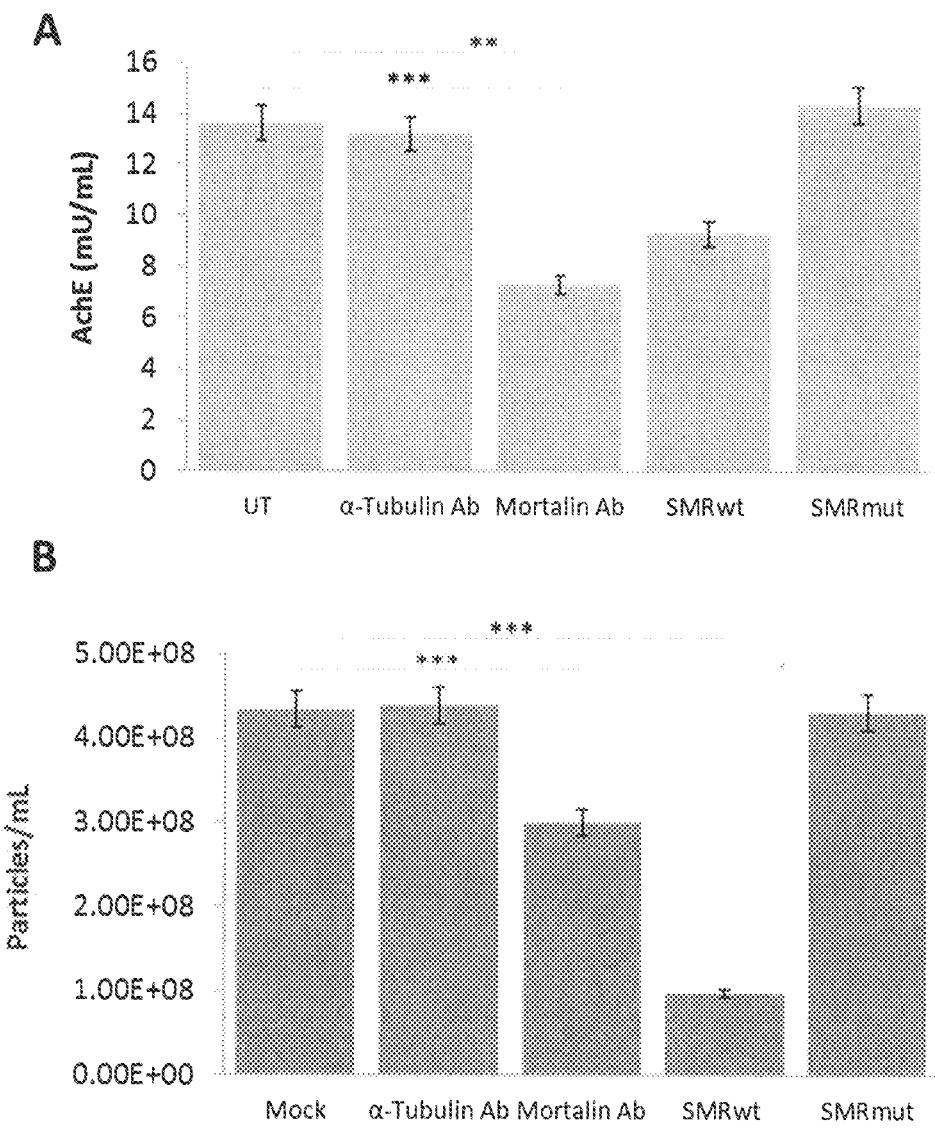
FIG. 7 shows that antibody to mortalin inhibits exosome secretion from MCF-7 breast cancer cells. MCF-7 cells were either transfected with antibodies to mortalin or alpha-tubulin, or treated with SMRwt or SMRmut peptides. Panel A: Relative exosome release level after 48 hr by AchE assay. Panel B: Relative numbers of exosomes released after 48 hr by NanoSight analysis. Error bars represent the mean±SD of three independent experiments. Significant differences relative to untreated cells: * p<0.0001, ** p<0.0001.

Example 6: Blocking the SMR-Mortalin Interaction Blocks Exosome Release in Breast Cancer Cells A previous study identified the HSP70 family protein, mortalin (encoded by HSPA9) as a binding partner for HIV-1 Nef SMR, and showed that disruption of HIV-1 Nef SMR-mortalin binding interfered with exosome release (Shelton et al., *J Virol* (2012) 86(1): p. 406-19). To test whether an analogous interaction accounts for the observed PEG-SMRwt-CLU effect on exosome release from breast cancer cells, MCF-7 cells were transfected with antibody to mortalin or antibody to α-tubulin as a control. The anti-mortalin treated cells were found to be significantly impaired in exosome release as measured by AchE assay (FIG. 7, Panel A) and slightly less so when measured by NTA assay (FIG. 7, Panel B). The effect of treatment with anti-mortalin was similar to the effect of treating MCF-7 cells with PEG-SMRwt-CLU peptide.

Figure 8:
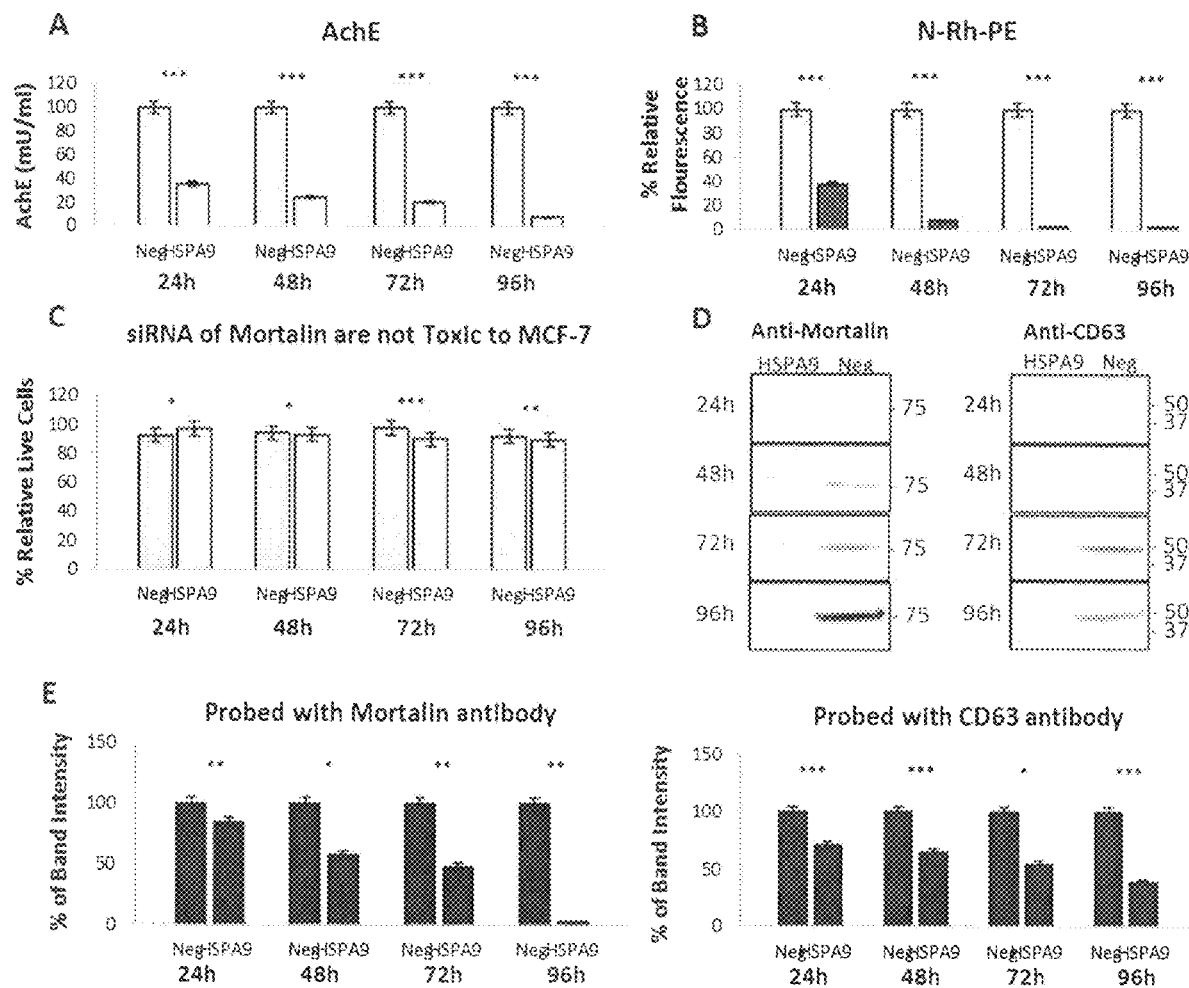
FIG. 8 shows exosome secretion is decreased in MCF-7 breast cancer cells by knockdown of mortalin expression. MCF-7 cells were transfected with clones expressing siRNA against either mortalin (HSPA9) or a negative control RNA. Exosomes were isolated and analyzed after 24, 48, 72, and 96 hr for changes in level of exosome secretion by AchE assay (Panel A). Significant differences relative to controls are indicated: * p<0.0001, and exosome secretion by N-Rh-PE (Panel B). Significant differences relative to controls are indicated: * p<0.0001. Panel C: percentage of live cells remaining at each time point, * p<0.05,  p<0.002, * p<0.0001. Panel D: mortalin and CD63 protein expression levels by Western blotting. Panel E: Densitometry analysis of Western blot data. Significant differences relative to controls are indicated: * p<0.01,  p<0.001, * p<0.0001.

To further validate the significance of this mortalin-mediated process in cancer cells, expression of mortalin protein was knocked down by transfecting MCF-7 cells with a plasmid construct expressing a mortalin siRNA. The mortalin siRNAs were found to block exosome secretion as evidenced by AchE assay and membrane fluorescence (N-Rh-PE) assays at all time points tested (FIG. 8, Panels A and B) in the absence of any cell toxicity (FIG. 8, Panel C). The exosomes from siRNA-transfected cells were further assayed for expression of mortalin and the exosome marker CD63, a tetraspanins by Western blot analysis. The results of this analysis showed that expression of both mortalin and CD63 was significantly decreased at 48 h on through to 96 h (FIG. 8, Panels D and E).

Example 7: Materials and Methods for Experiments in Examples 8-14

7-1. Cell Lines, Sera, Chemicals and Antibodies.

MDA-MB-231, MCF-7, MCF-10A and K-562 cells were purchased from American Type Culture Collection (ATCC, Manassas, Va.). Cells were cultured in RPMI 1640 (Thermo Fisher Scientific, Rockford, Ill.) supplemented with 10% heat inactivated FBS (MedSupply Partners (Atlanta, Ga.)), 1% glutamine, 100 mg/ml penicillin, and 100 mg/ml streptomycin (Life Technologies, Carlsbad, Calif.) at 37° C. and 5% $CO_2$. Normal human serum (NHS) (MedSupply Partners (Atlanta, Ga.)) was used as the source for complement proteins. Heat-inactivated normal human serum (NIS) was prepared by heating serum at 56° C. for 45 min. Rabbit polyclonal anti-mortalin antibody (anti-Grp75) was purchased from Abcam, Inc., (Cambridge, Mass.); goat polyclonal anti-Alix antibody and mouse monoclonal anti-α-Tubulin antibody were purchased from Sigma-Aldrich, Inc., (Louis, Mo.). Peroxidase-conjugated goat anti-mouse IgG, peroxidase conjugated rabbit anti-goat IgG, and FITC-conjugated goat anti-mouse IgG were purchased from Thermo Fisher Scientific. Inc., (Rockford, Ill.).

7-2. Peptides.

The PEG-SMRwt-Clu, PEG-SMRmut-Clu, SMRwt-CPP and SMRmut-CPP peptides were custom made by InnoPep Inc. (San Diego, Calif.) (FIG. 9).

7-3. Mortalin (HSPA9) DNA Constructs.

The BLOCK-iT Pol II miR RNAi expression vector kit from Life Technologies Corporation (Carlsbad, Calif.) and the mortalin (HSPA9) primers Hmi 408224 to Hmi 408227 were used to generate an expression vector with spectinomycin resistance (miR-mortalin) that expresses mortalin microRNA (miRNA; miR). The kit also contained a corresponding pcDNA6.2-GW/miR-negative control plasmid (miR-neg) predicted not to target any known vertebrate gene.

7-4. Cell Proliferation and Cytotoxicity Assay.

Figure 10:
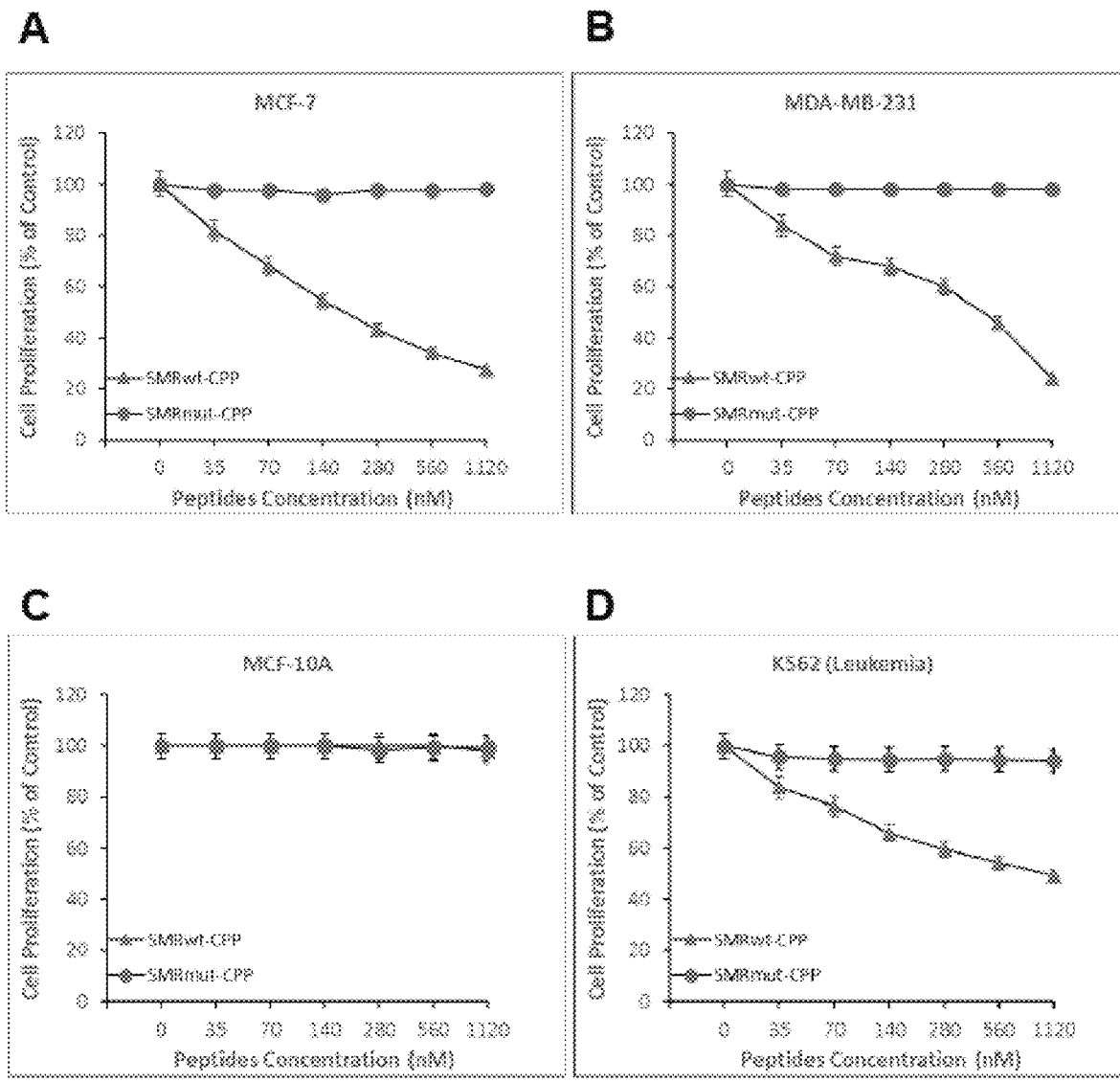
FIG. 10 shows that SMRwt-CPP peptides reduce proliferation of MCF-7 and MDA-MB-231 breast cancer cells and K562 leukemia cells, but not non-tumorigenic MCF-10A cells. Cells were incubated with peptides at varying dosages (0-1120 nM/mL) for 24 hour at 37° C., after which proliferation was measured by an MTT assay. The results of three independent experiments are shown in Panels A-D. Panel A shows reduced proliferation of MCF-7 breast cancer cells with an IC50 of 180 nM/mL; Panel B shows reduced proliferation of MDA-MB-231 breast cancer cells with an IC50 of 476 nM/mL; Panel C shows no effect on proliferation of non-tumorigenic MCF-10A cells as control cells; Panel D shows reduced proliferation of K562 leukemia cells with an IC50 of 907 nM/mL. The reduced proliferation in Panels A, B and D was observed only in the presence of wile-type SMR, but not in the presence of the mutant SMR.

Human breast cancer cell lines MCF-7, MDAMB-231, and leukemia K562 cells, and non-tumorigenic MCF-10A cells are seeded into 96-well plates (5000 cells/well) and treated for 24 hours with 0-1120 nM SMRwt-CPP or SMR-mut-CPP (FIG. 10). Cell proliferation was determined using the MTT [3-(4,5-dimethylthiazol-2-yl)-2,5-diphenyltetrazolium bromide] dye assay by SpectraMax M5 Fluorescence Plate Reader (Molecular Devices. Sunnyvale, Calif.). Cell viability was estimated by the conversion of yellow MTT by mitochondrial dehydrogenases of living cells to purple formazon (MTT assay). Control experiments were performed with cells treated or untreated with MTT, and on this basis, an incubation time of 24 hours was used for MTT assays of peptide-treated cells (Huang, M. B., et al., Oncotarget, 2017. 8(7): pp. 11302-11315.). Statistical significance of results was determined from three independent experiments including triplet or quadruplet sets in each experiment.

7-5. Exosome Isolation and Purification.

Exosomes were isolated from breast cancer cells and leukemia cells using the ExoQuick-TC Exosome Precipitation Kit (System Biosciencences [SBI], Mountain View Calif.) or the miRCURY Exosome Isolation Kit (EXIQON, Woburn, Mass.) according to the manufacturer's instructions. Untreated tumor cells were used as a control. Briefly, treated and untreated cell culture supernatants (10 mL) were centrifuged at 3000×g for 15 minutes. The resulting supernatants were transferred to a clear tube, 2 mL of ExoQuick-TC buffer was added, mixed and incubated overnight at 4° C. Following the incubation, the sample contents were centrifuged at 1500×g for 30 minutes, the supernatants were aspirated off, the pellets were centrifuged at 1500×g for 5 minutes and any further traces of supernatant were removed (SBI). Alternatively, treated and untreated cell culture supernatants were centrifuged at 10,000×g for 5 minutes to remove cell debris, supernatants (10 ml) were transferred into new tubes, and 4 mL of precipitation buffer (EXIQON) was added, and the contents were mixed and incubated at 4° C. overnight. Following the incubation, the sample contents were centrifuged at 10,000×g for 30 minutes (EXIQON). Exosome-containing pellets were re-suspended in PBS and stored at 4° C. or –80° C.

7-6. Exosome Characterization by Acetylcholinesterase (AchE) Assay.

Purified exosomes were quantitated by measurement of AchE as previously described (Huang et al., Oncotarget, 2017. 8(7): pp. 11302-11315). Briefly, 100 mM dithibionitrobenzoic (DTNB) was prepared as a stock color indicator, and prepared a stock substrate containing 28.9 mg/mL of acetylthiocholine iodide in PBS. Substrate stock can be stored at –20° C. up to one month; the stock color indicator can be stored at 4° C. for two weeks. A working solution was prepared by mixing 10 mL of PBS with 200 µL of substrate and 500 µl of DTNB. 50 µL of each exosome sample was transferred to a 96 well microtitre plate, and a standard curve for AchE concentrations was prepared using AchE from 0.98 mU/mL to 2000 mU/mL. After 50 µL of standards were added into separate wells, 200 µL of the working solution was added to each well. After a 20 min incubation, AchE activity was measured at 450 nm using a SpectroMax M5 fluorometer (FIG. 11).

7-7. Protein Analysis by Western Blotting.

Figure 12:
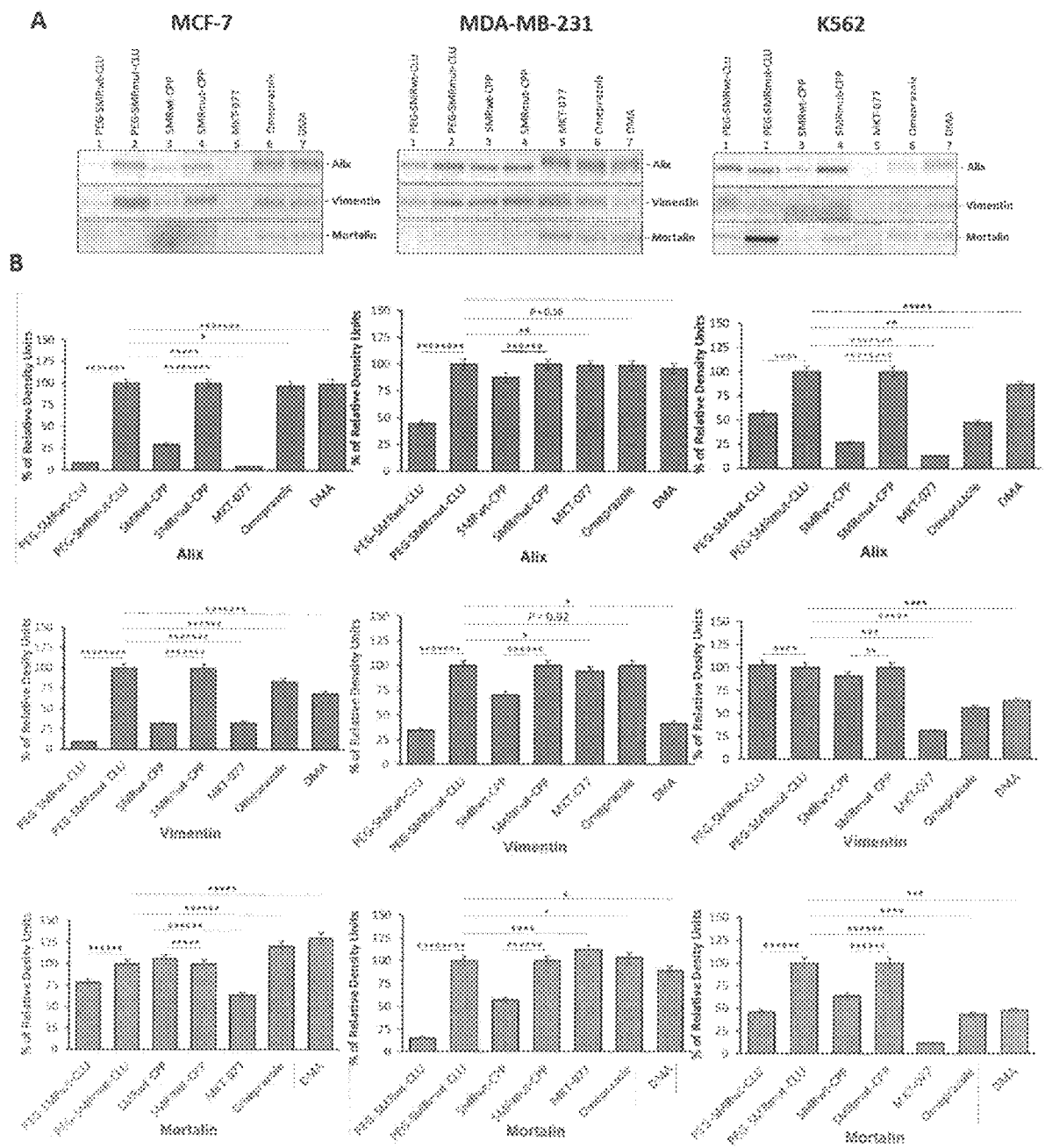
FIG. 12 shows detection of mortalin, vimentin and the exosome-specific ALIX protein in exosomes released from MCF-7 breast cancer cells, MDA-MB-231 breast cancer cells and K562 leukemia cells treated with PEG-SMRwt-Clu, PEG-SMRmut-Clu, SMRwt-CPP, SMRmut-CPP, MKT-077. Omeprazole or DMA for 48 hours at 37° C. Western blot analysis was carried out using anti-mortalin (Grp-75), anti-Vimentin and anti-Alix antibodies to evaluate mortalin, vimentin and exosomes expression. Panel A shows gel images of the exosome products, mortalin, vimentin and Alix in MCF-7 and MDA-MB-231 breast cancer cells and K562 leukemia cells; Panel B shows band intensities of the exosome products mortalin, vimentin and Alix in MCF-7 and MDA-MB-231 breast cancer cells and K562 leukemia cells. Quantitative results from Western blots were obtained by densitometry analysis of relative band intensities. The data shown represent the mean±SD of three independent experiments. Significant differences relative to treatment with peptide are indicated as follows: * p<0.01,  p<0.001, * p<0.0001, *p<0.00001,  p<0.000001, ** p<0.0000001, *** p<0.00000001, ****** p<0.000000001.

Exosomes were isolated from cell culture supernatants as described above. Protein concentrations were determined by measuring absorbance at 280 nm (Nanodrop 2000). Cultured cells were treated with PEG-SMR-Clu, SMR-CPP peptides, MKT-077, Omeprazole or DMA at 37° C. for 48 hr. To evaluate mortalin, vimentin and exosome expression, Western blot analysis was performed using anti-mortalin (Grp-75), anti-Vimentin and anti-Alix antibodies, respectively (FIG. 12).

Figure 15:
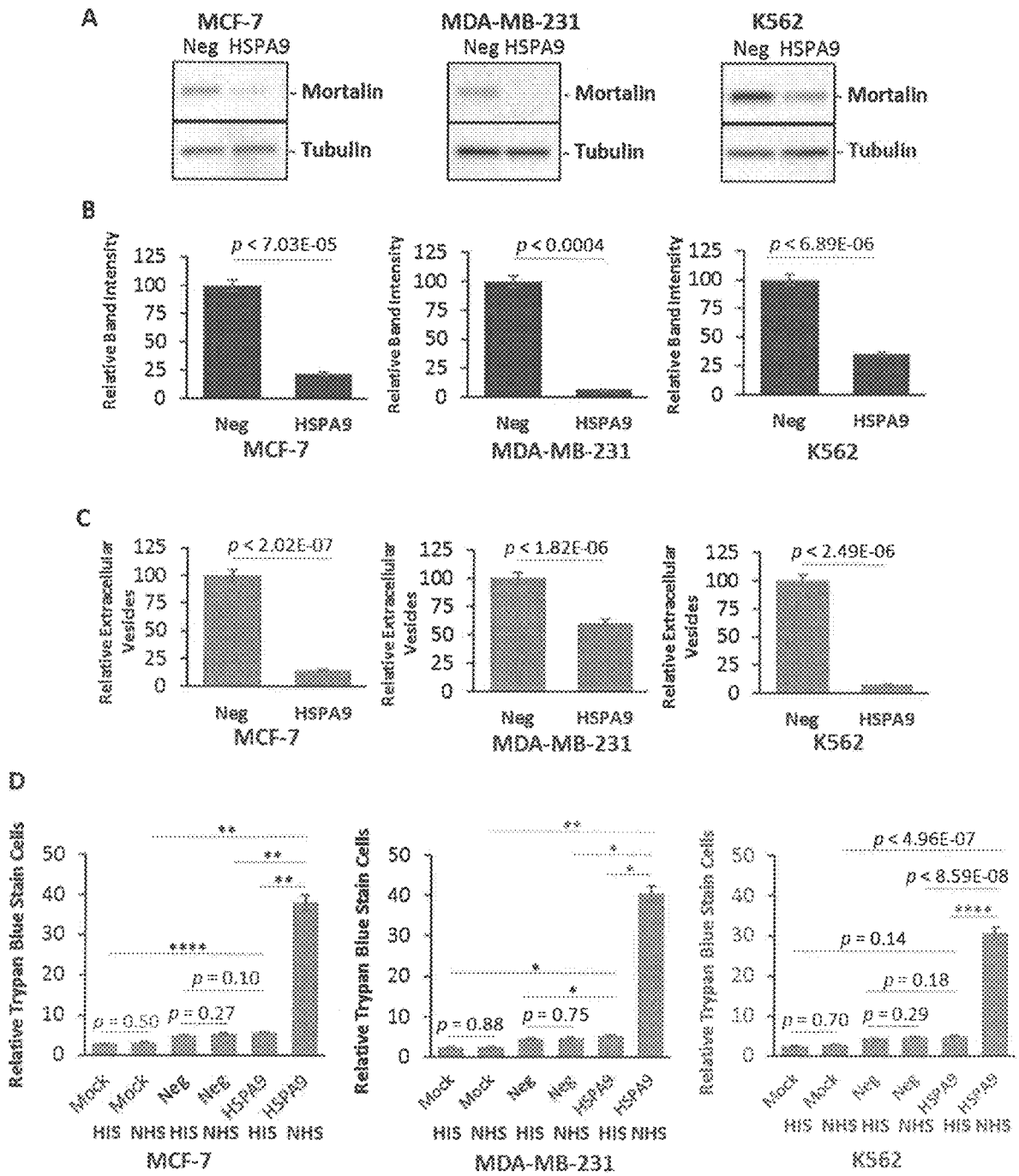
FIG. 15 shows that knockdown of mortalin expression induced complement-mediated cytotoxicity in K562, MCF-7 and MDA-MB-231 cell cultures. Cells were transfected with a vector expressing double-stranded mortalin siRNAs. Panel A shows detection of mortalin and α-tubulin following SDS-PAGE/Western blot analysis using anti-mortalin and anti-α-tubulin antibodies; Panel B shows the relative band intensities corresponding to the detected products in Panel A; Panel C shows the relative numbers of exosomes released by MCF-7, MDA-MB-231 and K562 cells as determined by NanoSight measurement; Panel D shows that siRNA-mediated knockdown of mortalin expression (HSPA9) induced complement-mediated cytotoxicity in the presence of normal human serum (NHS), but not in the presence of heat-inactivated serum (HIS), nor in mock-transfected cells or in cells expressing non-mortalin siRNAs (Neg ("Neg" means an siRNA predicted not to target any known vertebrate gene)) regardless of the presence or absence of NHS. Significant differences relative to siRNA-Neg transfected cells with NHS and mortalin siRNA transfected cells treated with NHS are indicated as follows: * $p<0.01$, ** $p<0.001$.

For collection of proteins secreted from cells undergoing complement attack, cells were treated with an anti-CXCR4 antibody and normal human serum or heat-inactivated human serum for 10 min at 37° C. The cells were then washed with PBS and suspended in medium and incubated at 37° C. After 20 min, the cells were removed by centrifugation at 350×g for 5 min (FIG. 15).

Exosomes and cell lysates were prepared by incubating 5-10 min at 95° C. in sample buffer. The lysates were subjected to SDS-PAGE under reducing conditions (150 mM DTT) in 4-20% Criterion™ TGX™ precast gels (Bio-Rad, Hercules, Calif.) and then transferred onto a nitrocellulose membrane (Bio-Rad, Hercules, Calif.). Nitrocellulose membranes were blocked with 5% skim milk (MedSupply, Atlanta, Ga.) in TBS containing 0.05% Tween 20 (TBST) for 1 h at room temperature. The membranes were treated with anti-mortalin (Grp-75) mAb or anti-α-tubulin mAb for cell lysates (FIG. 15, Panels A and B) or with anti-Alix and anti-vimentin or anti-mortalin for exosomes (FIG. 12), followed by peroxidase-conjugated goat anti-mouse IgG. Bands were developed with an ECL chemiluminescent substrate (Santa Cruz Biotechnology, Santa Cruz, Calif.) and exposed to an ImageQuant LAS 4000 imaging system (GE Healthcare, Piscataway, N.J. 08854).

7-8. Apoptosis Assay by Flow Cytometry.

Figure 13:
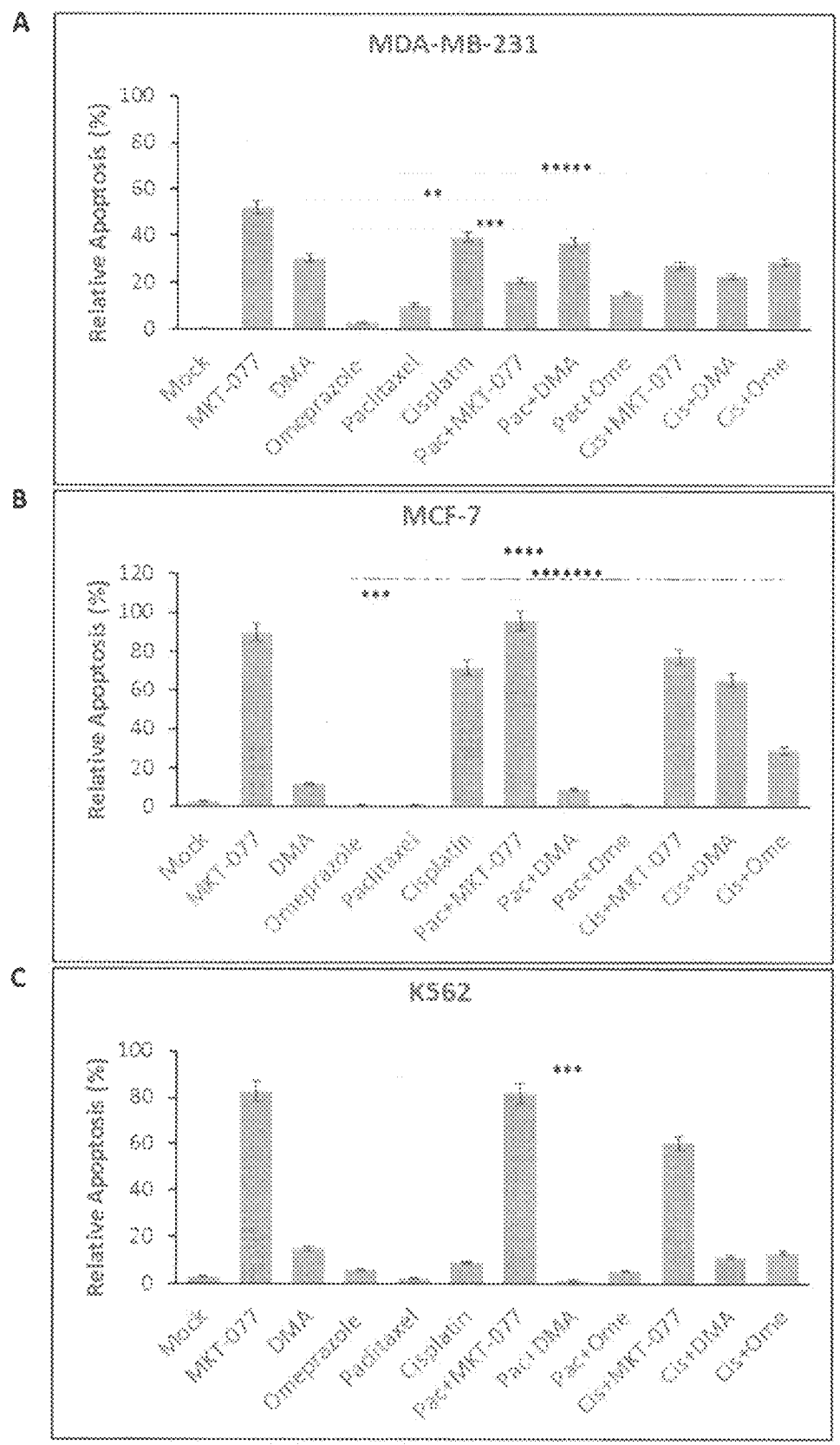
FIG. 13 shows the effects of the mortalin inhibitors MKT-077, DMA and Omeprazole on paclitaxel- (Pac) or cisplatin (Cis)-induced apoptosis in cancer cells. Cells were treated for 48 hr with 925 nM/mL of MKT-077 on MDA-MB-231 cells, 500 nM/mL of MKT-077 on MCF-7 cells, 337.5 nM/mL of MKT-077 on K562 cells, 300 µM/mL of DMA, 200 µM/mL of Omeprazole, 1.6 uM/mL of paclitaxel, 2 mg/mL of cisplatin, or combined treatment with either paclitaxel or cisplatin in combination with each of the three mortalin inhibitors. Panel A: Relative level of apoptosis from MDA-MB-231 cells; Panel B: Relative level of apoptosis from MCF-7 cells; and Panel C: Relative level of apoptosis from K562 leukemia cells, as determined by TUNEL assay. Error bars represent mean±SD of four independent experiments. Significant differences relative to inhibitors are indicated as follows: significant differences relative to DMA versus DMA combined Paclitaxel and Omeprazol versus Omeprazol combined Paclitaxel and Omeprazol combined Cisplatin, respectively, are indicated as follows:  p<0.002, * p<0.0002 and *** p<3.68E-06 for MDA-MB-231 cells; MKT-077 versus MKT-077 combined Paclitaxel, DMA versus DMA combined Cisplatin, Omeprazole versus Omeprazole combined Cisplatin, respectively, are indicated as follows: * p<0.0001, ** p<6.18E-05, *** p<7.75E-08 for MCF-7 cells; Omeprazole versus Omeprazole combined Cisplatin are indicated * p<0.0009 for K562.

For assessment of apoptosis, MCF-7 and MDA-MB-231 breast cancer cells and were seeded into 6-well plates at $4 \times 10^5$ cells per well and treated for 48 hours with 925 nM/ml, of MKT-077 on MDA-MB-231 cells, 500 nM/mL of MKT-077 on MCF-7 cells, 337.5 nM/mL of MKT-077 on K562 cells, 300 µM/mL of DMA, 200 µM/mL of Omeprazole, 1.6 uM/mL of paclitaxel, 2 mg/mL of cisplatin, or combined treatment with either paclitaxel or cisplatin in combination with each of the three mortalin inhibitors. Apoptosis was determined using the TUNEL detection kit (Nexcelom, MA) and GUAVA easyCyte HT (EMD Millipore Corporation, Temecula, Calif.) system for fluorometric detection. (FIG. 13).

7-9. Complement-Mediated Cell Cytotoxicity Assay.

Figure 14:
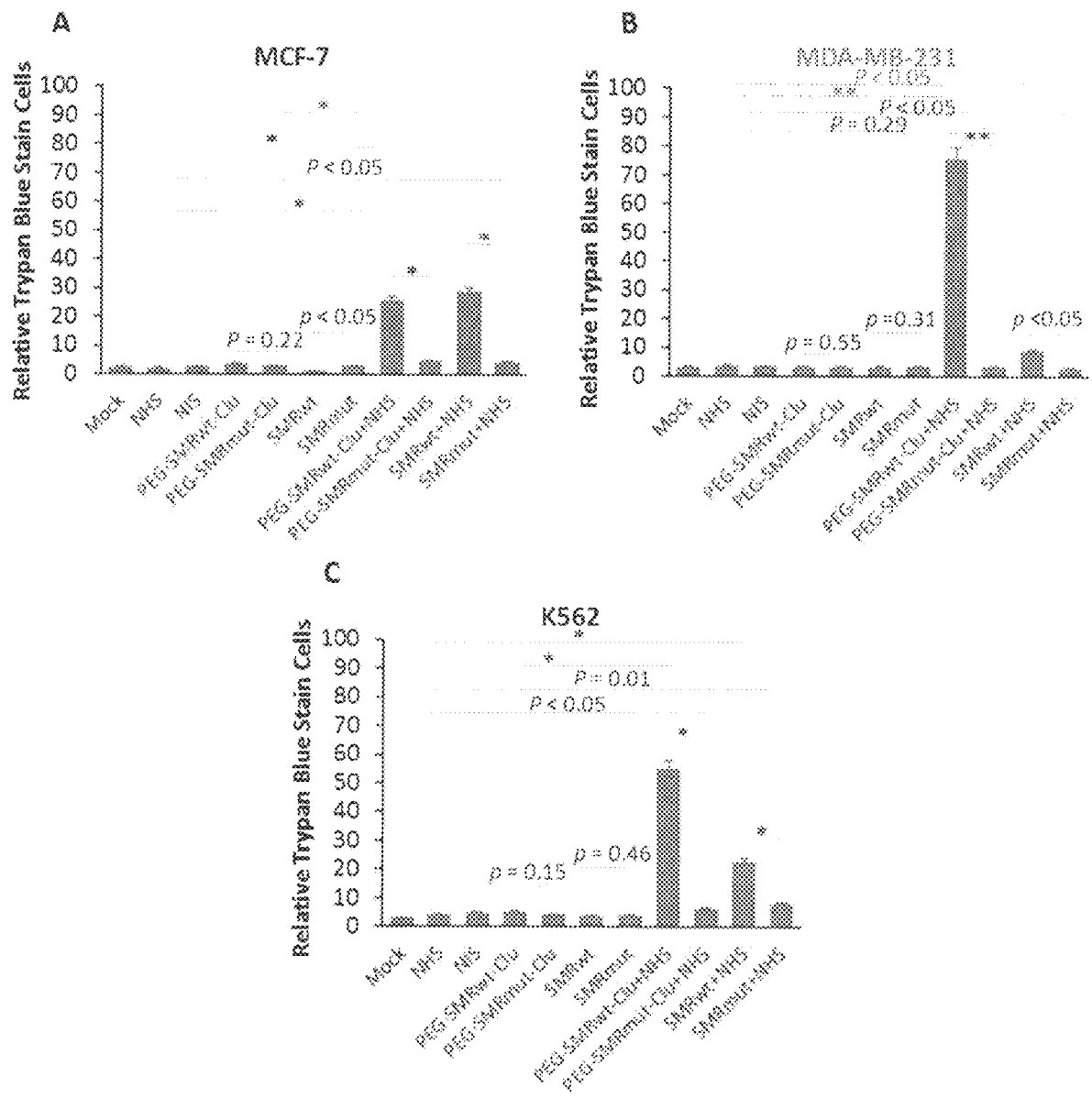
FIG. 14 shows that in the presence of NHS, PEG-SMRwt-Clu and SMRwt-CPP peptides SMRwt peptides block secretion of mortalin and exosomes and induce complement-mediated cytotoxicity in K562, MCF-7 and MDA-MB-231 cultures. Cells were treated with 280 nM PEG-SMRwt-Clu peptide or 560 nM SMRwt-CPP peptide alone for 60 min at 37° C., followed by treatment with 1 µg/mL anti-CXCR4 antibody and 50 µL NHS or NIS for additional 60 min at 37° C. PEG-SMRmut-Clu peptide and SMRmut-CPP peptide were used as negative controls. The percentage of stained (dead) cells is representative of 3 independent experiments. Panels A-C show relative levels of cells surviving a complement attack as determined by trypan blue exclusion. Panel A shows percent cell survival following treatment of MCF-7 breast cancer cells (as indicated); Panel B shows percent cell survival following treatment of MDA-MB-231 breast cancer cells; and Panel C shows percent cell survival following treatment of K562 leukemia cells. Cytotoxicity was not observed in cells treated with SMR peptides alone. Error bars represent mean±SD of four independent experiments. Significant differences relative to PEG-SMRwt-Clu peptide and SMRwt-CPP peptide are indicated as follows: * p<0.01, ** p<0.001.

Complement-mediated cell cytotoxicity assays were performed as previously described (Reiter et al., *Mol Immunol*. (1992) 29(6): p. 771-81). Briefly, MCF-7, MDA-MB-231 and K562 cells were either mock-transfected or transfected with mortalin siRNA. Cells were incubated with 1 µg/ml of anti-CXCR4 antibody for 30 min at 4° C., followed by treatment with PEG-SMRwt-Clu peptide or PEG-SMRmut-Clu peptide or SMRwt-CPP peptide or SMRmut-CPP peptide alone, or treated with SMR peptide combined with complement from normal human serum (NHS) or heat-inactivated normal human serum (NIS) for 60 min at 37° C. Percentage of cells lysed were determined by a trypan blue exclusion assay using the TC10™ Automated Cell Counter (Bio-Rad, Richmond Calif.). (FIG. 14, FIG. 15, Panel D).

7-10. Transient Transfection with Mortalin Small Interfering RNA (siRNA).

MDA-MB-231, MCF-7 breast cancer cells and K562 leukemia cells were plated in T-75 flasks with exosome-free medium. After 24 hours in a 37° C. incubator, the cells were transfected with a vector expressing double-stranded mortalin siRNAs (see section 7-3) using Amaxa's Nucleofector II kit (Lonza Walkersville Inc., Walkersville, Md.) according to the manufacturer's protocol. Mock-transfected cells ("Mock") or cells treated a non-mortalin siRNA expression vector (Neg) were used as negative controls. Following transfection, the cells were incubated in culture medium at 37° C. for 72 hours before being evaluated by Western blot analysis (FIG. 15, Panel A) and an AchE assay (FIG. 15, Panel C).

7-11. Exosome Nanoparticle Tracking Analysis (NTA).

Analysis of absolute size distribution of exosomes (300 µL) was performed using NanoSight LM10 with NTA2.3 (NanoSight Ltd., Minton Park, UK). Particles were automatically tracked and sized based on Brownian motion and the diffusion coefficient. After isolation, the untreated and treated breast cancer cell or leukemia cell exosomes were re-suspended in 0.5 mL of PBS. Control medium and filtered PBS were used as controls in this technique. The NTA measurement conditions were: temperature=21.0+/−0.5° C.; viscosity=0.99+/−0.01 cP; frames per second=25; measurement time=30 s. The detection threshold was similar in all samples. Two recordings were performed for each sample (FIG. 15, Panel C).

7-12. Cell Migration Assay.

Cell migration assays were performed using the InnoCyte Cell Migration Assay (EMD Millipore Corporation, Temecula, Calif.) according to the manufacturer's instructions. Briefly, cell migration was monitored in the presence and absence of SMRwt peptides or latrunculin A (positive control inhibitor), which were added to the lower chamber of a 96-well plate. MCF-7 and MDA-MB-231 breast cancer cells and non-tumorigenic MCF-10A breast cells were harvested by 0.25% Trypsin-EDTA (Life Technologies) release and resuspended at 250,000~500,000 cells/ml in serum-free RPMI 1640 media. A total of 25,000-50,000 cells was added to the upper chamber and allowed to migrate through an 8-µm pore-size membrane for 24 hours at 37° C. in a 5% $CO_2$ atmosphere. Cells that migrated through the membrane were detached and labeled with Calcein-AM fluorescent dye. Fluorescence was measured using a Fluorescence Plate Reader (Molecular Devices, Sunnyvale, Calif.) with an excitation wavelength of 485 nm and an emission wavelength of 515 nm. The experiment was repeated in triplicate, and each conditioned experiment was performed in quadruplicate.

13. Statistical Analysis.

Data are expressed as the mean±standard deviation (S.D.). A two-sample t-test assuming equal variances was used to compare the differences between controls and treated samples in each group. A value of $p \leq 0.05$ was statistically significant.

Example 8: SMRwt-CPP Peptides Inhibit Cell Proliferation and Growth in Breast and Leukemia Cancer Cell Lines MCF-7 and MDA-MB-231 breast cancer cells and K562 leukemia cell cultures were treated for 24 hours with increasing concentrations (35 nM/mL, 70 nM/mL, 140 nM/mL, 280 nM/mL, 560 nM/mL and 1120 nM/mL) of either SMRwt-CPP peptide or the negative control peptide SMRmut-CPP. As shown in FIG. 10, growth was inhibited by the in all cells tested in a dose-dependent manner by SMRwt-CPP peptide, but not the negative control peptide. The inhibition observed was found to be dose dependent, with a typical sigmoidal shape of dose response, corroborating validity of the observations. The growth curves further relate the specific dosage providing 50% inhibition (IC50) by SMRwt-CPP, whereby the IC50 against MCF-7 was 180 nM/mL (FIG. 10, Panel A), against MDA-MB-231 was 476 nM/mL (FIG. 10, Panel B) and against K562 was 907 nM/mL (FIG. 10, Panel D). Non-tumorigenic MCF-10 OA breast cells were used as a negative cell control and were not affected by SMRwt-CPP (FIG. 10, Panel C).

Example 9: SMRwt Peptides and Mortalin Inhibitors Block Exosome Release in Breast and Leukemia Cancer Cell Lines PEG-SMRwt-Clu peptide was previously shown to block exosome release in breast cancer cells (Huang et al., *Oncotarget* (2017) 8(7): p. 11302-11315). To further examine the underlying mechanism for blocking exosome release, a study was extended to examine the effects of the SMRwt peptides, PEG-SMRwt-Clu peptide and SMRwt-CPP peptide, and the mortalin inhibitors MKT-077, Omeprazole, and DMA on exosome release. In particular, acetylcholinesterase (AchE) assays, NanoSight analysis and Western blot analysis were performed to characterize exosomes released from MCF-7 and MDA-MB-231 human breast cancer cells and K562 leukemia cells. Cells were treated for five days at 37° C. with the various peptides and mortalin inhibitors as indicated in FIG. 11. Panels A, B and C depict the relative numbers of exosomes released as a function of time as measured by an acetylcholinesterase (AchE) assay in MCF-7 breast cancers cells (FIG. 11, Panel A); MDA-MB-231 breast cancer cells (FIG. 11, Panel B); and K562 leukemia cells (FIG. 11, Panel C).

The results of this analysis show that the SMRwt peptides, PEG-SMRwt-Clu peptide (SEQ ID NO: 37) and SMRwt-CPP peptide (SEQ ID NO: 39), and the mortalin inhibitors, MKT-077, Omeprazole and DMA all reduced the number of exosomes release over the entire five day treatment period. As shown in FIG. 11, Panels A-C, there was an initial increase in exosome release on days 1 and/or 2 under all treatment conditions and a subsequent decrease in exosome release thereafter, although the initial increases and subsequent decreases were substantially reduced in cells treated with the SMRwt peptides or mortalin inhibitors. In particular, AchE concentrations in MCF-7 cells treated with the negative controls (i.e., mock, PEG-SMRmut-Clu (SEQ ID NO: 43), and SMRmut-CPP (SEQ ID NO: 41)) were 155.13 mU/mL, 151.5 mU/mL and 150.06 mU/mL, respectively. On day 3, a rapid decrease was observed under these treatment conditions (69.15 mU/mL, 69.0 mU/ml, and 66.05 mU/mL) with a subsequent increase in AChE concentrations on day 4 and day 5.

In contrast, MCF-7 cells treated with PEG-SMRwt-Clu (SEQ ID NO: 37), SMRwt-CPP (SEQ ID NO: 39), MKT-077, Omeprazole, and DMA were found to exhibit reduced AChE concentrations throughout days 1 to day 5, wherein the average AChE concentrations were 31 mU/mL, 22 mU/mL, 22 mU/mL 26 mU/mL and 26 mU/mL, respectively.

FIG. 11, Panel B shows the results obtained for similar treatments in MDA-MB-231 breast cancer cells. In this case, initial increases in AChE of 146.52 mU/mL, 146.79 mU/mL and 141.47 mU/mL were observed on day 1 for mock, PEG-SMRmut-Clu, and SMRmut-CPP treatments, respectively, which were followed by decreases in AChE concentrations on days 2-5. In MDA-MB-231 cells treated with PEG-SMRwt-Clu, SMRwt-CPP, MKT-077, Omeprazole, and DMA, however, the AChE levels were maintained at average concentration levels throughout day 1 to 5 of 42 mU/mL, 29 mU/mL, 29 mU/mL, 25 mU/mL and 37 mU/mL, respectively.

FIG. 11, Panel C shows the results obtained for similar treatments in K562 leukemia cells. In this case, average AChE levels in the negative control groups from days 1 to 5 were 48 mU/mL, 71 mU/mL, 75 mU/mL, 69 mU/mL and 59 mU/mL, respectively. By contrast, average AChE levels on days 1-3 and 5 in K562 cells treated with PEG-SMRwt-Clu, SMRwt-CPP, MKT-077, Omeprazole, and DMA were 18 mU/mL, 25 mU/mL, 21 mU/mL and 18 mU/mL with day 4 showing an increase relative to the other days (i.e., 41 mU/mL). These results further confirm that exosome release was inhibited by all experimental treatments (FIG. 11).

Example 10: Effect of SMRwt Peptides and Mortalin Inhibitors on Exosomal Protein Content Western blot analysis was used to examine the effects of the SMRwt peptides, PEG-SMRwt-Clu peptide and SMRwt-CPP peptide, and the mortalin inhibitors MKT-077, Omeprazole, and DMA on exosomal protein content in MCF-7, MDA-MB-231 and K562 cells. Negative control treatments included PEG-SMRmut-Clu peptide and SMR-mut-CPP peptide. Exosomes were isolated from all treated and untreated cell lines screened. Western blot analyses were carried out to evaluate the expression levels of the exosomal proteins, Alix, mortalin, and vimentin in MCF-7 breast cancer cells (FIG. 12, Panel A, left sub-panel), MDA-MB-231 breast cancer cells (FIG. 12, Panel A, middle sub-panel), and in K562 leukemia cells (FIG. 12, Panel A, right sub-panel).

As shown in FIG. 12, Panel A, left sub-panel and FIG. 12, Panel B, top left sub-panel), Alix expression in exosomes from MCF-7 cells were significantly decreased in PEG-SMRwt-CLU, SMRwt-CPP and MKT-077 treatments. However, as shown in FIG. 12, Panel B, top left sub-panel, treatment of MCF-7 cells with Omeprazole or DMA were not accompanied by significant reductions in Alix expression. Vimentin expression in exosomes from MCF-7 cells was significantly decreased for all treatments (PEG-SMRwt-Clu, SMRwt-CPP, MKT-077, omeprazole and DMA) relative to the negative controls (PEG-SMRmut-Clu and SMR-mut-CPP)(FIG. 12, Panel B, middle left sub-panel. Mortalin expression in MCF-7 exosomes was only significantly decreased following treatment with PEG-SMRwt-Clu peptide or MKT-077, however, no significant changes in mortalin expression were observed following treatment with SMRwt-CPP, Omeprazole, or DMA (FIG. 12, Panel B, bottom left sub-panel).

In MDA-MB-231 breast cancer cells (FIG. 12, Panel A, middle top sub-panel and FIG. 12, Panel B, middle top sub-panel), Alix expression in MDA-MB-231 exosomes was found to be significantly decreased in cells treated with PEG-SMRwt-Clu and SMRwt-CPP, however, no significant changes were observed following treatment with the three mortalin inhibitors. Vimentin expression was significantly decreased following treatment with PEG-SMRwt-Clu, SMRwt-CPP and DMA, however, no significant change was observed following treatment with MKT-077 or omeprazole (FIG. 12, Panel B, middle top sub-panel). Mortalin expression was significantly decreased following treatment with PEG-SMRwt-Clu and SMRwt-CPP treatment, and to a lesser extent following DMA treatment (FIG. 12, Panel B, middle bottom sub-panel. No significant change was observed following treatment of MDA-MB-231 cells with MKT-077 or omeprazole treatment.

In K562 leukemia cells (FIG. 12 Panel A, top right sub-panel and FIG. 12 Panel B, top right sub-panel), Alix expression in K562 exosomes was significantly decreased following treatment with PEG-SMRwt-Clu, SMRwt-CPP, MKT-077, omeprazole and DMA. In contrast, vimentin expression in K562 exosomes was significantly following treatment with MKT-077, Omeprazole and DMA, however, no significant changes in vimentin expression were observed following treatment with any of the wild-type or mutant SMR peptides (FIG. 12, Panel B, middle right sub-panel). Mortalin expression was significantly decreased following treatment with PEG-SMRwt-Clu, SMRwt-CPP, MKT-077, omeprazole and DMA. Taken together, the data from FIGS. 11 and 12 suggest that exosome numbers and exosome protein contents are modulated differently depending on the specific treatment.

Example 11: Effect of Mortalin Inhibitors on Paclitaxel- and Cisplatin-Induced Apoptosis The effect of mortalin inhibitor drugs (MKT-077, DMA, and Omeprazole) were examined alone and in combination with paclitaxel (or cisplatin) to observe their effects on apoptosis in MBA-MD-231, MCF-7, and K562 cells. In particular, these cells were treated for 48 hours with 300 µM/mL of DMA, 200 µM/mL of Omeprazole, or different concentrations of MKT-077 depending on the cell (MDA-MB-231, 925 nM/mL; MCF-7, 500 nM/mL, K562 cells, 337.5 nM/mL), each treatment being conducted alone or in combination with 1.6 uM/mL of paclitaxel or 2 mg/mL of cisplatin and assayed for apoptosis by a TUNEL assay (FIG. 13).

The results showed decreased apoptosis relative (i) to the MKT-077 alone (52.13%) versus incubation with paclitaxel (21.14%) and cisplatin (27.53%) on MDA-MB-231 cells (FIG. 13, Panel A). Also, decreased apoptosis relative to the MKT-077 alone (90.1%) versus with cisplatin (77.13%) on MCF-7 cells (FIG. 13, Panel B). And decreased apoptosis relative to the MKT-077 alone (82.7%) versus with cisplatin (60.43%) on K562 cells (FIG. 13, Panel C). However, no significant changes were observed with paclitaxel on MCF-7 cells and K562 cells. (ii) Decreased apoptosis with DMA alone (30.43%) versus incubated with cisplatin (23.03%) on MDA-MB-231 cells (FIG. 13, Panel A); decreased apoptosis relative to DMA alone (11.83%) versus with paclitaxel (9.43%) on MCF-7 cells (FIG. 13, Panel B); and decreased apoptosis relative to the DMA alone (15.2%) versus with paclitaxel (1.63%) and cisplatin (11.7%) on K562 cells (FIG. 13, Panel C). No significant changes were observed with paclitaxel on MCF-7 cells, and with cisplatin in MCF-7 cells. (iii) Increased apoptosis was observed for omeprazole alone (3.0%) versus incubated with paclitaxel (15.33%) and cisplatin (29.05%) on MDA-MB-231 cells (FIG. 13, Panel A); increased apoptosis for omeprazole alone (1.1%) versus with cisplatin (29.05%) on MCF-7 cells (FIG. 13, Panel B); and increased apoptosis relative to the omeprazole alone (6.1%) versus with cisplatin (13.5%) on K562 cells (FIG. 13, Panel C). No significant changes were observed with paclitaxel on MCF-7 cells and K562 cells although a very small, synergistic effect of omeprazole in combination with either drug was observed.

Example 12: SMRwt Peptides Block Mortalin-Driven Exosome Release of Complement-Dependent Cytotoxicity Complement-mediated cytotoxicity is a normal cellular mechanism for ridding the host of tumor cells. Mortalin/GRP75 has been shown to bind complement factor C9 and play a major role in development of resistance to complement-dependent cytotoxicity via mortalin induced exocytosis of the membrane attack complex (MAC) via exosomes (Pilzer et al., *Intl. Immunol.*, (2005) 17(9): p. 1239-1248). Therefore, it was of interest to see whether SMR peptide driven mortalin sequestration and functional disruption increases cell sensitivity to complement-induced cell death. Accordingly, MCF-7, MDA-MB-231, and K562 cells were treated with 280 nM PEG-SMRwt-Clu peptide or 560 nM SMRwt-CPP peptide alone for 60 min at 37° C., followed by treatment with 1 µg/mL anti-CXCR4 antibody and 50 µL normal human serum (NHS; as a source of complement) or normal heat-inactivated (human) serum (NIS) for an additional 60 min at 37° C. (FIG. 14). PEG-SMRmut-Clu peptide and SMRmut-CPP peptide were used as negative controls. The percentage of stained (dead) cells was determined by trypan blue exclusion and is representative of 3 independent experiments.

In the presence of functional complement (NHS), both of the SMRwt peptides significantly induced tumor cell death. More specifically, in MCF-7 cells treated with PEG-SMRwt-Clu, cell death increased from 2.1% under complement-negative conditions (bar 4) to 26% under complement-positive conditions (bar 8)(FIG. 14, Panel A); likewise, in MCF-7 cells treated with SMRwt-CPP, cell death increased from 2.1% under complement-negative conditions (bar 6) to 29% under complement-positive conditions (bar 10) (FIG. 14, Panel A). These effects were abolished in the presence of complement when upon treatment with the SMRmutant peptides (bars 9, 11) (FIG. 14, Panel A).

In MDA-MB-231 cells treated with PEG-SMRwt-Clu, cell death increased from 3.6% under complement-negative conditions (bar 4) to 76% under complement-positive conditions (bar 8)(FIG. 14, Panel B); likewise, in MDA-MB-231 cells treated with SMRwt-CPP, cell death increased from 3.6% under complement-negative conditions (bar 6) to 9% under complement-positive conditions (bar 10) (FIG. 14, Panel B). These effects were abolished in the presence of complement when upon treatment with the SMRmutant peptides (bars 9, 11) (FIG. 14, Panel B).

In K562 cells treated with PEG-SMRwt-Clu, cell death increased from 4.3% under complement-negative conditions (bar 4) to 55% under complement-positive conditions (bar 8)(FIG. 14, Panel C); likewise, in K562 cells treated with SMRwt-CPP, cell death increased from 4.3% under complement-negative conditions (bar 6) to 23% under complement-positive conditions (bar 10) (FIG. 14, Panel C). These effects were abolished in the presence of complement when upon treatment with the SMRmutant peptides (bars 9, 11) (FIG. 14, Panel C).

Taken together, these data show that SMR-induced mortalin sequestration and functional disruption is linked to complement-mediated sensitivity and cell death. Specifically, blocking mortalin function renders or enhances tumor cell sensitivity to complement-mediated cytotoxicity.

Example 13: Mortalin Small Interfering RNA (siRNA) Reduces Exosome Secretion and Induces Complement-Mediated Cytotoxicity siRNA knockdown of mortalin expression was employed to further evaluate the role of mortalin in reducing exosome secretion and protecting tumor cells from complement-mediated cytotoxicity. Briefly, MCF-7, MDA-MB-231 and K562 cells were cultured in exosome-free media at 37° C. for 24 hr. The cells were then transfected with a vector expressing double-stranded mortalin siRNAs (Shelton et al., *J Virol* (2012) 86(1): p. 406-19; Huang et al., *Oncotarget* (2017) 8(7): p. 11302-11315). Negative control cells were transfected with a vector expressing a double-stranded siRNA predicted not to target any known vertebrate gene.

Detection of mortalin protein in cells was measured by SDS-PAGE/Western blot analysis using anti-mortalin and anti-α-tubulin (internal control) antibodies (FIG. 15, Panel A). Quantitative results from Western blots were obtained by densitometry analysis of relative band intensities (FIG. 15, Panel B). Compared to the levels of mortalin expression in cells transfected with the negative control, transfection of the mortalin-targeted siRNA resulted in mortalin expression levels of: 21.86% in MCF-7 (FIG. 15, Panel B, left sub-panel), 6.28% in MDA-MB-231 (FIG. 15, Panel B, middle sub-panel) and 35.3% in K562 (FIG. 15, Panel C, right sub-panel).

In addition, exosomes were isolated from the cell culture supernatants, and analyzed for concentration, and size distribution via NanoSight LM10 Nanoparticle Tracking Analysis (NTA). With NTA, particles are automatically tracked and sized, based on Brownian motion and the associated diffusion coefficient. Before analysis of the samples by NTA, it was determined that salt aggregates from PBS did not contribute to background and that equipment was free of contaminant particles.

The results of this analysis are shown in FIG. 15, Panel C. In MCF-7 cells treated with the siRNA-Neg control, the cell culture supernatant was found to contain $3.91 \times 10^9$ particles/mL, while the mortalin siRNA treated cells were found to contain $5.79 \times 10^8$ particles/mL (p<2.02E-07)(FIG. 15, Panel C, left sub-panel). In MDA-MB-231 cells treated with the siRNA-Neg control, the cell culture supernatant was found to contain $5.71 \times 10^9$ particles/ml, while the mortalin siRNA treated cells were found to contain $3.46 \times 10^9$ particles/mL (p<1.82E-06)(FIG. 15, Panel C, middle sub-panel). In K562 cells treated with the siRNA-Neg control, the cell culture supernatant was found to contain $3.44 \times 10^9$ particles/mL, while the mortalin siRNA treated cells were found to contain $2.58 \times 10^8$ particles/mL (p<2.49E-06)(FIG. 15. Panel C, right sub-panel). In all three cultures, NTA estimated the size of the exosomes to be in the range of 30 to 47 nm (data not shown).

To further validate the ability of mortalin neutralization to render or enhance tumor cell sensitivity to complement-mediated cytotoxicity, MCF-7, MDA-MB-231 and K562 cells were transfected with vectors expressing mortalin siRNAs or negative control siRNAs, incubated for 72 hours at 37° C., treated with anti-CXCR4 antibody for 30 minutes at 4° C. followed by incubation with either NHS or NIS for 60 minutes at 37° C. The data from these experiments indicated that silencing of mortalin expression resulted in mortalin-mediated protection of cells from complement-dependent cytotoxicity at 38.02% relative to the negative control in MCF-7 cells (FIG. 15, Panel D, left sub-panel), at 40.55% relative to the negative control in MDA-MB-231 cells (FIG. 15, Panel D, middle sub-panel) and at 30.54% relative to the negative control in K562 cells (FIG. 15, Panel D, right subpanel).

Example 14: PEG-SMRwt-CLU Peptide Affect Migration of MCF-7 and MDA-MB-231 Breast Cancer Cells Migration, but not Non-Tumorigenic MCF-10A Cell migration or invasion is the fatal step in cancer progression and metastasis, and accounts for 90% of all human cancer mortalities. In addition, cell migration is central to a variety of different pathologic and physiologic processes across many disciplines of biology including wound healing, inflammation, cell growth and differentiation. Cell invasion refers to 3-dimensional migration of cells as they penetrate an extracellular matrix (ECM) and is a process typically associated with cancer cell metastasis. To further explore this process, it was of interest to determine whether SMRwt peptides inhibit breast cancer cell migration and invasion. Consequently, a migration assay was performed to examine whether SMRwt peptides blocked tumor cells migration.

Specifically, MDA-MB-231 and MCF-7 breast cancer cells were treated with 1120 nM SMR peptide in MCF-7 cells, 280 nM SMR peptide in MDA-MB-231 cells or 3 µM Latrunculin A (positive control; known migratory inhibitor) for 24 hours and cell migration assays were performed according to manufacturer's instructions (Calbiochem manual) using a fluorescence plate reader set at an excitation wavelength of 485 nm and an emission wavelength of 515 nm.

Figure 16:
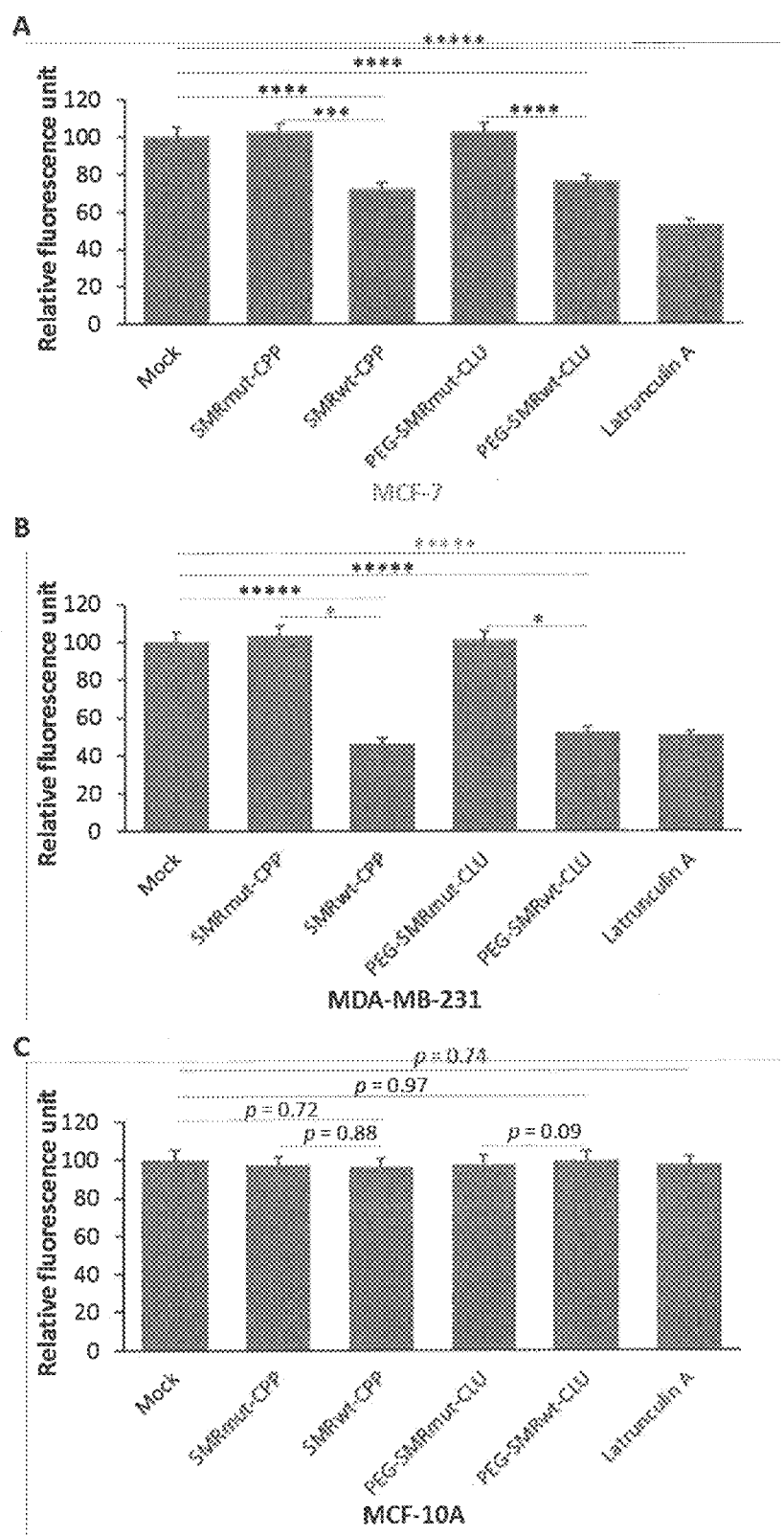
FIG. 16 shows that treatment of MDA-MB-231 and MCF-7 breast cancer cells with SMRwt peptides decreased their migration, while similar treatment of non-tumorigenic MCF-10A breast cells had no effect on migration. MDA-MB-231 and MCF-7 cells were treated with 1120 nM SMR peptide in MCF-7 cells, 280 nM SMR peptide in MDA-MB-231 cells or 3 μM Latrunculin A as control for 24 hours, and cell migration assays were performed according to manufacturer's instructions (Calbiochem manual) using a fluorescence plate reader set at an excitation wavelength of 485 nm and an emission wavelength of 515 nm. Panels A, B and C show relative fluorescence units of migration from: Panel A: MCF-7 breast cancer cells; Panel B: MDA-MB-231 breast cancer cells; and Panel C: MCF-10A non-tumorigenic breast cells. Error bars represent mean±SD of four independent experiments. Significant differences relative to SMRwt peptide are indicated as follows: * $p<0.01$, * $p<0.0001$,  $p<0.00001$, *** $p<0.000001$.

In MCF-7 cells, the SMRwt-CPP peptide, PEG-SMRwt-CLU peptide, and latrunculin A (the positive inhibitor control) reduced migration by 71.87%, 75.74%, and 53.05%, respectively (FIG. 16A). In MDA-MB-231 cells, the SMRwt-CPP peptide, PEG-SMRwt-CLU peptide, and latrunculin A reduced migration by 46.39%, 52.37%, and 50.39%, respectively (FIG. 16B). Further, the effects were specific for wild-type SMR peptides, as there was no significant inhibition of migration observed following treatment with mutant SMR peptides. In contrast, in MCF-10A, the normal breast cell line, migration was not significantly affected by any of the peptides or the inhibitor (FIG. 16C). Taken together, these data show that the SMRwt-CPP and PEG-SMRwt-CLU peptides significantly reduced breast cancer cell migration and invasion, while mutated SMR peptides had no statistically significant effect.

Example 15. Summary of Observations and Conclusions from Examples 8-14

A series of peptides derived from the Secretion Modification Region (SMR) of HIV-1 Nef protein were modified by addition of either a cell-penetrating peptide (CPP), a positively charged arginine-rich peptide derived from HIV-1 regulatory protein Tat, or a Clusterin (CLU) peptide, a molecular chaperone involved in protein secretion. Both CPP and CLU peptides were added at the C-terminus of the Nef SMR peptide. The CLU peptides were also modified with polyethylene glycol (PEG) to enhance solubility. After treatment of cells with the peptides, MTT cell viability and migration assays were used to confirm the inhibitory effect of these modified SMRwt peptides on the proliferation of MDA-MB-231 and MCF-7 breast cancer cells and K562 leukemia cells. Flow cytometry was used to determine complement mediated cell apoptosis and death. Western blot analysis was used to track peptide-mediated changes in expression of mortalin protein in both treated cells and exosomes released from the treated cells. NanoSight analyses and acetylcholinesterase (AChE) assays were employed for measuring exosome particle sizes and exosome concentrations in the media.

To investigate a functional role for mortalin in breast cancer and leukemia cells, mortalin knockdown experiments were conducted in MCF-7 and MDA-MB-231 breast cancer cells and leukemia cells and a series of assays were performed to examine the effects of mortalin expression and/or sequestration on cancer cell proliferation and metastasis. SMRwt peptides interacted with mortalin to significantly reduce cell proliferation and to inhibit cancer cell growth and cell migration/invasion. The oncogenic functions possessed by mortalin appear to be closely related in both breast cancer and leukemia cells. In particular, SMRwt peptides were found to interfere with the ability of mortalin to promote and protect cancer progression. First, the modified SMRwt peptides reduced the expression of the mesenchymal marker vimentin (VIM). Second, exposure to SMRwt peptides inhibited migration of breast cancer cells as measured by the migration assay. Third, the SMRwt peptides blocked the ability of cancer cells to release exosomes, which in turn blocked exosome-mediated release of complement, thereby re-establishing complement mediated cell death in those peptide-treated cells.

The data herein further show that: (i) SMRwt peptides not only effectively inhibited the growth of MDA-MB-231 and MCF-7 breast cancer cells but also unexpectedly inhibited the growth of a second, unrelated tumor line, K562 leukemia cells; (ii) Mortalin-SMR peptide interactions in cancer cells showed increased apoptosis, consistent with SMRwt peptide interfering with resistance of cancer cells to complement-dependent cytotoxicity; (iii) siRNA-mediated knockdown of mortalin reduced membrane attack complex (MAC) elimination and enhanced cell sensitivity to MAC-induced cell death; (iv) SMRwt peptides and the mortalin inhibitors, MKT-077, Omeprazole and 5-(N,N-Dimethyl)amiloride (DMA) blocked exosome secretion in MCF-7 and MDA-MB-231 breast cancer and K562 leukemia cells; and (v) PEG-SMRwt peptides inhibited MCF-7 and MDA-MB-231 breast cancer cell migration by blocking exosome release.

In conclusion, the data suggests mortalin promotes cell proliferation, invasion, and resistance to complement mediated cell death via induction of epithelial mesenchymal transition (EMT), for example, in leukemia cells. SMRwt peptides antagonize the functions of mortalin, blocking tumor exosome release and exosome-mediated release of complement, and antagonizing tumor cell migration and invasion associated with EMT. Treatment of cancer cells with these peptides alone or in combination with other active agents can reduce breast cancer and/or leukemia cell invasion and metastasis and facilitate standard treatment of these late stage tumor cells. The findings presented herein have important clinical implications and support further investigation into the therapeutic value of SMR peptides for treatment of cancer.

The above description is for the purpose of teaching the person of ordinary skill in the art how to practice the present disclosure, and it is not intended to detail all those obvious modifications and variations of it which will become apparent to the skilled worker upon reading the description. It is intended, however, that all such obvious modifications and variations be included within the scope of the present embodiment, which is defined by the following claims. The claims are intended to cover the claimed components and steps in any sequence that is effective to meet the objectives there intended, unless the context specifically indicates the contrary.

What is claimed is:

1. A method for treating a cancer, comprising:
   administering to a subject in need of such treatment an effective amount of a pharmaceutical composition comprising a multipartite peptide comprising at least one secretion modifying region (SMR) peptide from HIV-1 Nef fused to at least one cell-penetrating peptide (CPP), wherein the CPP comprises the amino acid sequence of GRKKRRQRRRPPQ (SEQ ID NO: 38).

2. The method of claim 1, wherein the SMR peptide comprises an amino acid sequence selected from the group consisting of VGFPV (SEQ ID NO: 1), VGFPVAAVGFPV (SEQ ID NO: 2), and NXNVGFPVAAVGFPV (SEQ ID NO: 36).

3. A method for treating a cancer, comprising:
administering to a subject in need of such treatment an effective amount of a pharmaceutical composition comprising a multipartite peptide comprising the amino acid sequence of NXNVGFPVAAVGFPVHPLSKH-PYWSQP (SEQ ID NO: 37), and wherein the multipartite peptide is pegylated.

4. The method of claim 1, wherein the subject has breast cancer.

5. The method of claim 1, further comprising the step of administering to the subject a second anti-cancer agent.

6. The method of claim 5, wherein the second anti-cancer agent is paclitaxel or cisplatin.

7. The method of claim 5, wherein the second anti-cancer agent is a mortalin inhibitor.

8. The method of claim 7, wherein the mortalin inhibitor is MKT-077, Omeprazole or 5-(N,N-dimethyl)amiloride (DMA).

9. A pharmaceutical composition comprising:
a multipartite peptide comprising at least one secretion modifying region (SMR) peptide from HIV-1 Nef fused to at least one cell-penetrating peptide (CPP), wherein the CPP comprises the amino acid sequence of GRK-KRRQRRRPPQ (SEQ ID NO: 38) or wherein the multipartite peptide comprises the amino acid sequence of VGFPVAAVGFPVGRKKRRQRRRPPQ (SEQ ID NO: 39); and
a pharmaceutically acceptable carrier,
wherein the pharmaceutical composition further comprises an anticancer agent is selected from the group consisting of mortalin (Hsp70) inhibitors, alkylating agents, anthracycline antibiotics, anti-metabolites, detoxifying agents, interferons, polyclonal or monoclonal antibodies, EGFR inhibitors, HER2 inhibitors, histone deacetylase inhibitors, hormones or anti-hormonal agents, mitotic inhibitors, phosphatidylinositol-3-kinase (PI3K) inhibitors, Akt inhibitors, mammalian target of rapamycin (mTOR) inhibitors, proteasomal inhibitors, poly(ADP-ribose) polymerase (PARP) inhibitors, Ras/MAPK pathway inhibitors, centrosome declustering agents, multi-kinase inhibitors, serine/threonine kinase inhibitors, tyrosine kinase inhibitors, VEGF/VEGFR inhibitors, taxanes or taxane derivatives, aromatase inhibitors, anthracyclines, microtubule targeting drugs, topoisomerase poison drugs, and combinations thereof.

10. The pharmaceutical composition of claim 9, wherein the anti-cancer agent is paclitaxel or cisplatin.

11. The pharmaceutical composition of claim 9, wherein the anti-cancer agent is a mortalin inhibitor.

12. The pharmaceutical composition of claim 9, wherein the multipartite peptide is pegylated.

13. The pharmaceutical composition of claim 9, wherein the multipartite peptide is incorporated into, onto, or otherwise associated with a nanoparticle.

14. A pharmaceutical composition comprising:
a multipartite peptide; and
a pharmaceutically acceptable carrier,
wherein the multipartite peptide comprise at least one secretion modifying region (SMR) peptide from HIV-1 Nef fused to at least one Clusterin (Clu)-binding peptide (Clu-BP),
wherein the multipartite peptide comprises the amino acid sequence of NXNVGFPVAAVGFPVHPLSKHPY-WSQP (SEQ ID NO: 37), and
wherein the multipartite peptide is pegylated.

15. The method of claim 3, wherein the subject has breast cancer.

16. The method of claim 3, wherein the subject has leukemia.

17. The method of claim 3, further comprising the step of administering to the subject a second anti-cancer agent selected from the group consisting of mortalin (Hsp70) inhibitors, alkylating agents, anthracycline antibiotics, anti-metabolites, detoxifying agents, interferons, polyclonal or monoclonal antibodies, EGFR inhibitors, HER2 inhibitors, histone deacetylase inhibitors, hormones or anti-hormonal agents, mitotic inhibitors, phosphatidylinositol-3-kinase (PI3K) inhibitors, Akt inhibitors, mammalian target of rapamycin (mTOR) inhibitors, proteasomal inhibitors, poly(ADP-ribose) polymerase (PARP) inhibitors, Ras/MAPK pathway inhibitors, centrosome declustering agents, multi-kinase inhibitors, serine/threonine kinase inhibitors, tyrosine kinase inhibitors, VEGF/VEGFR inhibitors, taxanes or taxane derivatives, aromatase inhibitors, anthracyclines, microtubule targeting drugs, topoisomerase poison drugs, and combinations thereof.

18. The method of claim 17, wherein the second anti-cancer agent is paclitaxel or cisplatin.

19. The method of claim 17, wherein the second anti-cancer agent is a mortalin inhibitor.

20. A method for treating a cancer, comprising:
administering to a subject in need of such treatment an effective amount of a pharmaceutical composition comprising an anti-cancer agent comprising at least one secretion modifying region (SMR) peptide from HIV-1 Nef fused to at least one cell-penetrating peptide (CPP), wherein the subject has leukemia.

* * * * *

SEQUENCE LISTING

<160> NUMBER OF SEQ ID NOS: 57

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Val Gly Phe Pro Val
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Val Gly Phe Pro Val Ala Ala Val Gly Phe Pro Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

His Pro Leu Ser Lys His Pro Tyr Trp Ser Gln Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Asn Thr Tyr Trp Ser Gln Leu Leu His Phe Gln Thr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Ser His Ala Leu Pro Leu Thr Trp Ser Thr Ala Ala
1               5                   10

<210> SEQ ID NO 6
<211> LENGTH: 24
<212> TYPE: PRT
<213> ORGANISM: Artificial Sequence
<220> FEATURE:
<223> OTHER INFORMATION: Synthetic

<400> SEQUENCE: 6

Val Gly Phe Pro Val Ala Ala Val Gly Phe Pro Val His Pro Leu Ser
1               5                   10                  15

```
Lys His Pro Tyr Trp Ser Gln Pro
            20

<210> SEQ ID NO 7
<211> LENGTH: 26
<212> TYPE: PRT
<213> ORGANISM: Artificial Sequence
<220> FEATURE:
<223> OTHER INFORMATION: Synthetic

<400> SEQUENCE: 7

Val Gly Phe Pro Val Ala Ala Val Gly Phe Pro Val Ala Ala His Pro
1               5                   10                  15

Leu Ser Lys His Pro Tyr Trp Ser Gln Pro
            20                  25

<210> SEQ ID NO 8
<211> LENGTH: 40
<212> TYPE: PRT
<213> ORGANISM: Artificial Sequence
<220> FEATURE:
<223> OTHER INFORMATION: Synthetic

<400> SEQUENCE: 8

Val Gly Phe Pro Val Ala Ala Val Gly Phe Pro Val Ala Ala His Pro
1               5                   10                  15

Leu Ser Lys His Pro Tyr Trp Ser Gln Pro Ala Ala His Pro Leu Ser
            20                  25                  30

Lys His Pro Tyr Trp Ser Gln Pro
            35                  40

<210> SEQ ID NO 9
<211> LENGTH: 29
<212> TYPE: PRT
<213> ORGANISM: Artificial Sequence
<220> FEATURE:
<223> OTHER INFORMATION: Synthetic

<400> SEQUENCE: 9

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic

<400> SEQUENCE: 10

Met Leu Ser Asn Leu Arg Ile Leu Leu Asn Lys Ala Ala Leu Arg Lys
1               5                   10                  15

Ala His Thr Ser Met Val Arg Asn Phe Arg Tyr Gly Lys Pro Val Gln
            20                  25                  30

Cys

<210> SEQ ID NO 11
<211> LENGTH: 18
<212> TYPE: PRT
<213> ORGANISM: Artificial Sequence
<220> FEATURE:
```

<223> OTHER INFORMATION: Synthetic

<400> SEQUENCE: 11

Met Leu Ser Leu Arg Gln Ser Ile Arg Phe Phe Lys Pro Ala Thr Arg
1               5                   10                  15

Thr Leu

<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 34
<212> TYPE: PRT
<213> ORGANISM: Artificial Sequence
<220> FEATURE:
<223> OTHER INFORMATION: Synthetic

<400> SEQUENCE: 13

Met Phe Ser Tyr Leu Pro Arg Tyr Pro Leu Arg Ala Ala Ser Ala Arg
1               5                   10                  15

Ala Leu Val Arg Ala Thr Arg Pro Ser Tyr Arg Ser Ala Leu Leu Arg
            20                  25                  30

Tyr Gln

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Met Ala Ala Trp Met Arg Ser Leu Phe Ser Pro Leu Lys Lys Leu Trp
1               5                   10                  15

Ile Arg Met His
            20

<210> SEQ ID NO 15
<211> LENGTH: 13
<212> TYPE: PRT
<213> ORGANISM: Artificial Sequence
<220> FEATURE:
<223> OTHER INFORMATION: Synthetic

<400> SEQUENCE: 15

Met Lys Leu Leu Trp Arg Leu Ile Leu Ser Arg Lys Trp
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic

<400> SEQUENCE: 16

Met Trp Trp Arg Arg Ser Arg Thr Asn Ser Leu Arg Tyr Thr
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthetic

<400> SEQUENCE: 17

Met Leu Phe Arg Leu Arg Arg Ser Val Arg Leu Arg Gly Leu Leu Ala
1               5                   10                  15

<210> SEQ ID NO 18
<211> LENGTH: 20
<212> TYPE: PRT
<213> ORGANISM: Artificial Sequence
<220> FEATURE:
<223> OTHER INFORMATION: Synthetic

<400> SEQUENCE: 18

Met Trp Thr Leu Gly Arg Arg Ala Val Ala Gly Leu Leu Ala Ser Pro
1               5                   10                  15

Ser Pro Ala Gln
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Arg Arg Ile Val Val Leu His Gly Tyr Gly Ala Val Lys Glu Val Leu
1               5                   10                  15

Leu Asn His Lys
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic

<400> SEQUENCE: 20

Met Leu Ser Leu Arg Gln Asp Ile Arg Phe Phe Lys Pro Ala Thr Arg
1               5                   10                  15

Thr Leu Cys Ser Ser Arg
            20

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Arg Pro Leu Ala Leu Trp Arg Ser
1               5

<210> SEQ ID NO 22

```
<211> LENGTH: 8
<212> TYPE: PRT
<213> ORGANISM: Artificial Sequence
<220> FEATURE:
<223> OTHER INFORMATION: Synthetic

<400> SEQUENCE: 22

Glu Ser Pro Ala Tyr Tyr Thr Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Asp Pro Arg Ser Phe Leu
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Pro Pro Arg Ser Phe Leu
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Arg Leu Gln Leu Lys Leu
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: ACETYLATION

<400> SEQUENCE: 26

Arg Leu Gln Leu Lys
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
```

```
<400> SEQUENCE: 27

Arg Xaa Xaa Arg
1

<210> SEQ ID NO 28
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa is Lys or Arg

<400> SEQUENCE: 28

Arg Xaa Xaa Arg
1

<210> SEQ ID NO 29
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is Glu or Asp

<400> SEQUENCE: 29

Ile Xaa Gly Arg
1

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Leu Val Pro Arg Gly Ser
1               5

<210> SEQ ID NO 31
<211> LENGTH: 13
<212> TYPE: DNA
<213> ORGANISM: Artificial Sequence
<220> FEATURE:
<223> OTHER INFORMATION: Synthetic

<400> SEQUENCE: 31
ccgccaagaa gcg                                                          13

<210> SEQ ID NO 32
<211> LENGTH: 100
<212> TYPE: DNA
<213> ORGANISM: Artificial Sequence
<220> FEATURE:
<223> OTHER INFORMATION: Synthetic

<400> SEQUENCE: 32
gcgtgcacac gcgcgtagac ttcccccgca agtcactcgt tagcccgcca agaagcgacc      60
```

```
cctccggggc gagctgagcg gcgtggcgcg ggggcgtcat                              100
```

<210> SEQ ID NO 33
<211> LENGTH: 101
<212> TYPE: DNA
<213> ORGANISM: Artificial Sequence
<220> FEATURE:
<223> OTHER INFORMATION: Synthetic

<400> SEQUENCE: 33

```
acgtgcatac gcacgtagac attccccgct tcccactcca aagtccgcca agaagcgtat       60
cccgctgagc ggcgtggcgc gggggcgtca tccgtcagct c                          101
```

<210> SEQ ID NO 34
<211> LENGTH: 58
<212> TYPE: DNA
<213> ORGANISM: Artificial Sequence
<220> FEATURE:
<223> OTHER INFORMATION: Synthetic

<400> SEQUENCE: 34

```
acttccccccg caagtcactc gttagcccgc caagaagcga cccctccggg gcgagctg        58
```

<210> SEQ ID NO 35
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: At least one and up to four may be present
<220> FEATURE:
<221> NAME/KEY: misc_feature
<222> LOCATION: (5)..(5)
<223> OTHER INFORMATION: Xaa is Ser or Ala
<220> FEATURE:
<221> NAME/KEY: misc_feature
<222> LOCATION: (6)..(20)
<223> OTHER INFORMATION: "Gly(1-4)-Ser/Ala" may or may not be present

<400> SEQUENCE: 35

```
Gly Gly Gly Gly Xaa Gly Gly Gly Gly Xaa Gly Gly Gly Gly Xaa Gly
1               5                   10                  15

Gly Gly Gly Xaa
            20
```

<210> SEQ ID NO 36
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 36

```
Asn Xaa Asn Val Gly Phe Pro Val Ala Ala Val Gly Phe Pro Val
1               5                   10                  15
```

<210> SEQ ID NO 37
<211> LENGTH: 27
<212> TYPE: PRT
<213> ORGANISM: Artificial Sequence

```
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 37

Asn Xaa Asn Val Gly Phe Pro Val Ala Ala Val Gly Phe Pro Val His
1               5                   10                  15

Pro Leu Ser Lys His Pro Tyr Trp Ser Gln Pro
            20                  25

<210> SEQ ID NO 38
<211> LENGTH: 13
<212> TYPE: PRT
<213> ORGANISM: Human immunodeficiency virus

<400> SEQUENCE: 38

Gly Arg Lys Lys Arg Arg Gln Arg Arg Arg Pro Pro Gln
1               5                   10

<210> SEQ ID NO 39
<211> LENGTH: 25
<212> TYPE: PRT
<213> ORGANISM: ARTIFICIAL SEQUENCE
<220> FEATURE:
<223> OTHER INFORMATION: Synthetic

<400> SEQUENCE: 39

Val Gly Phe Pro Val Ala Ala Val Gly Phe Pro Val Gly Arg Lys Lys
1               5                   10                  15

Arg Arg Gln Arg Arg Arg Pro Pro Gln
            20                  25

<210> SEQ ID NO 40
<211> LENGTH: 12
<212> TYPE: PRT
<213> ORGANISM: ARTIFICIAL SEQUENCE
<220> FEATURE:
<223> OTHER INFORMATION: Synthetic

<400> SEQUENCE: 40

Ala Gly Phe Pro Val Ala Ala Ala Gly Phe Pro Val
1               5                   10

<210> SEQ ID NO 41
<211> LENGTH: 25
<212> TYPE: PRT
<213> ORGANISM: ARTIFICIAL SEQUENCE
<220> FEATURE:
<223> OTHER INFORMATION: Synthetic

<400> SEQUENCE: 41

Ala Gly Phe Pro Val Ala Ala Ala Gly Phe Pro Val Gly Arg Lys Lys
1               5                   10                  15

Arg Arg Gln Arg Arg Arg Pro Pro Gln
            20                  25

<210> SEQ ID NO 42
<211> LENGTH: 15
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (2)..(2)
<223> OTHER INFORMATION: Xaa can be any naturally occurring amino acid

<400> SEQUENCE: 42

Asn Xaa Asn Ala Gly Phe Pro Val Ala Ala Ala Gly Phe Pro Val
1               5                   10                  15

<210> SEQ ID NO 43
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 43

Asn Xaa Asn Ala Gly Phe Pro Val Ala Ala Ala Gly Phe Pro Val His
1               5                   10                  15

Pro Leu Ser Lys His Pro Tyr Trp Ser Gln Pro
            20                  25

<210> SEQ ID NO 44
<211> LENGTH: 24
<212> TYPE: PRT
<213> ORGANISM: ARTIFICIAL SEQUENCE
<220> FEATURE:
<223> OTHER INFORMATION: Synthetic

<400> SEQUENCE: 44

Ala Gly Phe Pro Val Ala Ala Ala Gly Phe Pro Val His Pro Leu Ser
1               5                   10                  15

Lys His Pro Tyr Trp Ser Gln Pro
            20

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Gly Gly Gly Gly His Leu Asn Ile Leu Ser Thr Leu Trp Lys Tyr Arg
1               5                   10                  15

Cys

<210> SEQ ID NO 46
<211> LENGTH: 20
<212> TYPE: PRT
<213> ORGANISM: Artificial Sequence
<220> FEATURE:
<223> OTHER INFORMATION: Synthetic

<400> SEQUENCE: 46

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 47
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 47

Arg Arg Arg Arg Arg Arg Arg Arg
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic

<400> SEQUENCE: 48

Leu Arg Lys Leu Arg Lys Arg Leu Leu Arg
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Synthetic

<400> SEQUENCE: 49

Cys Gly His Lys Ala Lys Gly Pro Arg Lys Gly Lys Arg Lys
1               5                   10

<210> SEQ ID NO 50
<211> LENGTH: 16
<212> TYPE: PRT
<213> ORGANISM: Artificial Sequence
<220> FEATURE:
<223> OTHER INFORMATION: Synthetic

<400> SEQUENCE: 50

Phe Lys Glu Ser Trp Arg Glu Ala Arg Gly Thr Arg Ile Glu Arg Gly
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Lys Ser Val Arg Thr Trp Asn Glu Ile Ile Pro Ser Lys Gly Cys Leu
1               5                   10                  15

Arg

<210> SEQ ID NO 52
<211> LENGTH: 7
<212> TYPE: PRT
<213> ORGANISM: Artificial Sequence
<220> FEATURE:
<223> OTHER INFORMATION: Synthetic

<400> SEQUENCE: 52

His Ala Ile Tyr Pro Arg His
1               5

<210> SEQ ID NO 53
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 53

Thr Gly Asn Tyr Lys Ala Leu His Pro His Asn Gly
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic

<400> SEQUENCE: 54

Thr His Arg Pro Pro Met Trp Ser Pro Val Trp Pro
1               5                   10

<210> SEQ ID NO 55
<211> LENGTH: 29
<212> TYPE: PRT
<213> ORGANISM: Artificial Sequence
<220> FEATURE:
<223> OTHER INFORMATION: Synthetic

<400> SEQUENCE: 55

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 56
<211> LENGTH: 6
<212> TYPE: PRT
<213> ORGANISM: Artificial Sequence
<220> FEATURE:
<223> OTHER INFORMATION: Synthetic

<400> SEQUENCE: 56

Pro Leu Gly Leu Ala Gly
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: 2'-O-methylation

<400> SEQUENCE: 57

Pro Leu Gly Cys Ala Gly
1               5
```